US009096671B2

(12) United States Patent
Llorente Cortés et al.

(10) Patent No.: US 9,096,671 B2

(45) Date of Patent: Aug. 4, 2015

(54) LRP1 AS KEY RECEPTOR FOR THE TRANSFER OF STERIFIED CHOLESTEROL FROM VERY-LOW-DENSITY LIPOPROTEINS (VLDL) TO ISCHAEMIC CARDIAC MUSCLE

(75) Inventors: Concepción Vicenta Llorente Cortés, Barcelona (ES); Lina Badimon Maestro, Barcelona (ES)

(73) Assignees: CONSEJO SUPERIOR DE INVESTIGACIONES CIENTIFICAS (CSIC), Madrid (ES); INSTITUTO CATALAN DE CIENCIAS CARDIOVASCULARES (ICCC), Barcelona (ES)

( * ) Notice: Subject to any disclaimer, the term of this patent is extended or adjusted under 35 U.S.C. 154(b) by 0 days.

(21) Appl. No.: 14/129,446

(22) PCT Filed: Jun. 29, 2012

(86) PCT No.: PCT/ES2012/070483

§ 371 (c)(1), (2), (4) Date: Mar. 31, 2014

(87) PCT Pub. No.: WO2013/001130

PCT Pub. Date: Jan. 3, 2013

(65) Prior Publication Data

US 2014/0220038 A1 Aug. 7, 2014

(30) Foreign Application Priority Data

Jun. 29, 2011 (ES) .................................. 201131092

(51) Int. Cl.

| | |
|---|---|
| ***C07K 4/00*** | (2006.01) |
| ***C07K 4/12*** | (2006.01) |
| ***A61K 38/10*** | (2006.01) |
| ***A61K 39/00*** | (2006.01) |
| ***C12N 15/113*** | (2010.01) |
| ***C07K 14/775*** | (2006.01) |
| *C07K 14/705* | (2006.01) |
| *C07K 16/28* | (2006.01) |

(52) U.S. Cl.

CPC ................ *C07K 16/28* (2013.01); *A61K 38/10* (2013.01); *A61K 39/0005* (2013.01); *C07K 4/12* (2013.01); *C07K 14/705* (2013.01); *C07K 14/775* (2013.01); *C12N 15/113* (2013.01); *C12N 15/1138* (2013.01); *C07K 2317/34* (2013.01); *C07K 2317/76* (2013.01); *C12N 2310/14* (2013.01)

(58) Field of Classification Search

None

See application file for complete search history.

(56) References Cited

PUBLICATIONS

Horn et al, 1997. J Biol Chem. 272: 13608-13613.*

International Search Report issued Nov. 6, 2012 in International (PCT) Application No. PCT/ES2012/070483.

Cal et al., "Low-density lipoprotein receptor-related protein 1 mediates hypoxia-induced very low density lipoprotein-cholesteryl ester uptake and accumulation in cardiomyocytes", Cardiovascular Research, vol. 94, 2012, pp. 469-479.

Llorente-Cortes et al., "LDL Receptor-Related Protein Mediates Uptake of Aggregated LDL in Human Vascular Smooth Muscle Cells", Arteriosclerosis, Thrombosis, and Vascular Biology, vol. 20, 2000, pp. 1572-1579.

Llorente-Cortes et al., "Cholesteryl Esters of Aggregated LDL Are Internalized by Selective Uptake in Human Vascular Smooth Muscle Cells", Arteriosclerosis, Thrombosis, and Vascular Biology, vol. 26, Oct. 27, 2005, pp. 117-123.

Llorente-Cortes et al., "Adipocyte differentiation-related protein is induced by LRP1-mediated aggregated LDL internalization in human vascular smooth muscle cells and macrophages", Journal of Lipid Research, vol. 48, 2007, pp. 2133-2140.

Castellano et al., "Hypoxia Stimulates Low-Density Lipoprotein Receptor-Related Protein-1 Expression Through Hypoxia-Inducible Factor-1 α in Human Vascular Smooth Muscle Cells", Arteriosclerosis, Thrombosis, and Vascular Biology, vol. 31, Mar. 31, 2011, pp. 1411-1420.

Fuentealba et al., "Mechanisms of Signal Transduction: Low Density Lipoprotein Receptor-related Protein 1 Promotes Anti-apoptotic Signaling in Neurons by Activating Akt Survival Pathway", The Journal of Biological Chemistry, vol. 284, 2009, pp. 34045-34053.

* cited by examiner

*Primary Examiner* — Zachary Howard

(74) *Attorney, Agent, or Firm* — Wenderoth, Lind & Ponack, L.L.P.

(57) ABSTRACT

The invention relates to novel molecules that can modulate one of the mechanisms leading to the massive deposition of cholesterol in the cardiomyocytes and/or in the smooth muscle cells of the vascular wall, during acute myocardial infarction or other clinical situations involving ischaemia. The invention also shows that the blockage of LRP1 by means of certain agents, including a recombinant expression vector, an RNAi, an antibody, a siRNA etc., prevents the overaccumulation of esterified cholesterol in the cardiomyocytes and/or in the smooth muscle cells of the vascular wall exposed to ischaemia. The invention also relates to the use of said molecules in the treatment and/or prevention of the changes in the metabolism of calcium and cardiac remodeling associated with ischaemia.

2 Claims, 26 Drawing Sheets

CNT: control

DCM: dilater cardiomyopathy

ICM: ischaemic cardiomyopathy

LRP1 protein expression
(normalized by β-tubulin)
50
45
40
35
30
25
20
15
10
5
0
siRNA random
siRNA CHFR
non LDL
agLDL CHRF protein expression
(normalized by β-tubulin)
35
30
25
20
15
10
5
0
siRNA random
siRNA CHFR

SEQUENCE LISTING

<160> NUMBER OF SEQ ID NOS: 24

<210> SEQ ID NO 1
<211> LENGTH: 64
<212> TYPE: RNA
<213> ORGANISM: Artificial Sequence
<220> FEATURE:
<223> OTHER INFORMATION: Synthetic Construct

<400> SEQUENCE: 1
ugcugcauac acgaggaaca gcucauguuu uggccacuga cugacaugag cugccucgug 60
uaug 64

<210> SEQ ID NO 2
<211> LENGTH: 64
<212> TYPE: RNA
<213> ORGANISM: Artificial Sequence
<220> FEATURE:
<223> OTHER INFORMATION: Synthetic Construct

<400> SEQUENCE: 2
ccugcauaca cgaggcagcu caugucaguc aguggccaaa acaugagcug uuccucgugu 60
augc 64

<210> SEQ ID NO 3
<211> LENGTH: 64
<212> TYPE: RNA
<213> ORGANISM: Artificial Sequence
<220> FEATURE:
<223> OTHER INFORMATION: Synthetic Construct

<400> SEQUENCE: 3
ugcuguccuc acaauccaca aacuggguuu uggccacuga cugacccagu uuggauugug 60
agga 64

<210> SEQ ID NO 4
<211> LENGTH: 64
<212> TYPE: RNA
<213> ORGANISM: Artificial Sequence
<220> FEATURE:
<223> OTHER INFORMATION: Synthetic Construct

<400> SEQUENCE: 4
ccuguccuca caauccaaac ugggucaguc aguggccaaa acccaguuug uggauuguga 60
ggac 64

<210> SEQ ID NO 5
<211> LENGTH: 64
<212> TYPE: RNA
<213> ORGANISM: Artificial Sequence
<220> FEATURE:
<223> OTHER INFORMATION: Synthetic Construct

<400> SEQUENCE: 5
ugcugagcag aacuuguugc agugggguuu uggccacuga cugaccccac ugccaaguuc 60
ugcu 64

<210> SEQ ID NO 6
<211> LENGTH: 64
<212> TYPE: RNA
<213> ORGANISM: Artificial Sequence
<220> FEATURE:
<223> OTHER INFORMATION: Synthetic Construct

<400> SEQUENCE: 6
ccugagcaga acuuggcagu ggggucaguc aguggccaaa accccacugc aacaaguucu 60
gcuc 64

<210> SEQ ID NO 7
<211> LENGTH: 64
<212> TYPE: RNA
<213> ORGANISM: Artificial Sequence
<220> FEATURE:
<223> OTHER INFORMATION: Synthetic Construct

<400> SEQUENCE: 7
ugcugaaaug uacugcgcgu ggagacguuu uggccacuga cugacgucuc cacgcaguac 60
auuu 64

<210> SEQ ID NO 8
<211> LENGTH: 64
<212> TYPE: RNA
<213> ORGANISM: Artificial Sequence
<220> FEATURE:
<223> OTHER INFORMATION: Synthetic Construct

<400> SEQUENCE: 8
ccugaaaugu acugcgugga gacgucaguc aguggccaaa acgucuccac gcgcaguaca 60
uuuc 64

<210> SEQ ID NO 9
<211> LENGTH: 11024
<212> TYPE: DNA
<213> ORGANISM: Artificial Sequence
<220> FEATURE:
<223> OTHER INFORMATION: Synthetic Construct

<400> SEQUENCE: 9
aatgtagtct tatgcaatac tcttgtagtc ttgcaacatg gtaacgatga gttagcaaca 60
tgccttacaa ggagagaaaa agcaccgtgc atgccgattg gtggaagtaa ggtggtacga 120
tcgtgcctta ttaggaaggc aacagacggg tctgacatgg attggacgaa ccactgaatt 180
gccgcattgc agagatattg tatttaagtg cctagctcga tacataaacg ggtctctctg 240
gttagaccag atctgagcct gggagctctc tggctaacta gggaacccac tgcttaagcc 300
tcaataaagc ttgccttgag tgcttcaagt agtgtgtgcc cgtctgttgt gtgactctgg 360
taactagaga tccctcagac ccttttagtc agtgtggaaa atctctagca gtggcgcccg 420
aacagggact tgaaagcgaa agggaaacca gaggagctct ctcgacgcag gactcggctt 480
gctgaagcgc gcacggcaag aggcgagggg cggcgactgg tgagtacgcc aaaaattttg 540
actagcggag gctagaagga gagagatggg tgcgagagcg tcagtattaa gcgggggaga 600
attagatcgc gatgggaaaa aattcggtta aggccagggg gaaagaaaaa atataaatta 660

```
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgatt   1800
aacttttaaa agaaaagggg ggattggggg gtacagtgca ggggaaagaa tagtagacat   1860
aatagcaaca gacatacaaa ctaaagaatt acaaaaacaa attacaaaaa ttcaaaattt   1920
tatcgatgtc gacgttaacg ctagtgatat caactttgta tagaaaagtt gaagcttggg   1980
agttccgcgt tacataactt acggtaaatg gcccgcctgg ctgaccgccc aacgaccccc   2040
gcccattgac gtcaataatg acgtatgttc ccatagtaac gccaataggg actttccatt   2100
gacgtcaatg ggtggagtat ttacggtaaa ctgcccactt ggcagtacat caagtgtatc   2160
atatgccaag tacgccccct attgacgtca atgacggtaa atggcccgcc tggcattatg   2220
cccagtacat gaccttatgg gactttccta cttggcagta catctacgta ttagtcatcg   2280
ctattaccat ggtgatgcgg ttttggcagt acatcaatgg gcgtggatag cggtttgact   2340
cacggggatt tccaagtctc caccccattg acgtcaatgg gagtttgttt tggcaccaaa   2400
atcaacggga ctttccaaaa tgtcgtaaca actccgcccc attgacgcaa atgggcggta   2460
ggcgtgtacg gtgggaggtc tatataagca gagctcgttt agtgaaccgt cagatcgcct   2520
ggagacgcca tccacgctgt tttgacctcc atagaagaca ccgactctag aggatccact   2580
agtccagtgt ggtggaattc tgcagatatc acaagtttgt acaaaaaagc aggctccgcg   2640
gccgccccct tcaccatgat agatcccgtc gttttacaac gtcgtgactg ggaaaaccct   2700
ggcgttaccc aacttaatcg ccttgcagca catccccctt tcgccagctg gcgtaatagc   2760
gaagaggccc gcaccgatcg cccttcccaa cagttgcgca gcctgaatgg cgaatggcgc   2820
tttgcctggt ttccggcacc agaagcggtg ccggaaagct ggctggagtg cgatcttcct   2880
gaggccgata ctgtcgtcgt cccctcaaac tggcagatgc acggttacga tgcgcccatc   2940
tacaccaacg tgacctatcc cattacggtc aatccgccgt ttgttcccac ggagaatccg   3000
acgggttgtt actcgctcac atttaatgtt gatgaaagct ggctacagga aggccagacg   3060
```

cgaattattt ttgatggcgt taactcggcg tttcatctgt ggtgcaacgg gcgctgggtc 3120
ggttacggcc aggacagtcg tttgccgtct gaatttgacc tgagcgcatt tttacgcgcc 3180
ggagaaaacc gcctcgcggt gatggtgctg cgctggagtg acggcagtta tctggaagat 3240
caggatatgt ggcggatgag cggcattttc cgtgacgtct cgttgctgca taaaccgact 3300
acacaaatca gcgatttcca tgttgccact cgctttaatg atgatttcag ccgcgctgta 3360
ctggaggctg aagttcagat gtgcggcgag ttgcgtgact acctacgggt aacagtttct 3420
ttatggcagg gtgaaacgca ggtcgccagc ggcaccgcgc ctttcggcgg tgaaattatc 3480
gatgagcgtg gtggttatgc cgatcgcgtc acactacgtc tgaacgtcga aaacccgaaa 3540
ctgtggagcg ccgaaatccc gaatctctat cgtgcggtgg ttgaactgca caccgccgac 3600
ggcacgctga ttgaagcaga agcctgcgat gtcggtttcc gcgaggtgcg gattgaaaat 3660
ggtctgctgc tgctgaacgg caagccgttg ctgattcgag gcgttaaccg tcacgagcat 3720
catcctctgc atggtcaggt catggatgag cagacgatgg tgcaggatat cctgctgatg 3780
aagcagaaca actttaacgc cgtgcgctgt tcgcattatc cgaaccatcc gctgtggtac 3840
acgctgtgcg accgctacgg cctgtatgtg gtggatgaag ccaatattga aacccacggc 3900
atggtgccaa tgaatcgtct gaccgatgat ccgcgctggc taccggcgat gagcgaacgc 3960
gtaacgcgaa tggtgcagcg cgatcgtaat cacccgagtg tgatcatctg gtcgctgggg 4020
aatgaatcag gccacggcgc taatcacgac gcgctgtatc gctggatcaa atctgtcgat 4080
ccttcccgcc cggtgcagta tgaaggcggc ggagccgaca ccacggccac cgatattatt 4140
tgcccgatgt acgcgcgcgt ggatgaagac cagcccttcc cggctgtgcc gaaatggtcc 4200
atcaaaaaat ggctttcgct acctggagag acgcgcccgc tgatcctttg cgaatacgcc 4260
cacgcgatgg gtaacagtct tggcggtttc gctaaatact ggcaggcgtt tcgtcagtat 4320
ccccgtttac agggcggctt cgtctgggac tgggtggatc agtcgctgat taaatatgat 4380
gaaaacggca acccgtggtc ggcttacggc ggtgattttg gcgatacgcc gaacgatcgc 4440
cagttctgta tgaacggtct ggtctttgcc gaccgcacgc cgcatccagc gctgacggaa 4500
gcaaaacacc agcagcagtt tttccagttc cgtttatccg ggcaaaccat cgaagtgacc 4560
agcgaatacc tgttccgtca tagcgataac gagctcctgc actggatggt ggcgctggat 4620
ggtaagccgc tggcaagcgg tgaagtgcct ctggatgtcg ctccacaagg taaacagttg 4680
attgaactgc ctgaactacc gcagccggag agcgccgggc aactctggct cacagtacgc 4740
gtagtgcaac cgaacgcgac cgcatggtca gaagccggcc acatcagcgc ctggcagcag 4800
tggcgtctgg cggaaaacct cagtgtgacg ctccccgccg cgtcccacgc catcccgcat 4860
ctgaccacca gcgaaatgga tttttgcatc gagctgggta ataagcgttg gcaatttaac 4920
cgccagtcag gctttctttc acagatgtgg attggcgata aaaaacaact gctgacgccg 4980
ctgcgcgatc agttcacccg tgcaccgctg gataacgaca ttggcgtaag tgaagcgacc 5040
cgcattgacc ctaacgcctg ggtcgaacgc tggaaggcgg cgggccatta ccaggccgaa 5100
gcagcgttgt tgcagtgcac ggcagataca cttgctgacg cggtgctgat tacgaccgct 5160
cacgcgtggc agcatcaggg gaaaacctta tttatcagcc ggaaaaccta ccggattgat 5220
ggtagtggtc aaatggcgat taccgttgat gttgaagtgg cgagcgatac accgcatccg 5280
gcgcggattg gcctgaactg ccagctggcg caggtagcag agcgggtaaa ctggctcgga 5340
ttagggccgc aagaaaacta tcccgaccgc cttactgccg cctgttttga ccgctgggat 5400
ctgccattgt cagacatgta taccccgtac gtcttcccga gcgaaaacgg tctgcgctgc 5460

```
gggacgcgcg aattgaatta tggcccacac cagtggcgcg gcgacttcca gttcaacatc   5520
agccgctaca gtcaacagca actgatggaa accagccatc gccatctgct gcacgcggaa   5580
gaaggcacat ggctgaatat cgacggtttc catatgggga ttggtggaga cgactcctgg   5640
agcccgtcag tatcggcgga attacagctg agcgccggtc gctaccatta ccagttggtc   5700
tggtgtcaaa aaactaaggg tgggcgcgcc gacccagctt tcttgtacaa agtggttgat   5760
atccagcaca gtggcggccg ctcgagtcta gagggcccgc ggttcgaagg taagcctatc   5820
cctaaccctc tcctcggtct cgattctacg cgtaccggtt agtaatgatc gacaatcaac   5880
ctctggatta caaaatttgt gaaagattga ctggtattct taactatgtt gctcctttta   5940
cgctatgtgg atacgctgct ttaatgcctt tgtatcatgc tattgcttcc cgtatggctt   6000
tcattttctc ctccttgtat aaatcctggt tgctgtctct ttatgaggag ttgtggcccg   6060
ttgtcaggca acgtggcgtg gtgtgcactg tgtttgctga cgcaaccccc actggttggg   6120
gcattgccac cacctgtcag ctcctttccg ggactttcgc tttccccctc cctattgcca   6180
cggcggaact catcgccgcc tgccttgccc gctgctggac aggggctcgg ctgttgggca   6240
ctgacaattc cgtggtgttg tcggggaagc tgacgtcctt tccatggctg ctcgcctgtg   6300
ttgccacctg gattctgcgc gggacgtcct tctgctacgt cccttcggcc ctcaatccag   6360
cggaccttcc ttcccgcggc ctgctgccgg ctctgcggcc tcttccgcgt cttcgccttc   6420
gccctcagac gagtcggatc tccctttggg ccgcctcccc gcctggcgat ggtacctacc   6480
gggtagggga ggcgcttttc ccaaggcagt ctggagcatg cgctttagca gccccgctgg   6540
gcacttggcg ctacacaagt ggcctctggc ctcgcacaca ttccacatcc accggtaggc   6600
gccaaccggc tccgttcttt ggtggcccct tcgcgccacc ttctactcct cccctagtca   6660
ggaagttccc ccccgccccg cagctcgcgt cgtgcaggac gtgacaaatg gaagtagcac   6720
gtctcactag tctcgtgcag atggacagca ccgctgagca atggaagcgg gtaggccttt   6780
ggggcagcgg ccaatagcag ctttgctcct tcgctttctg ggctcagagg ctgggaaggg   6840
gtgggtccgg gggcgggctc aggggcgggc tcaggggcgg ggcgggcgcc cgaaggtcct   6900
ccggaggccc ggcattctgc acgcttcaaa agcgcacgtc tgccgcgctg ttctcctctt   6960
cctcatctcc gggcctttcg actctagaca cgtgttgaca attaatcatc ggcatagtat   7020
atcggcatag tataatacga caaggtgagg aactaaacca tggccaagcc tttgtctcaa   7080
gaagaatcca ccctcattga aagagcaacg gctacaatca acagcatccc catctctgaa   7140
gactacagcg tcgccagcgc agctctctct agcgacggcc gcatcttcac tggtgtcaat   7200
gtatatcatt ttactggggg accttgtgca gaactcgtgg tgctgggcac tgctgctgct   7260
gcggcagctg gcaacctgac ttgtatcgtc gcgatcggaa atgagaacag gggcatcttg   7320
agcccctgcg gacggtgccg acaggtgctt ctcgatctgc atcctgggat caaagccata   7380
gtgaaggaca gtgatggaca gccgacggca gttgggattc gtgaattgct gccctctggt   7440
tatgtgtggg agggctaagc acaattcgag ctcggtacct ttaagaccaa tgacttacaa   7500
ggcagctgta gatcttagcc actttttaaa agaaaagggg ggactggaag ggctaattca   7560
ctcccaacga agacaagatc tgctttttgc ttgtactggg tctctctggt tagaccagat   7620
ctgagcctgg gagctctctg gctaactagg gaacccactg cttaagcctc aataaagctt   7680
gccttgagtg cttcaagtag tgtgtgcccg tctgttgtgt gactctggta actagagatc   7740
cctcagaccc ttttagtcag tgtggaaaat ctctagcagt agtagttcat gtcatcttat   7800
```

-continued

```
tattcagtat ttataacttg caaagaaatg aatatcagag agtgagagga acttgtttat   7860
tgcagcttat aatggttaca aataaagcaa tagcatcaca aatttcacaa ataaagcatt   7920
tttttcactg cattctagtt gtggtttgtc caaactcatc aatgtatctt atcatgtctg   7980
gctctagcta tcccgcccct aactccgccc atcccgcccc taactccgcc cagttccgcc   8040
cattctccgc cccatggctg actaattttt tttatttatg cagaggccga ggccgcctcg   8100
gcctctgagc tattccagaa gtagtgagga ggcttttttg gaggcctagg gacgtaccca   8160
attcgcccta tagtgagtcg tattacgcgc gctcactggc cgtcgtttta caacgtcgtg   8220
actgggaaaa ccctggcgtt acccaactta atcgccttgc agcacatccc cctttcgcca   8280
gctggcgtaa tagcgaagag gcccgcaccg atcgcccttc ccaacagttg cgcagcctga   8340
atggcgaatg ggacgcgccc tgtagcggcg cattaagcgc ggcgggtgtg gtggttacgc   8400
gcagcgtgac cgctacactt gccagcgccc tagcgcccgc tcctttcgct ttcttccctt   8460
cctttctcgc cacgttcgcc ggctttcccc gtcaagctct aaatcggggg ctccctttag   8520
ggttccgatt tagtgcttta cggcacctcg accccaaaaa acttgattag ggtgatggtt   8580
cacgtagtgg gccatcgccc tgatagacgg tttttcgccc tttgacgttg gagtccacgt   8640
tctttaatag tggactcttg ttccaaactg gaacaacact caaccctatc tcggtctatt   8700
cttttgattt ataagggatt ttgccgattt cggcctattg gttaaaaaat gagctgattt   8760
aacaaaaatt taacgcgaat tttaacaaaa tattaacgct tacaatttag gtggcacttt   8820
tcggggaaat gtgcgcggaa cccctatttg tttatttttc taaatacatt caaatatgta   8880
tccgctcatg agacaataac cctgataaat gcttcaataa tattgaaaaa ggaagagtat   8940
gagtattcaa catttccgtg tcgcccttat tccctttttt gcggcatttt gccttcctgt   9000
ttttgctcac ccagaaacgc tggtgaaagt aaaagatgct gaagatcagt tgggtgcacg   9060
agtgggttac atcgaactgg atctcaacag cggtaagatc cttgagagtt ttcgccccga   9120
agaacgtttt ccaatgatga gcacttttaa agttctgcta tgtggcgcgg tattatcccg   9180
tattgacgcc gggcaagagc aactcggtcg ccgcatacac tattctcaga atgacttggt   9240
tgagtactca ccagtcacag aaaagcatct tacggatggc atgacagtaa gagaattatg   9300
cagtgctgcc ataaccatga gtgataacac tgcggccaac ttacttctga caacgatcgg   9360
aggaccgaag gagctaaccg cttttttgca caacatgggg gatcatgtaa ctcgccttga   9420
tcgttgggaa ccggagctga atgaagccat accaaacgac gagcgtgaca ccacgatgcc   9480
tgtagcaatg gcaacaacgt tgcgcaaact attaactggc gaactactta ctctagcttc   9540
ccggcaacaa ttaatagact ggatggaggc ggataaagtt gcaggaccac ttctgcgctc   9600
ggcccttccg gctggctggt ttattgctga taaatctgga gccggtgagc gtgggtctcg   9660
cggtatcatt gcagcactgg ggccagatgg taagccctcc cgtatcgtag ttatctacac   9720
gacggggagt caggcaacta tggatgaacg aaatagacag atcgctgaga taggtgcctc   9780
actgattaag cattggtaac tgtcagacca agtttactca tatatacttt agattgattt   9840
aaaacttcat ttttaattta aaaggatcta ggtgaagatc ctttttgata atctcatgac   9900
caaaatccct taacgtgagt tttcgttcca ctgagcgtca gaccccgtag aaaagatcaa   9960
aggatcttct tgagatcctt tttttctgcg cgtaatctgc tgcttgcaaa caaaaaaacc  10020
accgctacca gcggtggttt gtttgccgga tcaagagcta ccaactcttt ttccgaaggt  10080
aactggcttc agcagagcgc agataccaaa tactgttctt ctagtgtagc cgtagttagg  10140
ccaccacttc aagaactctg tagcaccgcc tacatacctc gctctgctaa tcctgttacc  10200
```

```
agtggctgct gccagtggcg ataagtcgtg tcttaccggg ttggactcaa gacgatagtt  10260

accggataag gcgcagcggt cgggctgaac ggggggttcg tgcacacagc ccagcttgga  10320

gcgaacgacc tacaccgaac tgagatacct acagcgtgag ctatgagaaa gcgccacgct  10380

tcccgaaggg agaaaggcgg acaggtatcc ggtaagcggc agggtcggaa caggagagcg  10440

cacgagggag cttccagggg gaaacgcctg gtatctttat agtcctgtcg ggtttcgcca  10500

cctctgactt gagcgtcgat ttttgtgatg ctcgtcaggg gggcggagcc tatggaaaaa  10560

cgccagcaac gcggcctttt tacggttcct ggccttttgc tggccttttg ctcacatgtt  10620

ctttcctgcg ttatcccctg attctgtgga taaccgtatt accgcctttg agtgagctga  10680

taccgctcgc cgcagccgaa cgaccgagcg cagcgagtca gtgagcgagg aagcggaaga  10740

gcgcccaata cgcaaaccgc ctctccccgc gcgttggccg attcattaat gcagctggca  10800

cgacaggttt cccgactgga aagcgggcag tgagcgcaac gcaattaatg tgagttagct  10860

cactcattag gcaccccagg ctttacactt tatgcttccg gctcgtatgt tgtgtggaat  10920

tgtgagcgga taacaatttc acacaggaaa cagctatgac catgattacg ccaagcgcgc  10980

aattaaccct cactaaaggg aacaaaagct ggagctgcaa gctt                  11024
```

<210> SEQ ID NO 10
<211> LENGTH: 5818
<212> TYPE: DNA
<213> ORGANISM: Artificial Sequence
<220> FEATURE:
<223> OTHER INFORMATION: Synthetic Construct

<400> SEQUENCE: 10

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagt    900

taagctatca acaagtttgt acaaaaaagc aggctccgcg gccgcccctt caccatggag    960

aaaaaaatca ctggatatac caccgttgat atatcccaat ggcatcgtaa agaacatttt   1020

gaggcatttc agtcagttgc tcaatgtacc tataaccaga ccgttcagct ggatattacg   1080

gcctttttaa agaccgtaaa gaaaaataag cacaagtttt atccggcctt tattcacatt   1140

cttgcccgcc tgatgaatgc tcatccggaa ttccgtatgg caatgaaaga cggtgagctg   1200
```

-continued

```
gtgatatggg atagtgttca cccttgttac accgttttcc atgagcaaac tgaaacgttt   1260
tcatcgctct ggagtgaata ccacgacgat ttccggcagt ttctacacat atattcgcaa   1320
gatgtggcgt gttacggtga aaacctggcc tatttcccta aagggtttat tgagaatatg   1380
tttttcgtct cagccaatcc ctgggtgagt ttcaccagtt ttgatttaaa cgtggccaat   1440
atggacaact tcttcgcccc cgttttcacc atgggcaaat attatacgca aggcgacaag   1500
gtgctgatgc cgctggcgat tcaggttcat catgccgtct gtgatggctt ccatgtcggc   1560
agaatgctta atgaattaca acagtactgc gatgagtggc agggcggggc gaagggtggg   1620
cgcgccgacc cagctttctt gtacaaagtg gttgatctag agggcccgcg gttcgaaggt   1680
aagcctatcc ctaaccctct cctcggtctc gattctacgc gtaccggtta gtaatgagtt   1740
taaacggggg aggctaactg aaacacggaa ggagacaata ccggaaggaa cccgcgctat   1800
gacggcaata aaaagacaga ataaaacgca cgggtgttgg gtcgtttgtt cataaacgcg   1860
gggttcggtc ccagggctgg cactctgtcg ataccccacc gagaccccat tggggccaat   1920
acgcccgcgt ttcttccttt tccccacccc accccccaag ttcgggtgaa ggcccagggc   1980
tcgcagccaa cgtcggggcg gcaggccctg ccatagcaga tctgcgcagc tggggctcta   2040
gggggtatcc ccacgcgccc tgtagcggcg cattaagcgc ggcgggtgtg gtggttacgc   2100
gcagcgtgac cgctacactt gccagcgccc tagcgcccgc tcctttcgct ttcttccctt   2160
cctttctcgc cacgttcgcc ggctttcccc gtcaagctct aaatcggggc atccctttag   2220
ggttccgatt tagtgcttta cggcacctcg accccaaaaa acttgattag ggtgatggtt   2280
cacgtagtgg gccatcgccc tgatagacgg tttttcgccc tttgacgttg gagtccacgt   2340
tctttaatag tggactcttg ttccaaactg gaacaacact caaccctatc tcggtctatt   2400
cttttgattt ataagggatt ttggggattt cggcctattg gttaaaaaat gagctgattt   2460
aacaaaaatt taacgcgaat taattctgtg gaatgtgtgt cagttagggt gtggaaagtc   2520
cccaggctcc ccagcaggca gaagtatgca aagcatgcat ctcaattagt cagcaaccag   2580
gtgtggaaag tccccaggct ccccagcagg cagaagtatg caaagcatgc atctcaatta   2640
gtcagcaacc atagtcccgc ccctaactcc gcccatcccg cccctaactc cgcccagttc   2700
cgcccattct ccgccccatg gctgactaat tttttttatt tatgcagagg ccgaggccgc   2760
ctctgcctct gagctattcc agaagtagtg aggaggcttt tttggaggcc taggcttttg   2820
caaaaagctc ccgggagctt gtatatccat tttcggatct gatcagcacg tgttgacaat   2880
taatcatcgg catagtatat cggcatagta taatacgaca aggtgaggaa ctaaaccatg   2940
gccaagcctt tgtctcaaga agaatccacc ctcattgaaa gagcaacggc tacaatcaac   3000
agcatcccca tctctgaaga ctacagcgtc gccagcgcag ctctctctag cgacggccgc   3060
atcttcactg gtgtcaatgt atatcatttt actgggggac cttgtgcaga actcgtggtg   3120
ctgggcactg ctgctgctgc ggcagctggc aacctgactt gtatcgtcgc gatcggaaat   3180
gagaacaggg gcatcttgag cccctgcgga cggtgccgac aggtgcttct cgatctgcat   3240
cctgggatca aagccatagt gaaggacagt gatggacagc cgacggcagt tgggattcgt   3300
gaattgctgc cctctggtta tgtgtgggag ggctaagcac ttcgtggccg aggagcagga   3360
ctgacacgtg ctacgagatt tcgattccac cgccgccttc tatgaaaggt tgggcttcgg   3420
aatcgttttc cgggacgccg gctggatgat cctccagcgc ggggatctca tgctggagtt   3480
cttcgcccac cccaacttgt ttattgcagc ttataatggt tacaaataaa gcaatagcat   3540
cacaaatttc acaaataaag catttttttc actgcattct agttgtggtt tgtccaaact   3600
```

-continued

```
catcaatgta tcttatcatg tctgtatacc gtcgacctct agctagagct tggcgtaatc   3660
atggtcatag ctgtttcctg tgtgaaattg ttatccgctc acaattccac acaacatacg   3720
agccggaagc ataaagtgta aagcctgggg tgcctaatga gtgagctaac tcacattaat   3780
tgcgttgcgc tcactgcccg ctttccagtc gggaaacctg tcgtgccagc tgcattaatg   3840
aatcggccaa cgcgcgggga gaggcggttt gcgtattggg cgctcttccg cttcctcgct   3900
cactgactcg ctgcgctcgg tcgttcggct gcggcgagcg gtatcagctc actcaaaggc   3960
ggtaatacgg ttatccacag aatcagggga taacgcagga aagaacatgt gagcaaaagg   4020
ccagcaaaag gccaggaacc gtaaaaaggc cgcgttgctg gcgtttttcc ataggctccg   4080
cccccctgac gagcatcaca aaaatcgacg ctcaagtcag aggtggcgaa acccgacagg   4140
actataaaga taccaggcgt ttccccctgg aagctccctc gtgcgctctc ctgttccgac   4200
cctgccgctt accggatacc tgtccgcctt tctcccttcg ggaagcgtgg cgctttctca   4260
tagctcacgc tgtaggtatc tcagttcggt gtaggtcgtt cgctccaagc tgggctgtgt   4320
gcacgaaccc cccgttcagc ccgaccgctg cgccttatcc ggtaactatc gtcttgagtc   4380
caacccggta agacacgact tatcgccact ggcagcagcc actggtaaca ggattagcag   4440
agcgaggtat gtaggcggtg ctacagagtt cttgaagtgg tggcctaact acggctacac   4500
tagaagaaca gtatttggta tctgcgctct gctgaagcca gttaccttcg gaaaaagagt   4560
tggtagctct tgatccggca aacaaaccac cgctggtagc ggtttttttg tttgcaagca   4620
gcagattacg cgcagaaaaa aaggatctca agaagatcct ttgatctttt ctacggggtc   4680
tgacgctcag tggaacgaaa actcacgtta agggattttg gtcatgagat tatcaaaaag   4740
gatcttcacc tagatccttt taaattaaaa atgaagtttt aaatcaatct aaagtatata   4800
tgagtaaact tggtctgaca gttaccaatg cttaatcagt gaggcaccta tctcagcgat   4860
ctgtctattt cgttcatcca tagttgcctg actccccgtc gtgtagataa ctacgatacg   4920
ggagggctta ccatctggcc ccagtgctgc aatgataccg cgagacccac gctcaccggc   4980
tccagattta tcagcaataa accagccagc cggaagggcc gagcgcagaa gtggtcctgc   5040
aactttatcc gcctccatcc agtctattaa ttgttgccgg gaagctagag taagtagttc   5100
gccagttaat agtttgcgca acgttgttgc cattgctaca ggcatcgtgg tgtcacgctc   5160
gtcgtttggt atggcttcat tcagctccgg ttcccaacga tcaaggcgag ttacatgatc   5220
ccccatgttg tgcaaaaaag cggttagctc cttcggtcct ccgatcgttg tcagaagtaa   5280
gttggccgca gtgttatcac tcatggttat ggcagcactg cataattctc ttactgtcat   5340
gccatccgta agatgctttt ctgtgactgg tgagtactca accaagtcat tctgagaata   5400
gtgtatgcgg cgaccgagtt gctcttgccc ggcgtcaata cgggataata ccgcgccaca   5460
tagcagaact ttaaaagtgc tcatcattgg aaaacgttct tcggggcgaa aactctcaag   5520
gatcttaccg ctgttgagat ccagttcgat gtaacccact cgtgcaccca actgatcttc   5580
agcatctttt actttcacca gcgtttctgg gtgagcaaaa acaggaaggc aaaatgccgc   5640
aaaaaaggga ataagggcga cacggaaatg ttgaatactc atactcttcc tttttcaata   5700
ttattgaagc atttatcagg gttattgtct catgagcgga tacatatttg aatgtattta   5760
gaaaaataaa caaatagggg ttccgcgcac atttccccga aaagtgccac ctgacgtc     5818
```

<210> SEQ ID NO 11
<211> LENGTH: 4761
<212> TYPE: DNA

<213> ORGANISM: Artificial Sequence
<220> FEATURE:
<223> OTHER INFORMATION: Synthetic Construct

<400> SEQUENCE: 11
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agctgaacga gaaacgtaaa atgatataaa tatcaatata ttaaattaga ttttgcataa 720
aaaacagact acataatact gtaaaacaca acatatccag tcactatgaa tcaactactt 780
agatggtatt agtgacctgt agtcgaccga cagccttcca aatgttcttc gggtgatgct 840
gccaacttag tcgaccgaca gccttccaaa tgttcttctc aaacggaatc gtcgtatcca 900
gcctactcgc tattgtcctc aatgccgtat taaatcataa aaagaaataa gaaaaagagg 960
tgcgagcctc ttttttgtgt gacaaaataa aaacatctac ctattcatat acgctagtgt 1020
catagtcctg aaaatcatct gcatcaagaa caatttcaca actcttatac ttttctctta 1080
caagtcgttc ggcttcatct ggattttcag cctctatact tactaaacgt gataaagttt 1140
ctgtaatttc tactgtatcg acctgcagac tggctgtgta taagggagcc tgacatttat 1200
attccccaga acatcaggtt aatggcgttt ttgatgtcat tttcgcggtg gctgagatca 1260
gccacttctt ccccgataac ggagaccggc acactggcca tatcggtggt catcatgcgc 1320
cagctttcat ccccgatatg caccaccggg taaagttcac gggagacttt atctgacagc 1380
agacgtgcac tggccagggg gatcaccatc cgtcgcccgg gcgtgtcaat aatatcactc 1440
tgtacatcca caaacagacg ataacggctc tctcttttat aggtgtaaac cttaaactgc 1500
atttcaccag cccctgttct cgtcagcaaa agagccgttc atttcaataa accgggcgac 1560
ctcagccatc ccttcctgat ttccgcttt ccagcgttcg gcacgcagac gacgggcttc 1620
attctgcatg gttgtgctta ccagaccgga gatattgaca tcatatatgc cttgagcaac 1680
tgatagctgt cgctgtcaac tgtcactgta atacgctgct tcatagcata cctctttttg 1740
acatacttcg ggtatacata tcagtatata ttcttatacc gcaaaaatca gcgcgcaaat 1800
acgcatactg ttatctggct tttagtaagc cggatccacg cggcgtttac gcccccccctg 1860 ccactcatcg cagtactgtt gtaattcatt aagcattctg ccgacatgga agccatcaca 1920
aacggcatga tgaacctgaa tcgccagcgg catcagcacc ttgtcgcctt gcgtataata 1980
tttgcccatg gtgaaaacgg gggcgaagaa gttgtccata ttggccacgt ttaaatcaaa 2040
actggtgaaa ctcacccagg gattggctga gacgaaaaac atattctcaa taaacccttt 2100
agggaaatag gccaggtttt caccgtaaca cgccacatct tgcgaatata tgtgtagaaa 2160
ctgccggaaa tcgtcgtggt attcactcca gagcgatgaa aacgtttcag tttgctcatg 2220

-continued

```
gaaaacggtg taacaagggt gaacactatc ccatatcacc agctcaccgt ctttcattgc   2280
catacggaat tccggatgag cattcatcag gcgggcaaga atgtgaataa aggccggata   2340
aaacttgtgc ttatttttct ttacggtctt taaaaaggcc gtaatatcca gctgaacggt   2400
ctggttatag gtacattgag caactgactg aaatgcctca aaatgttctt tacgatgcca   2460
ttgggatata tcaacggtgg tatatccagt gatttttttc tccattttag cttccttagc   2520
tcctgaaaat ctcgataact caaaaaatac gcccggtagt gatcttattt cattatggtg   2580
aaagttggaa cctcttacgt gccgatcaac gtctcatttt cgccaaaagt tggcccaggg   2640
cttcccggta tcaacaggga caccaggatt tatttattct gcgaagtgat cttccgtcac   2700
aggtatttat tcggcgcaaa gtgcgtcggg tgatgctgcc aacttagtcg actacaggtc   2760
actaatacca tctaagtagt tgattcatag tgactggata tgttgtgttt tacagtatta   2820
tgtagtctgt tttttatgca aaatctaatt taatatattg atatttatat cattttacgt   2880
ttctcgttca gctttcttgt acaaagttgg cattataaga aagcattgct tatcaatttg   2940
ttgcaacgaa caggtcacta tcagtcaaaa taaaatcatt atttgccatc cagctgatat   3000
cccctatagt gagtcgtatt acatggtcat agctgtttcc tggcagctct ggcccgtgtc   3060
tcaaaatctc tgatgttaca ttgcacaaga taaaaatata tcatcatgaa caataaaact   3120
gtctgcttac ataaacagta atacaagggg tgttatgagc catattcaac gggaaacgtc   3180
gaggccgcga ttaaattcca acatggatgc tgatttatat gggtataaat gggctcgcga   3240
taatgtcggg caatcaggtg cgacaatcta tcgcttgtat gggaagcccg atgcgccaga   3300
gttgtttctg aaacatggca aaggtagcgt tgccaatgat gttacagatg agatggtcag   3360
actaaactgg ctgacggaat ttatgcctct tccgaccatc aagcatttta tccgtactcc   3420
tgatgatgca tggttactca ccactgcgat ccccggaaaa acagcattcc aggtattaga   3480
agaatatcct gattcaggtg aaaatattgt tgatgcgctg gcagtgttcc tgcgccggtt   3540
gcattcgatt cctgtttgta attgtccttt taacagcgat cgcgtatttc gtctcgctca   3600
ggcgcaatca cgaatgaata acggtttggt tgatgcgagt gattttgatg acgagcgtaa   3660
tggctggcct gttgaacaag tctggaaaga aatgcataaa cttttgccat tctcaccgga   3720
ttcagtcgtc actcatggtg atttctcact tgataacctt atttttgacg aggggaaatt   3780
aataggttgt attgatgttg gacgagtcgg aatcgcagac cgataccagg atcttgccat   3840
cctatggaac tgcctcggtg agttttctcc ttcattacag aaacggcttt ttcaaaaata   3900
tggtattgat aatcctgata tgaataaatt gcagtttcat ttgatgctcg atgagttttt   3960
ctaatcagaa ttggttaatt ggttgtaaca ctggcagagc attacgctga cttgacggga   4020
cggcgcaagc tcatgaccaa aatcccttaa cgtgagttac gcgtcgttcc actgagcgtc   4080
agaccccgta gaaaagatca aaggatcttc ttgagatcct ttttttctgc gcgtaatctg   4140
ctgcttgcaa acaaaaaaac caccgctacc agcggtggtt tgtttgccgg atcaagagct   4200
accaactctt tttccgaagg taactggctt cagcagagcg cagataccaa atactgttct   4260
tctagtgtag ccgtagttag gccaccactt caagaactct gtagcaccgc ctacatacct   4320
cgctctgcta atcctgttac cagtggctgc tgccagtggc gataagtcgt gtcttaccgg   4380
gttggactca agacgatagt taccggataa ggcgcagcgg tcgggctgaa cggggggttc   4440
gtgcacacag cccagcttgg agcgaacgac ctacaccgaa ctgagatacc tacagcgtga   4500
gctatgagaa agcgccacgc ttcccgaagg gagaaaggcg gacaggtatc cggtaagcgg   4560
```

cagggtcgga acaggagagc gcacgaggga gcttccaggg ggaaacgcct ggtatcttta 4620
tagtcctgtc gggtttcgcc acctctgact tgagcgtcga tttttgtgat gctcgtcagg 4680
ggggcggagc ctatggaaaa acgccagcaa cgcggccttt ttacggttcc tggccttttg 4740
ctggcctttt gctcacatgt t 4761

<210> SEQ ID NO 12
<211> LENGTH: 2580
<212> TYPE: DNA
<213> ORGANISM: Artificial Sequence
<220> FEATURE:
<223> OTHER INFORMATION: Synthetic Construct

<400> SEQUENCE: 12
ctttcctgcg ttatcccctg attctgtgga taaccgtatt accgcctttg agtgagctga 60
taccgctcgc cgcagccgaa cgaccgagcg cagcgagtca gtgagcgagg aagcggaaga 120
gcgcccaata cgcaaaccgc ctctccccgc gcgttggccg attcattaat gcagctggca 180
cgacaggttt cccgactgga aagcgggcag tgagcgcaac gcaattaata cgcgtaccgc 240
tagccaggaa gagtttgtag aaacgcaaaa aggccatccg tcaggatggc cttctgctta 300
gtttgatgcc tggcagttta tggcgggcgt cctgcccgcc accctccggg ccgttgcttc 360
acaacgttca aatccgctcc cggcggattt gtcctactca ggagagcgtt caccgacaaa 420
caacagataa aacgaaaggc ccagtcttcc gactgagcct ttcgttttat ttgatgcctg 480
gcagttccct actctcgcgt taacgctagc atggatgttt tcccagtcac gacgttgtaa 540
aacgacggcc agtcttaagc tcgggcccca aataatgatt ttattttgac tgatagtgac 600
ctgttcgttg caacaaattg atgagcaatg cttttttata atgccaactt tgtacaaaaa 660
agcaggctcc gcggccgccc ccttcaccaa gggtgggcgc gccgacccag ctttcttgta 720
caaagttggc attataagaa agcattgctt atcaatttgt tgcaacgaac aggtcactat 780
cagtcaaaat aaaatcatta tttgccatcc agctgatatc ccctatagtg agtcgtatta 840
catggtcata gctgtttcct ggcagctctg gcccgtgtct caaaatctct gatgttacat 900
tgcacaagat aaaaatatat catcatgaac aataaaactg tctgcttaca taaacagtaa 960
tacaaggggt gttatgagcc atattcaacg ggaaacgtcg aggccgcgat taaattccaa 1020
catggatgct gatttatatg ggtataaatg ggctcgcgat aatgtcgggc aatcaggtgc 1080
gacaatctat cgcttgtatg ggaagcccga tgcgccagag ttgtttctga aacatggcaa 1140
aggtagcgtt gccaatgatg ttacagatga gatggtcaga ctaaactggc tgacggaatt 1200
tatgcctctt ccgaccatca agcattttat ccgtactcct gatgatgcat ggttactcac 1260
cactgcgatc cccggaaaaa cagcattcca ggtattagaa gaatatcctg attcaggtga 1320
aaatattgtt gatgcgctgg cagtgttcct gcgccggttg cattcgattc ctgtttgtaa 1380
ttgtcctttt aacagcgatc gcgtatttcg tctcgctcag gcgcaatcac gaatgaataa 1440
cggtttggtt gatgcgagtg attttgatga cgagcgtaat ggctggcctg ttgaacaagt 1500
ctggaaagaa atgcataaac ttttgccatt ctcaccggat tcagtcgtca ctcatggtga 1560
tttctcactt gataacctta tttttgacga ggggaaatta ataggttgta ttgatgttgg 1620
acgagtcgga atcgcagacc gataccagga tcttgccatc ctatggaact gcctcggtga 1680
gttttctcct tcattacaga aacggctttt tcaaaaatat ggtattgata atcctgatat 1740
gaataaattg cagtttcatt tgatgctcga tgagtttttc taatcagaat tggttaattg 1800
gttgtaacac tggcagagca ttacgctgac ttgacgggac ggcgcaagct catgaccaaa 1860

```
atcccttaac gtgagttacg cgtcgttcca ctgagcgtca gaccccgtag aaaagatcaa   1920

aggatcttct tgagatcctt tttttctgcg cgtaatctgc tgcttgcaaa caaaaaaacc   1980

accgctacca gcggtggttt gtttgccgga tcaagagcta ccaactcttt ttccgaaggt   2040

aactggcttc agcagagcgc agataccaaa tactgtcctt ctagtgtagc cgtagttagg   2100

ccaccacttc aagaactctg tagcaccgcc tacatacctc gctctgctaa tcctgttacc   2160

agtggctgct gccagtggcg ataagtcgtg tcttaccggg ttggactcaa gacgatagtt   2220

accggataag gcgcagcggt cgggctgaac ggggggttcg tgcacacagc ccagcttgga   2280

gcgaacgacc tacaccgaac tgagatacct acagcgtgag cattgagaaa gcgccacgct   2340

tcccgaaggg agaaaggcgg acaggtatcc ggtaagcggc agggtcggaa caggagagcg   2400

cacgagggag cttccagggg gaaacgcctg gtatctttat agtcctgtcg ggtttcgcca   2460

cctctgactt gagcgtcgat ttttgtgatg ctcgtcaggg gggcggagcc tatggaaaaa   2520

cgccagcaac gcggcctttt tacggttcct ggccttttgc tggccttttg ctcacatgtt   2580
```

<210> SEQ ID NO 13
<211> LENGTH: 16
<212> TYPE: PRT
<213> ORGANISM: Homo sapiens

<400> SEQUENCE: 13

```
Cys Thr Asn Gln Ala Thr Arg Pro Pro Gly Gly Ser His Thr Asp Glu
1               5                   10                  15
```

<210> SEQ ID NO 14
<211> LENGTH: 15
<212> TYPE: PRT
<213> ORGANISM: Homo sapiens

<400> SEQUENCE: 14

```
Asp Ser Ser Asp Glu Lys Ser Ser Glu Gly Val Thr His Val Cys
1               5                   10                  15
```

<210> SEQ ID NO 15
<211> LENGTH: 14
<212> TYPE: PRT
<213> ORGANISM: Homo sapiens

<400> SEQUENCE: 15

```
Gly Asp Asn Asp Ser Glu Asp Asn Ser Asp Glu Glu Asn Cys
1               5                   10
```

<210> SEQ ID NO 16
<211> LENGTH: 5004
<212> TYPE: DNA
<213> ORGANISM: Artificial Sequence
<220> FEATURE:
<223> OTHER INFORMATION: Synthetic Construct

<400> SEQUENCE: 16

```
gttgacattg attattgact agttattaat agtaatcaat tacggggtca ttagttcata     60

gcccatatat ggagttccgc gttacataac ttacggtaaa tggcccgcct ggctgaccgc    120

ccaacgaccc ccgcccattg acgtcaataa tgacgtatgt tcccatagta acgccaatag    180

ggactttcca ttgacgtcaa tgggtggagt atttacggta aactgcccac ttggcagtac    240

atcaagtgta tcatatgcca agtacgcccc ctattgacgt caatgacggt aaatggcccg    300

cctggcatta tgcccagtac atgaccttat gggactttcc tacttggcag tacatctacg    360
```

-continued

```
tattagtcat cgctattacc atggtgatgc ggttttggca gtacatcaat gggcgtggat    420
agcggtttga ctcacgggga tttccaagtc tccaccccat tgacgtcaat gggagtttgt    480
tttggcacca aaatcaacgg gactttccaa aatgtcgtaa caactccgcc ccattgacgc    540
aaatgggcgg taggcgtgta cggtgggagg tctatataag cagagctctc tggctaacta    600
gagaacccac tgcttactgg cttatcgaaa ttaatacgac tcactatagg gagtcccaag    660
ctggctagtt aagctatcaa caagtttgta caaaaaagca ggctttaaag ggaggtagtg    720
agtcgaccag tggatcctgg aggcttgctg aaggctgtat gctgcataca cgaggaacag    780
ctcatgtttt ggccactgac tgacatgagc tgcctcgtgt atgcaggaca caaggcctgt    840
tactagcact cacatggaac aaatggccca gatctggccg cactcgagat atctagaccc    900
agctttcttg tacaaagtgg ttgatctaga gggcccgcgg ttcgctgatg gggaggcta     960
actgaaacac ggaaggagac aataccggaa ggaacccgcg ctatgacggc aataaaaaga   1020
cagaataaaa cgcacgggtg ttgggtcgtt tgttcataaa cgcggggttc ggtcccaggg   1080
ctggcactct gtcgataccc caccgtgacc ccattggggc caatacgccc gcgtttcttc   1140
cttttcccca ccccaccccc caagttcggg tgaaggccca gggctcgcag ccaacgtcgg   1200
ggcggcaggc cctgccatag catcccctat agtgagtcgt attacatggt catagctgtt   1260
tcctggcagc tctggcccgt gtctcaaaat ctctgatgga tctgcgcagc tggggctcta   1320
gggggtatcc ccacgcgccc tgtagcggcg cattaagcgc ggcgggtgtg gtggttacgc   1380
gcagcgtgac cgctacactt gccagcgccc tagcgcccgc tcctttcgct ttcttccctt   1440
cctttctcgc cacgttcgcc ggctttcccc gtcaagctct aaatcggggg ctccctttag   1500
ggttccgatt tagtgcttta cggcacctcg accccaaaaa acttgattag ggtgatggtt   1560
cacgtagtgg gccatcgccc tgatagacgg tttttcgccc tttgacgttg gagtccacgt   1620
tctttaatag tggactcttg ttccaaactg gaacaacact caaccctatc tcggtctatt   1680
cttttgattt ataagggatt ttgccgattt cggcctattg gttaaaaaat gagctgattt   1740
aacaaaaatt taacgcgaat taattctgtg gaatgtgtgt cagttagggt gtggaaagtc   1800
cccaggctcc ccagcaggca gaagtatgca aagcatgcat ctcaattagt cagcaaccag   1860
gtgtggaaag tccccaggct ccccagcagg cagaagtatg caaagcatgc atctcaatta   1920
gtcagcaacc atagtcccgc ccctaactcc gcccatcccg cccctaactc cgcccagttc   1980
cgcccattct ccgccccatg gctgactaat tttttttatt tatgcagagg ccgaggccgc   2040
ctctgcctct gagctattcc agaagtagtg aggaggcttt tttggaggcc taggcttttg   2100
caaaaagctc ccgggagctt gtatatccat tttcggatct gatcagcacg tgttgacaat   2160
taatcatcgg catagtatat cggcatagta taatacgaca aggtgaggaa ctaaaccatg   2220
gccaagcctt tgtctcaaga agaatccacc ctcattgaaa gagcaacggc tacaatcaac   2280
agcatcccca tctctgaaga ctacagcgtc gccagcgcag ctctctctag cgacggccgc   2340
atcttcactg gtgtcaatgt atatcatttt actgggggac cttgtgcaga actcgtggtg   2400
ctgggcactg ctgctgctgc ggcagctggc aacctgactt gtatcgtcgc gatcggaaat   2460
gagaacaggg gcatcttgag cccctgcgga cggtgccgac aggtgcttct cgatctgcat   2520
cctgggatca aagccatagt gaaggacagt gatggacagc cgacggcagt tgggattcgt   2580
gaattgctgc cctctggtta tgtgtgggag ggctaagcac ttcgtggccg aggagcagga   2640
ctgacacgtg ctacgagatt tcgattccac cgccgccttc tatgaaaggt tgggcttcgg   2700
```

-continued

```
aatcgttttc cgggacgccg gctggatgat cctccagcgc ggggatctca tgctggagtt   2760
cttcgcccac cccaacttgt ttattgcagc ttataatggt tacaaataaa gcaatagcat   2820
cacaaatttc acaaataaag catttttttc actgcattct agttgtggtt tgtccaaact   2880
catcaatgta tcttatcatg tctgtatacc gtcgctcttc cgctgcttcc tcgctcactg   2940
actcgctgcg ctcggtcgtt cggctgcggc gagcggtatc agctcactca aaggcggtaa   3000
tacggttatc cacagaatca ggggataacg caggaaagaa catgtgagca aaaggccagc   3060
aaaaggccag gaaccgtaaa aaggccgcgt tgctggcgtt tttccatagg ctccgccccc   3120
ctgacgagca tcacaaaaat cgacgctcaa gtcagaggtg gcgaaacccg acaggactat   3180
aaagatacca ggcgtttccc cctggaagct ccctcgtgcg ctctcctgtt ccgaccctgc   3240
cgcttaccgg atacctgtcc gcctttctcc cttcgggaag cgtggcgctt tctcatagct   3300
cacgctgtag gtatctcagt tcggtgtagg tcgttcgctc caagctgggc tgtgtgcacg   3360
aaccccccgt tcagcccgac cgctgcgcct tatccggtaa ctatcgtctt gagtccaacc   3420
cggtaagaca cgacttatcg ccactggcag cagccactgg taacaggatt agcagagcga   3480
ggtatgtagg cggtgctaca gagttcttga agtggtggcc taactacggc tacactagaa   3540
gaacagtatt tggtatctgc gctctgctga agccagttac cttcggaaaa agagttggta   3600
gctcttgatc cggcaaacaa accaccgctg gtagcggtgg tttttttgtt tgcaagcagc   3660
agattacgcg cagaaaaaaa ggatctcaag aagatccttt gatcttttct acggggtctg   3720
acgctcagtg gaacgacgcg taactcacgt taagggattt tggtcatggg tggctcgacg   3780
agggttattt gccgactacc ttggtgatct cgcctttcac gtagtggaca aattcttcca   3840
actgatctgc gcgcgaggcc aagcgatctt cttcttgtcc aagataagcc tgtctagctt   3900
caagtatgac gggctgatac tgggccggca ggcgctccat tgcccagtcg gcagcgacat   3960
ccttcggcgc gattttgccg gttactgcgc tgtaccaaat gcgggacaac gtaagcacta   4020
catttcgctc atcgccagcc cagtcgggcg gcgagttcca tagcgttaag gtttcattta   4080
gcgcctcaaa tagatcctgt tcaggaaccg gatcaaagag ttcctccgcc gctggaccta   4140
ccaaggcaac gctatgttct cttgcttttg tcagcaagat agccagatca atgtcgatcg   4200
tggctggctc gaagatacct gcaagaatgt cattgcgctg ccattctcca aattgcagtt   4260
cgcgcttagc tggataacgc cacggaatga tgtcgtcgtg cacaacaatg gtgacttcta   4320
cagcgcggag aatctcgctc tctccagggg aagccgaagt ttccaaaagg tcgttgatca   4380
aagctcgccg cgttgtttca tcaagcctta cggtcaccgt aaccagcaaa tcaatatcac   4440
tgtgtggctt caggccgcca tccactgcgg agccgtacaa atgtacggcc agcaacgtcg   4500
gttcgagatg gcgctcgatg acgccaacta cctctgatag ttgagtcgat acttcggcga   4560
tcaccgcttc cctcataatg tttaactttg ttttagggcg actgccctgc tgcgtaacat   4620
cgttgctgct ccataacatc aaacatcgac ccacggcgta acgcgcttgc tgcttggatg   4680
cccgaggcat agactgtacc ccaaaaaaac agtcataaca agccatgaaa accgccactg   4740
cgccgttacc accgctgcgt tcggtcaagg ttctggacca gttgcgtgag cgcatacgct   4800
acttgcatta cagcttacga accgaacagg cttatgtcca ctgggttcgt gccttcatcc   4860
gtttccacgg tgtgcgtcac ccggcaacct tgggtagcag cgaagtcgag gcatttctgt   4920
cctggctggt ctagaattgc atgaagaatc tgcttagggt taggcgtttt gcgctgcttc   4980
gcgatgtacg ggccagatat acgc                                           5004
```

-continued

<210> SEQ ID NO 17
<211> LENGTH: 5004
<212> TYPE: DNA
<213> ORGANISM: Artificial Sequence
<220> FEATURE:
<223> OTHER INFORMATION: Synthetic Construct

<400> SEQUENCE: 17
gttgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600
gagaacccac tgcttactgg cttatcgaaa ttaatacgac tcactatagg gagtcccaag 660
ctggctagtt aagctatcaa caagtttgta caaaaaagca ggctttaaag ggaggtagtg 720
agtcgaccag tggatcctgg aggcttgctg aaggctgtat gctgtcctca caatccacaa 780
actgggtttt ggccactgac tgacccagtt tggattgtga ggacaggaca caaggcctgt 840
tactagcact cacatggaac aaatggccca gatctggccg cactcgagat atctagaccc 900
agctttcttg tacaaagtgg ttgatctaga gggcccgcgg ttcgctgatg ggggaggcta 960
actgaaacac ggaaggagac aataccggaa ggaacccgcg ctatgacggc aataaaaaga 1020
cagaataaaa cgcacgggtg ttgggtcgtt tgttcataaa cgcggggttc ggtcccaggg 1080
ctggcactct gtcgataccc caccgtgacc ccattggggc caatacgccc gcgtttcttc 1140
cttttcccca ccccaccccc caagttcggg tgaaggccca gggctcgcag ccaacgtcgg 1200
ggcggcaggc cctgccatag catcccctat agtgagtcgt attacatggt catagctgtt 1260
tcctggcagc tctggcccgt gtctcaaaat ctctgatgga tctgcgcagc tggggctcta 1320
gggggtatcc ccacgcgccc tgtagcggcg cattaagcgc ggcgggtgtg gtggttacgc 1380
gcagcgtgac cgctacactt gccagcgccc tagcgcccgc tcctttcgct ttcttccctt 1440
cctttctcgc cacgttcgcc ggctttcccc gtcaagctct aaatcggggg ctccctttag 1500
ggttccgatt tagtgcttta cggcacctcg accccaaaaa acttgattag ggtgatggtt 1560
cacgtagtgg gccatcgccc tgatagacgg tttttcgccc tttgacgttg gagtccacgt 1620
tctttaatag tggactcttg ttccaaactg gaacaacact caaccctatc tcggtctatt 1680
cttttgattt ataagggatt ttgccgattt cggcctattg gttaaaaaat gagctgattt 1740
aacaaaaatt taacgcgaat taattctgtg gaatgtgtgt cagttagggt gtggaaagtc 1800
cccaggctcc ccagcaggca gaagtatgca aagcatgcat ctcaattagt cagcaaccag 1860
gtgtggaaag tccccaggct ccccagcagg cagaagtatg caaagcatgc atctcaatta 1920
gtcagcaacc atagtcccgc ccctaactcc gcccatcccg cccctaactc cgcccagttc 1980
cgcccattct ccgccccatg gctgactaat tttttttatt tatgcagagg ccgaggccgc 2040
ctctgcctct gagctattcc agaagtagtg aggaggcttt tttggaggcc taggcttttg 2100

-continued

```
caaaaagctc ccgggagctt gtatatccat tttcggatct gatcagcacg tgttgacaat   2160
taatcatcgg catagtatat cggcatagta taatacgaca aggtgaggaa ctaaaccatg   2220
gccaagcctt tgtctcaaga agaatccacc ctcattgaaa gagcaacggc tacaatcaac   2280
agcatcccca tctctgaaga ctacagcgtc gccagcgcag ctctctctag cgacggccgc   2340
atcttcactg gtgtcaatgt atatcatttt actgggggac cttgtgcaga actcgtggtg   2400
ctgggcactg ctgctgctgc ggcagctggc aacctgactt gtatcgtcgc gatcggaaat   2460
gagaacaggg gcatcttgag cccctgcgga cggtgccgac aggtgcttct cgatctgcat   2520
cctgggatca aagccatagt gaaggacagt gatggacagc cgacggcagt tgggattcgt   2580
gaattgctgc cctctggtta tgtgtgggag ggctaagcac ttcgtggccg aggagcagga   2640
ctgacacgtg ctacgagatt tcgattccac cgccgccttc tatgaaaggt tgggcttcgg   2700
aatcgttttc cgggacgccg gctggatgat cctccagcgc ggggatctca tgctggagtt   2760
cttcgcccac cccaacttgt ttattgcagc ttataatggt tacaaataaa gcaatagcat   2820
cacaaatttc acaaataaag catttttttc actgcattct agttgtggtt tgtccaaact   2880
catcaatgta tcttatcatg tctgtatacc gtcgctcttc cgctgcttcc tcgctcactg   2940
actcgctgcg ctcggtcgtt cggctgcggc gagcggtatc agctcactca aaggcggtaa   3000
tacggttatc cacagaatca ggggataacg caggaaagaa catgtgagca aaaggccagc   3060
aaaaggccag gaaccgtaaa aaggccgcgt tgctggcgtt tttccatagg ctccgccccc   3120
ctgacgagca tcacaaaaat cgacgctcaa gtcagaggtg gcgaaacccg acaggactat   3180
aaagatacca ggcgtttccc cctggaagct ccctcgtgcg ctctcctgtt ccgaccctgc   3240
cgcttaccgg atacctgtcc gcctttctcc cttcgggaag cgtggcgctt tctcatagct   3300
cacgctgtag gtatctcagt tcggtgtagg tcgttcgctc caagctgggc tgtgtgcacg   3360
aaccccccgt tcagcccgac cgctgcgcct tatccggtaa ctatcgtctt gagtccaacc   3420
cggtaagaca cgacttatcg ccactggcag cagccactgg taacaggatt agcagagcga   3480
ggtatgtagg cggtgctaca gagttcttga agtggtggcc taactacggc tacactagaa   3540
gaacagtatt tggtatctgc gctctgctga agccagttac cttcggaaaa agagttggta   3600
gctcttgatc cggcaaacaa accaccgctg gtagcggtgg tttttttgtt tgcaagcagc   3660
agattacgcg cagaaaaaaa ggatctcaag aagatccttt gatcttttct acggggtctg   3720
acgctcagtg gaacgacgcg taactcacgt taagggattt tggtcatggg tggctcgacg   3780
agggttattt gccgactacc ttggtgatct cgcctttcac gtagtggaca aattcttcca   3840
actgatctgc gcgcgaggcc aagcgatctt cttcttgtcc aagataagcc tgtctagctt   3900
caagtatgac gggctgatac tgggccggca ggcgctccat tgcccagtcg gcagcgacat   3960
ccttcggcgc gattttgccg gttactgcgc tgtaccaaat gcgggacaac gtaagcacta   4020
catttcgctc atcgccagcc cagtcgggcg gcgagttcca tagcgttaag gtttcattta   4080
gcgcctcaaa tagatcctgt tcaggaaccg gatcaaagag ttcctccgcc gctggaccta   4140
ccaaggcaac gctatgttct cttgcttttg tcagcaagat agccagatca atgtcgatcg   4200
tggctggctc gaagatacct gcaagaatgt cattgcgctg ccattctcca aattgcagtt   4260
cgcgcttagc tggataacgc cacggaatga tgtcgtcgtg cacaacaatg gtgacttcta   4320
cagcgcggag aatctcgctc tctccagggg aagccgaagt ttccaaaagg tcgttgatca   4380
aagctcgccg cgttgtttca tcaagcctta cggtcaccgt aaccagcaaa tcaatatcac   4440
tgtgtggctt caggccgcca tccactgcgg agccgtacaa atgtacggcc agcaacgtcg   4500
```

-continued gttcgagatg gcgctcgatg acgccaacta cctctgatag ttgagtcgat acttcggcga 4560
tcaccgcttc cctcataatg tttaactttg ttttagggcg actgccctgc tgcgtaacat 4620
cgttgctgct ccataacatc aaacatcgac ccacggcgta acgcgcttgc tgcttggatg 4680
cccgaggcat agactgtacc ccaaaaaaac agtcataaca agccatgaaa accgccactg 4740
cgccgttacc accgctgcgt tcggtcaagg ttctggacca gttgcgtgag cgcatacgct 4800
acttgcatta cagcttacga accgaacagg cttatgtcca ctgggttcgt gccttcatcc 4860
gtttccacgg tgtgcgtcac ccggcaacct tgggtagcag cgaagtcgag gcatttctgt 4920
cctggctggt ctagaattgc atgaagaatc tgcttagggt taggcgtttt gcgctgcttc 4980
gcgatgtacg ggccagatat acgc 5004

<210> SEQ ID NO 18
<211> LENGTH: 5004
<212> TYPE: DNA
<213> ORGANISM: Artificial Sequence
<220> FEATURE:
<223> OTHER INFORMATION: Synthetic construct

<400> SEQUENCE: 18
gttgacattg attattgact agttattaat agtaatcaat tacggggtca ttagttcata 60
gcccatatat ggagttccgc gttacataac ttacggtaaa tggcccgcct ggctgaccgc 120
ccaacgaccc ccgcccattg acgtcaataa tgacgtatgt tcccatagta acgccaatag 180
ggactttcca ttgacgtcaa tgggtggagt atttacggta aactgcccac ttggcagtac 240
atcaagtgta tcatatgcca agtacgcccc ctattgacgt caatgacggt aaatggcccg 300
cctggcatta tgcccagtac atgaccttat gggactttcc tacttggcag tacatctacg 360
tattagtcat cgctattacc atggtgatgc ggttttggca gtacatcaat gggcgtggat 420
agcggtttga ctcacgggga tttccaagtc tccaccccat tgacgtcaat gggagtttgt 480
tttggcacca aaatcaacgg gactttccaa aatgtcgtaa caactccgcc ccattgacgc 540
aaatgggcgg taggcgtgta cggtgggagg tctatataag cagagctctc tggctaacta 600
gagaacccac tgcttactgg cttatcgaaa ttaatacgac tcactatagg gagtcccaag 660
ctggctagtt aagctatcaa caagtttgta caaaaaagca ggctttaaag ggaggtagtg 720
agtcgaccag tggatcctgg aggcttgctg aaggctgtat gctgagcaga acttgttgca 780
gtggggtttt ggccactgac tgaccccact gccaagttct gctcaggaca caaggcctgt 840
tactagcact cacatggaac aaatggccca gatctggccg cactcgagat atctagaccc 900
agctttcttg tacaaagtgg ttgatctaga gggcccgcgg ttcgctgatg ggggaggcta 960
actgaaacac ggaaggagac aataccggaa ggaacccgcg ctatgacggc aataaaaaga 1020
cagaataaaa cgcacgggtg ttgggtcgtt tgttcataaa cgcggggttc ggtcccaggg 1080
ctggcactct gtcgataccc caccgtgacc ccattggggc caatacgccc gcgtttcttc 1140
cttttcccca ccccaccccc caagttcggg tgaaggccca gggctcgcag ccaacgtcgg 1200
ggcggcaggc cctgccatag catcccctat agtgagtcgt attacatggt catagctgtt 1260
tcctggcagc tctggcccgt gtctcaaaat ctctgatgga tctgcgcagc tggggctcta 1320
gggggtatcc ccacgcgccc tgtagcggcg cattaagcgc ggcgggtgtg gtggttacgc 1380
gcagcgtgac cgctacactt gccagcgccc tagcgcccgc tcctttcgct ttcttccctt 1440
cctttctcgc cacgttcgcc ggctttcccc gtcaagctct aaatcggggg ctccctttag 1500

-continued

```
ggttccgatt tagtgcttta cggcacctcg accccaaaaa acttgattag ggtgatggtt   1560
cacgtagtgg gccatcgccc tgatagacgg tttttcgccc tttgacgttg gagtccacgt   1620
tctttaatag tggactcttg ttccaaactg gaacaacact caaccctatc tcggtctatt   1680
cttttgattt ataagggatt ttgccgattt cggcctattg gttaaaaaat gagctgattt   1740
aacaaaaatt taacgcgaat taattctgtg gaatgtgtgt cagttagggt gtggaaagtc   1800
cccaggctcc ccagcaggca gaagtatgca aagcatgcat ctcaattagt cagcaaccag   1860
gtgtggaaag tccccaggct ccccagcagg cagaagtatg caaagcatgc atctcaatta   1920
gtcagcaacc atagtcccgc ccctaactcc gcccatcccg cccctaactc cgcccagttc   1980
cgcccattct ccgccccatg gctgactaat tttttttatt tatgcagagg ccgaggccgc   2040
ctctgcctct gagctattcc agaagtagtg aggaggcttt tttggaggcc taggcttttg   2100
caaaaagctc ccgggagctt gtatatccat tttcggatct gatcagcacg tgttgacaat   2160
taatcatcgg catagtatat cggcatagta taatacgaca aggtgaggaa ctaaaccatg   2220
gccaagcctt tgtctcaaga agaatccacc ctcattgaaa gagcaacggc tacaatcaac   2280
agcatcccca tctctgaaga ctacagcgtc gccagcgcag ctctctctag cgacggccgc   2340
atcttcactg gtgtcaatgt atatcatttt actgggggac cttgtgcaga actcgtggtg   2400
ctgggcactg ctgctgctgc ggcagctggc aacctgactt gtatcgtcgc gatcggaaat   2460
gagaacaggg gcatcttgag cccctgcgga cggtgccgac aggtgcttct cgatctgcat   2520
cctgggatca aagccatagt gaaggacagt gatggacagc cgacggcagt tgggattcgt   2580
gaattgctgc cctctggtta tgtgtgggag ggctaagcac ttcgtggccg aggagcagga   2640
ctgacacgtg ctacgagatt tcgattccac cgccgccttc tatgaaaggt tgggcttcgg   2700
aatcgttttc cgggacgccg gctggatgat cctccagcgc ggggatctca tgctggagtt   2760
cttcgcccac cccaacttgt ttattgcagc ttataatggt tacaaataaa gcaatagcat   2820
cacaaatttc acaaataaag catttttttc actgcattct agttgtggtt tgtccaaact   2880
catcaatgta tcttatcatg tctgtatacc gtcgctcttc cgctgcttcc tcgctcactg   2940
actcgctgcg ctcggtcgtt cggctgcggc gagcggtatc agctcactca aaggcggtaa   3000
tacggttatc cacagaatca ggggataacg caggaaagaa catgtgagca aaaggccagc   3060
aaaaggccag gaaccgtaaa aaggccgcgt tgctggcgtt tttccatagg ctccgccccc   3120
ctgacgagca tcacaaaaat cgacgctcaa gtcagaggtg gcgaaacccg acaggactat   3180
aaagatacca ggcgtttccc cctggaagct ccctcgtgcg ctctcctgtt ccgaccctgc   3240
cgcttaccgg atacctgtcc gcctttctcc cttcgggaag cgtggcgctt tctcatagct   3300
cacgctgtag gtatctcagt tcggtgtagg tcgttcgctc caagctgggc tgtgtgcacg   3360
aaccccccgt tcagcccgac cgctgcgcct tatccggtaa ctatcgtctt gagtccaacc   3420
cggtaagaca cgacttatcg ccactggcag cagccactgg taacaggatt agcagagcga   3480
ggtatgtagg cggtgctaca gagttcttga agtggtggcc taactacggc tacactagaa   3540
gaacagtatt tggtatctgc gctctgctga agccagttac cttcggaaaa agagttggta   3600
gctcttgatc cggcaaacaa accaccgctg gtagcggtgg tttttttgtt tgcaagcagc   3660
agattacgcg cagaaaaaaa ggatctcaag aagatccttt gatcttttct acggggtctg   3720
acgctcagtg gaacgacgcg taactcacgt taagggattt tggtcatggg tggctcgacg   3780
agggttattt gccgactacc ttggtgatct cgcctttcac gtagtggaca aattcttcca   3840
actgatctgc gcgcgaggcc aagcgatctt cttcttgtcc aagataagcc tgtctagctt   3900
```

-continued

```
caagtatgac gggctgatac tgggccggca ggcgctccat tgcccagtcg gcagcgacat   3960

ccttcggcgc gattttgccg gttactgcgc tgtaccaaat gcgggacaac gtaagcacta   4020

catttcgctc atcgccagcc cagtcgggcg gcgagttcca tagcgttaag gtttcattta   4080

gcgcctcaaa tagatcctgt tcaggaaccg gatcaaagag ttcctccgcc gctggaccta   4140

ccaaggcaac gctatgttct cttgcttttg tcagcaagat agccagatca atgtcgatcg   4200

tggctggctc gaagatacct gcaagaatgt cattgcgctg ccattctcca aattgcagtt   4260

cgcgcttagc tggataacgc cacggaatga tgtcgtcgtg cacaacaatg gtgacttcta   4320

cagcgcggag aatctcgctc tctccagggg aagccgaagt ttccaaaagg tcgttgatca   4380

aagctcgccg cgttgtttca tcaagcctta cggtcaccgt aaccagcaaa tcaatatcac   4440

tgtgtggctt caggccgcca tccactgcgg agccgtacaa atgtacggcc agcaacgtcg   4500

gttcgagatg gcgctcgatg acgccaacta cctctgatag ttgagtcgat acttcggcga   4560

tcaccgcttc cctcataatg tttaactttg ttttagggcg actgccctgc tgcgtaacat   4620

cgttgctgct ccataacatc aaacatcgac ccacggcgta acgcgcttgc tgcttggatg   4680

cccgaggcat agactgtacc ccaaaaaaac agtcataaca agccatgaaa accgccactg   4740

cgccgttacc accgctgcgt tcggtcaagg ttctggacca gttgcgtgag cgcatacgct   4800

acttgcatta cagcttacga accgaacagg cttatgtcca ctgggttcgt gccttcatcc   4860

gtttccacgg tgtgcgtcac ccggcaacct tgggtagcag cgaagtcgag gcatttctgt   4920

cctggctggt ctagaattgc atgaagaatc tgcttagggt taggcgtttt gcgctgcttc   4980

gcgatgtacg ggccagatat acgc                                          5004
```

<210> SEQ ID NO 19
<211> LENGTH: 916
<212> TYPE: PRT
<213> ORGANISM: Homo sapiens

<400> SEQUENCE: 19

```
Tyr Leu Phe Trp Thr Glu Tyr Arg Ser Gly Ser Val Tyr Arg Leu Glu
1               5                   10                  15

Arg Gly Val Gly Gly Ala Pro Pro Thr Val Thr Leu Leu Arg Ser Glu
            20                  25                  30

Arg Pro Pro Ile Phe Glu Ile Arg Met Tyr Asp Ala Gln Gln Gln Gln
        35                  40                  45

Val Gly Thr Asn Lys Cys Arg Val Asn Asn Gly Gly Cys Ser Ser Leu
    50                  55                  60

Cys Leu Ala Thr Pro Gly Ser Arg Gln Cys Ala Cys Ala Glu Asp Gln
65                  70                  75                  80

Val Leu Asp Ala Asp Gly Val Thr Cys Leu Ala Asn Pro Ser Tyr Val
                85                  90                  95

Pro Pro Pro Gln Cys Gln Pro Gly Glu Phe Ala Cys Ala Asn Ser Arg
            100                 105                 110

Cys Ile Gln Glu Arg Trp Lys Cys Asp Gly Asp Asn Asp Cys Leu Asp
        115                 120                 125

Asn Ser Asp Glu Ala Pro Ala Leu Cys His Gln His Thr Cys Pro Ser
    130                 135                 140

Asp Arg Phe Lys Cys Glu Asn Asn Arg Cys Ile Pro Asn Arg Trp Leu
145                 150                 155                 160

Cys Asp Gly Asp Asn Asp Cys Gly Asn Ser Glu Asp Glu Ser Asn Ala
                165                 170                 175
```

-continued

```
Thr Cys Ser Ala Arg Thr Cys Pro Pro Asn Gln Phe Ser Cys Ala Ser
            180                 185                 190

Gly Arg Cys Ile Pro Ile Ser Trp Thr Cys Asp Leu Asp Asp Asp Cys
        195                 200                 205

Gly Asp Arg Ser Asp Glu Ser Ala Ser Cys Ala Tyr Pro Thr Cys Phe
    210                 215                 220

Pro Leu Thr Gln Phe Thr Cys Asn Asn Gly Arg Cys Ile Asn Ile Asn
225                 230                 235                 240

Trp Arg Cys Asp Asn Asp Asn Asp Cys Gly Asp Asn Ser Asp Glu Ala
                245                 250                 255

Gly Cys Ser His Ser Cys Ser Ser Thr Gln Phe Lys Cys Asn Ser Gly
            260                 265                 270

Arg Cys Ile Pro Glu His Trp Thr Cys Asp Gly Asp Asn Asp Cys Gly
        275                 280                 285

Asp Tyr Ser Asp Glu Thr His Ala Asn Cys Thr Asn Gln Ala Thr Arg
    290                 295                 300

Pro Pro Gly Gly Cys His Thr Asp Glu Phe Gln Cys Arg Leu Asp Gly
305                 310                 315                 320

Leu Cys Ile Pro Leu Arg Trp Arg Cys Asp Gly Asp Thr Asp Cys Met
                325                 330                 335

Asp Ser Ser Asp Glu Lys Ser Cys Glu Gly Val Thr His Val Cys Asp
            340                 345                 350

Pro Ser Val Lys Phe Gly Cys Lys Asp Ser Ala Arg Cys Ile Ser Lys
        355                 360                 365

Ala Trp Val Cys Asp Gly Asp Asn Asp Cys Glu Asp Asn Ser Asp Glu
    370                 375                 380

Glu Asn Cys Glu Ser Leu Ala Cys Arg Pro Pro Ser His Pro Cys Ala
385                 390                 395                 400

Asn Asn Thr Ser Val Cys Leu Pro Pro Asp Lys Leu Cys Asp Gly Asn
                405                 410                 415

Asp Asp Cys Gly Asp Gly Ser Asp Glu Gly Glu Leu Cys Asp Gln Cys
            420                 425                 430

Ser Leu Asn Asn Gly Gly Cys Ser His Asn Cys Ser Val Ala Pro Gly
        435                 440                 445

Glu Gly Ile Val Cys Ser Cys Pro Leu Gly Met Glu Leu Gly Pro Asp
    450                 455                 460

Asn His Thr Cys Gln Ile Gln Ser Tyr Cys Ala Lys His Leu Lys Cys
465                 470                 475                 480

Ser Gln Lys Cys Asp Gln Asn Lys Phe Ser Val Lys Cys Ser Cys Tyr
                485                 490                 495

Glu Gly Trp Val Leu Glu Pro Asp Gly Glu Ser Cys Arg Ser Leu Asp
            500                 505                 510

Pro Phe Lys Pro Phe Ile Ile Phe Ser Asn Arg His Glu Ile Arg Arg
        515                 520                 525

Ile Asp Leu His Lys Gly Asp Tyr Ser Val Leu Val Pro Gly Leu Arg
    530                 535                 540

Asn Thr Ile Ala Leu Asp Phe His Leu Ser Gln Ser Ala Leu Tyr Trp
545                 550                 555                 560

Thr Asp Val Val Glu Asp Lys Ile Tyr Arg Gly Lys Leu Leu Asp Asn
                565                 570                 575

Gly Ala Leu Thr Ser Phe Glu Val Val Ile Gln Tyr Gly Leu Ala Thr
            580                 585                 590
```

```
Pro Glu Gly Leu Ala Val Asp Trp Ile Ala Gly Asn Ile Tyr Trp Val
        595                 600                 605

Glu Ser Asn Leu Asp Gln Ile Glu Val Ala Lys Leu Asp Gly Thr Leu
    610                 615                 620

Arg Thr Thr Leu Leu Ala Gly Asp Ile Glu His Pro Arg Ala Ile Ala
625                 630                 635                 640

Leu Asp Pro Arg Asp Gly Ile Leu Phe Trp Thr Asp Trp Asp Ala Ser
                645                 650                 655

Leu Pro Arg Ile Glu Ala Ala Ser Met Ser Gly Ala Gly Arg Arg Thr
            660                 665                 670

Val His Arg Glu Thr Gly Ser Gly Gly Trp Pro Asn Gly Leu Thr Val
        675                 680                 685

Asp Tyr Leu Glu Lys Arg Ile Leu Trp Ile Asp Ala Arg Ser Asp Ala
    690                 695                 700

Ile Tyr Ser Ala Arg Tyr Asp Gly Ser Gly His Met Glu Val Leu Arg
705                 710                 715                 720

Gly His Glu Phe Leu Ser His Pro Phe Ala Val Thr Leu Tyr Gly Gly
                725                 730                 735

Glu Val Tyr Trp Thr Asp Trp Arg Thr Asn Thr Leu Ala Lys Ala Asn
            740                 745                 750

Lys Trp Thr Gly His Asn Val Thr Val Val Gln Arg Thr Asn Thr Gln
        755                 760                 765

Pro Phe Asp Leu Gln Val Tyr His Pro Ser Arg Gln Pro Met Ala Pro
    770                 775                 780

Asn Pro Cys Glu Ala Asn Gly Gly Gln Gly Pro Cys Ser His Leu Cys
785                 790                 795                 800

Leu Ile Asn Tyr Asn Arg Thr Val Ser Cys Ala Cys Pro His Leu Met
                805                 810                 815

Lys Leu His Lys Asp Asn Thr Thr Cys Tyr Glu Phe Lys Lys Phe Leu
            820                 825                 830

Leu Tyr Ala Arg Gln Met Glu Ile Arg Gly Val Asp Leu Asp Ala Pro
        835                 840                 845

Tyr Tyr Asn Tyr Ile Ile Ser Phe Thr Val Pro Asp Ile Asp Asn Val
    850                 855                 860

Thr Val Leu Asp Tyr Asp Ala Arg Glu Gln Arg Val Tyr Trp Ser Asp
865                 870                 875                 880

Val Arg Thr Gln Ala Ile Lys Arg Ala Phe Ile Asn Gly Thr Gly Val
                885                 890                 895

Glu Thr Val Val Ser Ala Asp Leu Pro Asn Ala His Gly Leu Ala Val
            900                 905                 910

Asp Trp Val Ser
        915
```

<210> SEQ ID NO 20
<211> LENGTH: 8120
<212> TYPE: DNA
<213> ORGANISM: Artificial Sequence
<220> FEATURE:
<223> OTHER INFORMATION: Synthetic Construct

<400> SEQUENCE: 20

```
ttgtacaaag tggttgatat ccagcacagt ggcggccgct cgagtctaga gggcccgcgg      60

ttcgaaggta agcctatccc taaccctctc ctcggtctcg attctacgcg taccggttag     120

taatgatcga caatcaacct ctggattaca aaatttgtga aagattgact ggtattctta     180
```

-continued

```
actatgttgc tccttttacg ctatgtggat acgctgcttt aatgcctttg tatcatgcta    240
ttgcttcccg tatggctttc attttctcct ccttgtataa atcctggttg ctgtctcttt    300
atgaggagtt gtggcccgtt gtcaggcaac gtggcgtggt gtgcactgtg tttgctgacg    360
caacccccac tggttggggc attgccacca cctgtcagct cctttccggg actttcgctt    420
tccccctccc tattgccacg gcggaactca tcgccgcctg ccttgcccgc tgctggacag    480
gggctcggct gttgggcact gacaattccg tggtgttgtc ggggaagctg acgtcctttc    540
catggctgct cgcctgtgtt gccacctgga ttctgcgcgg gacgtccttc tgctacgtcc    600
cttcggccct caatccagcg gaccttcctt cccgcggcct gctgccggct ctgcggcctc    660
ttccgcgtct tcgccttcgc cctcagacga gtcggatctc cctttgggcc gcctccccgc    720
ctggcgatgg tacctaccgg gtaggggagg cgcttttccc aaggcagtct ggagcatgcg    780
ctttagcagc cccgctgggc acttggcgct acacaagtgg cctctggcct cgcacacatt    840
ccacatccac cggtaggcgc caaccggctc cgttctttgg tggccccttc gcgccacctt    900
ctactcctcc cctagtcagg aagttccccc ccgccccgca gctcgcgtcg tgcaggacgt    960
gacaaatgga agtagcacgt ctcactagtc tcgtgcagat ggacagcacc gctgagcaat   1020
ggaagcgggt aggcctttgg ggcagcggcc aatagcagct ttgctccttc gctttctggg   1080
ctcagaggct gggaaggggt gggtccgggg gcgggctcag gggcgggctc aggggcgggg   1140
cgggcgcccg aaggtcctcc ggaggcccgg cattctgcac gcttcaaaag cgcacgtctg   1200
ccgcgctgtt ctcctcttcc tcatctccgg gcctttcgac tctagacacg tgttgacaat   1260
taatcatcgg catagtatat cggcatagta taatacgaca aggtgaggaa ctaaaccatg   1320
gccaagcctt tgtctcaaga agaatccacc ctcattgaaa gagcaacggc tacaatcaac   1380
agcatcccca tctctgaaga ctacagcgtc gccagcgcag ctctctctag cgacggccgc   1440
atcttcactg gtgtcaatgt atatcatttt actgggggac cttgtgcaga actcgtggtg   1500
ctgggcactg ctgctgctgc ggcagctggc aacctgactt gtatcgtcgc gatcggaaat   1560
gagaacaggg gcatcttgag cccctgcgga cggtgccgac aggtgcttct cgatctgcat   1620
cctgggatca aagccatagt gaaggacagt gatggacagc cgacggcagt tgggattcgt   1680
gaattgctgc cctctggtta tgtgtgggag ggctaagcac aattcgagct cggtaccttt   1740
aagaccaatg acttacaagg cagctgtaga tcttagccac tttttaaaag aaaagggggg   1800
actggaaggg ctaattcact cccaacgaag acaagatctg ctttttgctt gtactgggtc   1860
tctctggtta gaccagatct gagcctggga gctctctggc taactaggga acccactgct   1920
taagcctcaa taaagcttgc cttgagtgct tcaagtagtg tgtgcccgtc tgttgtgtga   1980
ctctggtaac tagagatccc tcagaccctt ttagtcagtg tggaaaatct ctagcagtag   2040
tagttcatgt catcttatta ttcagtattt ataacttgca aagaaatgaa tatcagagag   2100
tgagaggaac ttgtttattg cagcttataa tggttacaaa taaagcaata gcatcacaaa   2160
tttcacaaat aaagcatttt tttcactgca ttctagttgt ggtttgtcca aactcatcaa   2220
tgtatcttat catgtctggc tctagctatc ccgcccctaa ctccgcccat cccgccccta   2280
actccgccca gttccgccca ttctccgccc catggctgac taattttttt tatttatgca   2340
gaggccgagg ccgcctcggc ctctgagcta ttccagaagt agtgaggagg cttttttgga   2400
ggcctaggga cgtacccaat tcgccctata gtgagtcgta ttacgcgcgc tcactggccg   2460
tcgttttaca acgtcgtgac tgggaaaacc ctggcgttac ccaacttaat cgccttgcag   2520
cacatccccc tttcgccagc tggcgtaata gcgaagaggc ccgcaccgat cgcccttccc   2580
```

```
aacagttgcg cagcctgaat ggcgaatggg acgcgccctg tagcggcgca ttaagcgcgg   2640
cgggtgtggt ggttacgcgc agcgtgaccg ctacacttgc cagcgcccta gcgcccgctc   2700
ctttcgcttt cttcccttcc tttctcgcca cgttcgccgg ctttccccgt caagctctaa   2760
atcgggggct ccctttaggg ttccgattta gtgctttacg gcacctcgac cccaaaaaac   2820
ttgattaggg tgatggttca cgtagtgggc catcgccctg atagacggtt tttcgccctt   2880
tgacgttgga gtccacgttc tttaatagtg gactcttgtt ccaaactgga acaacactca   2940
accctatctc ggtctattct tttgatttat aagggatttt gccgatttcg gcctattggt   3000
taaaaaatga gctgatttaa caaaaattta acgcgaattt taacaaaata ttaacgctta   3060
caatttaggt ggcacttttc ggggaaatgt gcgcggaacc cctatttgtt tatttttcta   3120
aatacattca aatatgtatc cgctcatgag acaataaccc tgataaatgc ttcaataata   3180
ttgaaaaagg aagagtatga gtattcaaca tttccgtgtc gcccttattc ccttttttgc   3240
ggcattttgc cttcctgttt ttgctcaccc agaaacgctg gtgaaagtaa aagatgctga   3300
agatcagttg ggtgcacgag tgggttacat cgaactggat ctcaacagcg gtaagatcct   3360
tgagagtttt cgccccgaag aacgttttcc aatgatgagc acttttaaag ttctgctatg   3420
tggcgcggta ttatcccgta ttgacgccgg gcaagagcaa ctcggtcgcc gcatacacta   3480
ttctcagaat gacttggttg agtactcacc agtcacagaa aagcatctta cggatggcat   3540
gacagtaaga gaattatgca gtgctgccat aaccatgagt gataacactg cggccaactt   3600
acttctgaca acgatcggag gaccgaagga gctaaccgct tttttgcaca acatggggga   3660
tcatgtaact cgccttgatc gttgggaacc ggagctgaat gaagccatac caaacgacga   3720
gcgtgacacc acgatgcctg tagcaatggc aacaacgttg cgcaaactat taactggcga   3780
actacttact ctagcttccc ggcaacaatt aatagactgg atggaggcgg ataaagttgc   3840
aggaccactt ctgcgctcgg cccttccggc tggctggttt attgctgata aatctggagc   3900
cggtgagcgt gggtctcgcg gtatcattgc agcactgggg ccagatggta agccctcccg   3960
tatcgtagtt atctacacga cggggagtca ggcaactatg gatgaacgaa atagacagat   4020
cgctgagata ggtgcctcac tgattaagca ttggtaactg tcagaccaag tttactcata   4080
tatactttag attgatttaa aacttcattt ttaatttaaa aggatctagg tgaagatcct   4140
ttttgataat ctcatgacca aaatccctta acgtgagttt tcgttccact gagcgtcaga   4200
ccccgtagaa aagatcaaag gatcttcttg agatcctttt tttctgcgcg taatctgctg   4260
cttgcaaaca aaaaaaccac cgctaccagc ggtggtttgt ttgccggatc aagagctacc   4320
aactcttttt ccgaaggtaa ctggcttcag cagagcgcag ataccaaata ctgttcttct   4380
agtgtagccg tagttaggcc accacttcaa gaactctgta gcaccgccta catacctcgc   4440
tctgctaatc ctgttaccag tggctgctgc cagtggcgat aagtcgtgtc ttaccgggtt   4500
ggactcaaga cgatagttac cggataaggc gcagcggtcg ggctgaacgg ggggttcgtg   4560
cacacagccc agcttggagc gaacgaccta caccgaactg agatacctac agcgtgagct   4620
atgagaaagc gccacgcttc ccgaagggag aaaggcggac aggtatccgg taagcggcag   4680
ggtcggaaca ggagagcgca cgagggagct tccaggggga aacgcctggt atctttatag   4740
tcctgtcggg tttcgccacc tctgacttga gcgtcgattt ttgtgatgct cgtcaggggg   4800
gcggagccta tggaaaaacg ccagcaacgc ggccttttta cggttcctgg ccttttgctg   4860
gccttttgct cacatgttct ttcctgcgtt atcccctgat tctgtggata accgtattac   4920
```

-continued

```
cgcctttgag tgagctgata ccgctcgccg cagccgaacg accgagcgca gcgagtcagt   4980
gagcgaggaa gcggaagagc gcccaatacg caaaccgcct ctccccgcgc gttggccgat   5040
tcattaatgc agctggcacg acaggtttcc cgactggaaa gcgggcagtg agcgcaacgc   5100
aattaatgtg agttagctca ctcattaggc accccaggct ttacacttta tgcttccggc   5160
tcgtatgttg tgtggaattg tgagcggata acaatttcac acaggaaaca gctatgacca   5220
tgattacgcc aagcgcgcaa ttaaccctca ctaaagggaa caaaagctgg agctgcaagc   5280
ttaatgtagt cttatgcaat actcttgtag tcttgcaaca tggtaacgat gagttagcaa   5340
catgccttac aaggagagaa aaagcaccgt gcatgccgat tggtggaagt aaggtggtac   5400
gatcgtgcct tattaggaag gcaacagacg ggtctgacat ggattggacg aaccactgaa   5460
ttgccgcatt gcagagatat tgtatttaag tgcctagctc gatacataaa cgggtctctc   5520
tggttagacc agatctgagc ctgggagctc tctggctaac tagggaaccc actgcttaag   5580
cctcaataaa gcttgccttg agtgcttcaa gtagtgtgtg cccgtctgtt gtgtgactct   5640
ggtaactaga gatccctcag acccttttag tcagtgtgga aaatctctag cagtggcgcc   5700
cgaacaggga cttgaaagcg aaagggaaac cagaggagct ctctcgacgc aggactcggc   5760
ttgctgaagc gcgcacggca agaggcgagg ggcggcgact ggtgagtacg ccaaaaattt   5820
tgactagcgg aggctagaag gagagagatg ggtgcgagag cgtcagtatt aagcggggga   5880
gaattagatc gcgatgggaa aaaattcggt taaggccagg gggaaagaaa aaatataaat   5940
taaaacatat agtatgggca agcagggagc tagaacgatt cgcagttaat cctggcctgt   6000
tagaaacatc agaaggctgt agacaaatac tgggacagct acaaccatcc cttcagacag   6060
gatcagaaga acttagatca ttatataata cagtagcaac cctctattgt gtgcatcaaa   6120
ggatagagat aaaagacacc aaggaagctt tagacaagat agaggaagag caaaacaaaa   6180
gtaagaccac cgcacagcaa gcggccgctg atcttcagac ctggaggagg agatatgagg   6240
gacaattgga gaagtgaatt atataaatat aaagtagtaa aaattgaacc attaggagta   6300
gcacccacca aggcaaagag aagagtggtg cagagagaaa aaagagcagt gggaatagga   6360
gctttgttcc ttgggttctt gggagcagca ggaagcacta tgggcgcagc gtcaatgacg   6420
ctgacggtac aggccagaca attattgtct ggtatagtgc agcagcagaa caatttgctg   6480
agggctattg aggcgcaaca gcatctgttg caactcacag tctggggcat caagcagctc   6540
caggcaagaa tcctggctgt ggaaagatac ctaaaggatc aacagctcct ggggatttgg   6600
ggttgctctg gaaaactcat ttgcaccact gctgtgcctt ggaatgctag ttggagtaat   6660
aaatctctgg aacagatttg gaatcacacg acctggatgg agtgggacag agaaattaac   6720
aattacacaa gcttaataca ctccttaatt gaagaatcgc aaaaccagca agaaaagaat   6780
gaacaagaat tattggaatt agataaatgg gcaagtttgt ggaattggtt taacataaca   6840
aattggctgt ggtatataaa attattcata atgatagtag gaggcttggt aggtttaaga   6900
atagtttttg ctgtactttc tatagtgaat agagttaggc agggatattc accattatcg   6960
tttcagaccc acctcccaac cccgagggga cccgacaggc ccgaaggaat agaagaagaa   7020
ggtggagaga gagacagaga cagatccatt cgattagtga acggatctcg acggtatcga   7080
ttaactttta aaagaaaagg ggggattggg gggtacagtg caggggaaag aatagtagac   7140
ataatagcaa cagacataca aactaaagaa ttacaaaaac aaattacaaa aattcaaaat   7200
tttatcgatg tcgacgttaa cgctagtgat atcaactttg tatagaaaag ttgaagcttg   7260
ggagttccgc gttacataac ttacggtaaa tggcccgcct ggctgaccgc ccaacgaccc   7320
```

-continued

```
ccgcccattg acgtcaataa tgacgtatgt tcccatagta acgccaatag ggactttcca   7380

ttgacgtcaa tgggtggagt atttacggta aactgcccac ttggcagtac atcaagtgta   7440

tcatatgcca agtacgcccc ctattgacgt caatgacggt aaatggcccg cctggcatta   7500

tgcccagtac atgaccttat gggactttcc tacttggcag tacatctacg tattagtcat   7560

cgctattacc atggtgatgc ggttttggca gtacatcaat gggcgtggat agcggtttga   7620

ctcacgggga tttccaagtc tccaccccat tgacgtcaat gggagtttgt tttggcacca   7680

aaatcaacgg gactttccaa aatgtcgtaa caactccgcc ccattgacgc aaatgggcgg   7740

taggcgtgta cggtgggagg tctatataag cagagctcgt ttagtgaacc gtcagatcgc   7800

ctggagacgc catccacgct gttttgacct ccatagaaga caccgactct agaggatcca   7860

ctagtccagt gtggtggaat tctgcagata tcacaagttt gtacaaaaaa gcaggcttta   7920

aagggaggta gtgagtcgac cagtggatcc tggaggcttg ctgaaggctg tatgctgagc   7980

agaacttgtt gcagtggggt tttggccact gactgacccc actgccaagt tctgctcagg   8040

acacaaggcc tgttactagc actcacatgg aacaaatggc ccagatctgg ccgcactcga   8100

gatatctaga cccagctttc                                               8120
```

<210> SEQ ID NO 21
<211> LENGTH: 8120
<212> TYPE: DNA
<213> ORGANISM: Artificial Sequence
<220> FEATURE:
<223> OTHER INFORMATION: Synthetic Construct

<400> SEQUENCE: 21

```
ttgtacaaag tggttgatat ccagcacagt ggcggccgct cgagtctaga gggcccgcgg     60

ttcgaaggta agcctatccc taaccctctc ctcggtctcg attctacgcg taccggttag    120

taatgatcga caatcaacct ctggattaca aaatttgtga aagattgact ggtattctta    180

actatgttgc tccttttacg ctatgtggat acgctgcttt aatgcctttg tatcatgcta    240

ttgcttcccg tatggctttc attttctcct ccttgtataa atcctggttg ctgtctcttt    300

atgaggagtt gtggcccgtt gtcaggcaac gtggcgtggt gtgcactgtg tttgctgacg    360

caacccccac tggttggggc attgccacca cctgtcagct cctttccggg actttcgctt    420

tccccctccc tattgccacg gcggaactca tcgccgcctg ccttgcccgc tgctggacag    480

gggctcggct gttgggcact gacaattccg tggtgttgtc ggggaagctg acgtcctttc    540

catggctgct cgcctgtgtt gccacctgga ttctgcgcgg gacgtccttc tgctacgtcc    600

cttcggccct caatccagcg gaccttcctt cccgcggcct gctgccggct ctgcggcctc    660

ttccgcgtct tcgccttcgc cctcagacga gtcggatctc cctttgggcc gcctccccgc    720

ctggcgatgg tacctaccgg gtaggggagg cgcttttccc aaggcagtct ggagcatgcg    780

ctttagcagc cccgctgggc acttggcgct acacaagtgg cctctggcct cgcacacatt    840

ccacatccac cggtaggcgc caaccggctc cgttctttgg tggccccttc gcgccacctt    900

ctactcctcc cctagtcagg aagttccccc ccgccccgca gctcgcgtcg tgcaggacgt    960

gacaaatgga agtagcacgt ctcactagtc tcgtgcagat ggacagcacc gctgagcaat   1020

ggaagcgggt aggcctttgg ggcagcggcc aatagcagct ttgctccttc gctttctggg   1080

ctcagaggct gggaaggggt gggtccgggg gcgggctcag gggcgggctc aggggcgggg   1140

cgggcgcccg aaggtcctcc ggaggcccgg cattctgcac gcttcaaaag cgcacgtctg   1200
```

-continued

```
ccgcgctgtt ctcctcttcc tcatctccgg gcctttcgac tctagacacg tgttgacaat   1260
taatcatcgg catagtatat cggcatagta taatacgaca aggtgaggaa ctaaaccatg   1320
gccaagcctt tgtctcaaga agaatccacc ctcattgaaa gagcaacggc tacaatcaac   1380
agcatcccca tctctgaaga ctacagcgtc gccagcgcag ctctctctag cgacggccgc   1440
atcttcactg gtgtcaatgt atatcatttt actgggggac cttgtgcaga actcgtggtg   1500
ctgggcactg ctgctgctgc ggcagctggc aacctgactt gtatcgtcgc gatcggaaat   1560
gagaacaggg gcatcttgag cccctgcgga cggtgccgac aggtgcttct cgatctgcat   1620
cctgggatca aagccatagt gaaggacagt gatggacagc cgacggcagt tgggattcgt   1680
gaattgctgc cctctggtta tgtgtgggag ggctaagcac aattcgagct cggtaccttt   1740
aagaccaatg acttacaagg cagctgtaga tcttagccac tttttaaaag aaaagggggg   1800
actggaaggg ctaattcact cccaacgaag acaagatctg ctttttgctt gtactgggtc   1860
tctctggtta gaccagatct gagcctggga gctctctggc taactaggga acccactgct   1920
taagcctcaa taaagcttgc cttgagtgct tcaagtagtg tgtgcccgtc tgttgtgtga   1980
ctctggtaac tagagatccc tcagaccctt ttagtcagtg tggaaaatct ctagcagtag   2040
tagttcatgt catcttatta ttcagtattt ataacttgca aagaaatgaa tatcagagag   2100
tgagaggaac ttgtttattg cagcttataa tggttacaaa taaagcaata gcatcacaaa   2160
tttcacaaat aaagcatttt tttcactgca ttctagttgt ggtttgtcca aactcatcaa   2220
tgtatcttat catgtctggc tctagctatc ccgcccctaa ctccgcccat cccgccccta   2280
actccgccca gttccgccca ttctccgccc catggctgac taattttttt tatttatgca   2340
gaggccgagg ccgcctcggc ctctgagcta ttccagaagt agtgaggagg cttttttgga   2400
ggcctaggga cgtacccaat tcgccctata gtgagtcgta ttacgcgcgc tcactggccg   2460
tcgttttaca acgtcgtgac tgggaaaacc ctggcgttac ccaacttaat cgccttgcag   2520
cacatccccc tttcgccagc tggcgtaata gcgaagaggc ccgcaccgat cgcccttccc   2580
aacagttgcg cagcctgaat ggcgaatggg acgcgccctg tagcggcgca ttaagcgcgg   2640
cgggtgtggt ggttacgcgc agcgtgaccg ctacacttgc cagcgcccta gcgcccgctc   2700
ctttcgcttt cttcccttcc tttctcgcca cgttcgccgg ctttccccgt caagctctaa   2760
atcgggggct ccctttaggg ttccgattta gtgctttacg gcacctcgac cccaaaaaac   2820
ttgattaggg tgatggttca cgtagtgggc catcgccctg atagacggtt tttcgccctt   2880
tgacgttgga gtccacgttc tttaatagtg gactcttgtt ccaaactgga acaacactca   2940
accctatctc ggtctattct tttgatttat aagggatttt gccgatttcg gcctattggt   3000
taaaaaatga gctgatttaa caaaaattta acgcgaattt taacaaaata ttaacgctta   3060
caatttaggt ggcacttttc ggggaaatgt gcgcggaacc cctatttgtt tatttttcta   3120
aatacattca aatatgtatc cgctcatgag acaataaccc tgataaatgc ttcaataata   3180
ttgaaaaagg aagagtatga gtattcaaca tttccgtgtc gcccttattc ccttttttgc   3240
ggcattttgc cttcctgttt ttgctcaccc agaaacgctg gtgaaagtaa aagatgctga   3300
agatcagttg ggtgcacgag tgggttacat cgaactggat ctcaacagcg gtaagatcct   3360
tgagagtttt cgccccgaag aacgttttcc aatgatgagc acttttaaag ttctgctatg   3420
tggcgcggta ttatcccgta ttgacgccgg gcaagagcaa ctcggtcgcc gcatacacta   3480
ttctcagaat gacttggttg agtactcacc agtcacagaa aagcatctta cggatggcat   3540
gacagtaaga gaattatgca gtgctgccat aaccatgagt gataacactg cggccaactt   3600
```

-continued

```
acttctgaca acgatcggag gaccgaagga gctaaccgct tttttgcaca acatggggga   3660
tcatgtaact cgccttgatc gttgggaacc ggagctgaat gaagccatac caaacgacga   3720
gcgtgacacc acgatgcctg tagcaatggc aacaacgttg cgcaaactat taactggcga   3780
actacttact ctagcttccc ggcaacaatt aatagactgg atggaggcgg ataaagttgc   3840
aggaccactt ctgcgctcgg cccttccggc tggctggttt attgctgata aatctggagc   3900
cggtgagcgt gggtctcgcg gtatcattgc agcactgggg ccagatggta agccctcccg   3960
tatcgtagtt atctacacga cggggagtca ggcaactatg gatgaacgaa atagacagat   4020
cgctgagata ggtgcctcac tgattaagca ttggtaactg tcagaccaag tttactcata   4080
tatactttag attgatttaa aacttcattt ttaatttaaa aggatctagg tgaagatcct   4140
ttttgataat ctcatgacca aaatccctta acgtgagttt tcgttccact gagcgtcaga   4200
ccccgtagaa aagatcaaag gatcttcttg agatcctttt tttctgcgcg taatctgctg   4260
cttgcaaaca aaaaaaccac cgctaccagc ggtggtttgt ttgccggatc aagagctacc   4320
aactcttttt ccgaaggtaa ctggcttcag cagagcgcag ataccaaata ctgttcttct   4380
agtgtagccg tagttaggcc accacttcaa gaactctgta gcaccgccta catacctcgc   4440
tctgctaatc ctgttaccag tggctgctgc cagtggcgat aagtcgtgtc ttaccgggtt   4500
ggactcaaga cgatagttac cggataaggc gcagcggtcg ggctgaacgg ggggttcgtg   4560
cacacagccc agcttggagc gaacgaccta caccgaactg agatacctac agcgtgagct   4620
atgagaaagc gccacgcttc ccgaagggag aaaggcggac aggtatccgg taagcggcag   4680
ggtcggaaca ggagagcgca cgagggagct tccaggggga aacgcctggt atctttatag   4740
tcctgtcggg tttcgccacc tctgacttga gcgtcgattt ttgtgatgct cgtcaggggg   4800
gcggagccta tggaaaaacg ccagcaacgc ggccttttta cggttcctgg ccttttgctg   4860
gccttttgct cacatgttct ttcctgcgtt atcccctgat tctgtggata accgtattac   4920
cgcctttgag tgagctgata ccgctcgccg cagccgaacg accgagcgca gcgagtcagt   4980
gagcgaggaa gcggaagagc gcccaatacg caaaccgcct ctccccgcgc gttggccgat   5040
tcattaatgc agctggcacg acaggtttcc cgactggaaa gcgggcagtg agcgcaacgc   5100
aattaatgtg agttagctca ctcattaggc accccaggct ttacacttta tgcttccggc   5160
tcgtatgttg tgtggaattg tgagcggata acaatttcac acaggaaaca gctatgacca   5220
tgattacgcc aagcgcgcaa ttaaccctca ctaaagggaa caaaagctgg agctgcaagc   5280
ttaatgtagt cttatgcaat actcttgtag tcttgcaaca tggtaacgat gagttagcaa   5340
catgccttac aaggagagaa aaagcaccgt gcatgccgat tggtggaagt aaggtggtac   5400
gatcgtgcct tattaggaag gcaacagacg ggtctgacat ggattggacg aaccactgaa   5460
ttgccgcatt gcagagatat tgtatttaag tgcctagctc gatacataaa cgggtctctc   5520
tggttagacc agatctgagc ctgggagctc tctggctaac tagggaaccc actgcttaag   5580
cctcaataaa gcttgccttg agtgcttcaa gtagtgtgtg cccgtctgtt gtgtgactct   5640
ggtaactaga gatccctcag acccttttag tcagtgtgga aaatctctag cagtggcgcc   5700
cgaacaggga cttgaaagcg aaagggaaac cagaggagct ctctcgacgc aggactcggc   5760
ttgctgaagc gcgcacggca agaggcgagg ggcggcgact ggtgagtacg ccaaaaattt   5820
tgactagcgg aggctagaag gagagagatg ggtgcgagag cgtcagtatt aagcggggga   5880
gaattagatc gcgatgggaa aaaattcggt taaggccagg gggaaagaaa aaatataaat   5940
```

-continued

```
taaaacatat agtatgggca agcagggagc tagaacgatt cgcagttaat cctggcctgt   6000

tagaaacatc agaaggctgt agacaaatac tgggacagct acaaccatcc cttcagacag   6060

gatcagaaga acttagatca ttatataata cagtagcaac cctctattgt gtgcatcaaa   6120

ggatagagat aaaagacacc aaggaagctt tagacaagat agaggaagag caaaacaaaa   6180

gtaagaccac cgcacagcaa gcggccgctg atcttcagac ctggaggagg agatatgagg   6240

gacaattgga gaagtgaatt atataaatat aaagtagtaa aaattgaacc attaggagta   6300

gcacccacca aggcaaagag aagagtggtg cagagagaaa aaagagcagt gggaatagga   6360

gctttgttcc ttgggttctt gggagcagca ggaagcacta tgggcgcagc gtcaatgacg   6420

ctgacggtac aggccagaca attattgtct ggtatagtgc agcagcagaa caatttgctg   6480

agggctattg aggcgcaaca gcatctgttg caactcacag tctggggcat caagcagctc   6540

caggcaagaa tcctggctgt ggaaagatac ctaaaggatc aacagctcct ggggatttgg   6600

ggttgctctg gaaaactcat ttgcaccact gctgtgcctt ggaatgctag ttggagtaat   6660

aaatctctgg aacagatttg gaatcacacg acctggatgg agtgggacag agaaattaac   6720

aattacacaa gcttaataca ctccttaatt gaagaatcgc aaaaccagca agaaaagaat   6780

gaacaagaat tattggaatt agataaatgg gcaagtttgt ggaattggtt taacataaca   6840

aattggctgt ggtatataaa attattcata atgatagtag gaggcttggt aggtttaaga   6900

atagtttttg ctgtactttc tatagtgaat agagttaggc agggatattc accattatcg   6960

tttcagaccc acctcccaac cccgagggga cccgacaggc ccgaaggaat agaagaagaa   7020

ggtggagaga gagacagaga cagatccatt cgattagtga acggatctcg acggtatcga   7080

ttaactttta aaagaaaagg ggggattggg gggtacagtg caggggaaag aatagtagac   7140

ataatagcaa cagacataca aactaaagaa ttacaaaaac aaattacaaa aattcaaaat   7200

tttatcgatg tcgacgttaa cgctagtgat atcaactttg tatagaaaag ttgaagcttg   7260

ggagttccgc gttacataac ttacggtaaa tggcccgcct ggctgaccgc ccaacgaccc   7320

ccgcccattg acgtcaataa tgacgtatgt tcccatagta acgccaatag ggactttcca   7380

ttgacgtcaa tgggtggagt atttacggta aactgcccac ttggcagtac atcaagtgta   7440

tcatatgcca agtacgcccc ctattgacgt caatgacggt aaatggcccg cctggcatta   7500

tgcccagtac atgaccttat gggactttcc tacttggcag tacatctacg tattagtcat   7560

cgctattacc atggtgatgc ggttttggca gtacatcaat gggcgtggat agcggtttga   7620

ctcacgggga tttccaagtc tccaccccat tgacgtcaat gggagtttgt tttggcacca   7680

aaatcaacgg gactttccaa aatgtcgtaa caactccgcc ccattgacgc aaatgggcgg   7740

taggcgtgta cggtgggagg tctatataag cagagctcgt ttagtgaacc gtcagatcgc   7800

ctggagacgc catccacgct gttttgacct ccatagaaga caccgactct agaggatcca   7860

ctagtccagt gtggtggaat tctgcagata tcacaagttt gtacaaaaaa gcaggcttta   7920

aagggaggta gtgagtcgac cagtggatcc tggaggcttg ctgaaggctg tatgctgcat   7980

acacgaggaa cagctcatgt tttggccact gactgacatg agctgcctcg tgtatgcagg   8040

acacaaggcc tgttactagc actcacatgg aacaaatggc ccagatctgg ccgcactcga   8100

gatatctaga cccagctttc                                               8120
```

<210> SEQ ID NO 22
<211> LENGTH: 13463
<212> TYPE: DNA
<213> ORGANISM: Artificial Sequence -continued
<220> FEATURE:
<223> OTHER INFORMATION: Synthetic Construct

<400> SEQUENCE: 22
gggctgcagg aattcgagct cgcccgacat tgattattga ctagttatta atagtaatca 60
attacggggt cattagttca tagcccatat atggagttcc gcgttacata acttacggta 120
aatggcccgc ctggctgacc gcccaacgac ccccgcccat tgacgtcaat aatgacgtat 180
gttcccatag taacgccaat agggactttc cattgacgtc aatgggtgga gtatttacgg 240
taaactgccc acttggcagt acatcaagtg tatcatatgc caagtacgcc ccctattgac 300
gtcaatgacg gtaaatggcc cgcctggcat tatgcccagt acatgacctt atgggacttt 360
cctacttggc agtacatcta cgtattagtc atcgctatta ccatggtgat gcggttttgg 420
cagtacatca atgggcgtgg atagcggttt gactcacggg gatttccaag tctccacccc 480
attgacgtca atgggagttt gttttggcac caaaatcaac gggactttcc aaaatgtcgt 540
aacaactccg ccccattgac gcaaatgggc ggtaggcgtg tacggtggga ggtctatata 600
agcagagctc gtttagtgaa ccgtcagatc gcctggagac gccatccacg ctgttttgac 660
ctccatagaa gacaccggga ccgatccagc ctccgcggcc gggaacggtg cattggaacg 720
cggattcccc gtgccaagag tgacgtaagt accgcctata gagtctatag gcccaccccc 780
ttggcttctt atgcgacgga tcgatcccgt aataagcttc gaggtccgcg gccgcgttga 840
cgcgcacggc aagaggcgag gggcggcgac tggtgagaga tgggtgcgag agcgtcagta 900
ttaagcgggg gagaattaga tcgatgggaa aaaattcggt taaggccagg gggaaagaaa 960
aaatataaat taaaacatat agtatgggca agcagggagc tagaacgatt cgcagttaat 1020
cctggcctgt tagaaacatc agaaggctgt agacaaatac tgggacagct acaaccatcc 1080
cttcagacag gatcagaaga acttagatca ttatataata cagtagcaac cctctattgt 1140
gtgcatcaaa ggatagagat aaaagacacc aaggaagctt tagacaagat agaggaagag 1200
caaaacaaaa gtaagaaaaa agcacagcaa gcagcagctg acacaggaca cagcaatcag 1260
gtcagccaaa attaccctat agtgcagaac atccaggggc aaatggtaca tcaggccata 1320
tcacctagaa ctttaaatgc atgggtaaaa gtagtagaag agaaggcttt cagcccagaa 1380
gtgataccca tgttttcagc attatcagaa ggagccaccc cacaagattt aaacaccatg 1440
ctaaacacag tgggggggaca tcaagcagcc atgcaaatgt taaaagagac catcaatgag 1500
gaagctgcag aatgggatag agtgcatcca gtgcatgcag ggcctattgc accaggccag 1560
atgagagaac caaggggaag tgacatagca ggaactacta gtactagtac ccttcaggaa 1620
caaataggat ggatgacaca taatccacct atcccagtag gagaaatcta taaaagatgg 1680
ataatcctgg gattaaataa aatagtaaga atgtatagcc ctaccagcat tctggacata 1740
agacaaggac caaaggaacc ctttagagac tatgtagacc gattctataa aactctaaga 1800
gccgagcaag cttcacaaga ggtaaaaaat tggatgacag aaaccttgtt ggtccaaaat 1860
gcgaacccag attgtaagac tattttaaaa gcattgggac caggagcgac actagaagaa 1920
atgatgacag catgtcaggg agtgggggga cccggccata aagcaagagt tttggctgaa 1980
gcaatgagcc aagtaacaaa tccagctacc ataatgatac agaaaggcaa ttttaggaac 2040
caaagaaaga ctgttaagtg tttcaattgt ggcaaagaag ggcacatagc caaaaattgc 2100
agggccccta ggaaaaaggg ctgttggaaa tgtggaaagg aaggacacca aatgaaagat 2160
tgtactgaga gacaggctaa ttttttaggg aagatctggc cttcccacaa gggaaggcca 2220

```
gggaattttc ttcagagcag accagagcca acagccccac cagaagagag cttcaggttt   2280
ggggaagaga caacaactcc ctctcagaag caggagccga tagacaagga actgtatcct   2340
ttagcttccc tcagatcact ctttggcagc gacccctcgt cacaataaag ataggggggc   2400
aattaaagga agctctatta gatacaggag cagatgatac agtattagaa gaaatgaatt   2460
tgccaggaag atggaaacca aaaatgatag ggggaattgg aggttttatc aaagtaggac   2520
agtatgatca gatactcata gaaatctgcg gacataaagc tataggtaca gtattagtag   2580
gacctacacc tgtcaacata attggaagaa atctgttgac tcagattggc tgcactttaa   2640
attttcccat tagtcctatt gagactgtac cagtaaaatt aaagccagga atggatggcc   2700
caaaagttaa acaatggcca ttgacagaag aaaaaataaa agcattagta gaaatttgta   2760
cagaaatgga aaaggaagga aaaatttcaa aaattgggcc tgaaaatcca tacaatactc   2820
cagtatttgc cataaagaaa aaagacagta ctaaatggag aaaattagta gatttcagag   2880
aacttaataa gagaactcaa gatttctggg aagttcaatt aggaatacca catcctgcag   2940
ggttaaaaca gaaaaaatca gtaacagtac tggatgtggg cgatgcatat ttttcagttc   3000
ccttagataa agacttcagg aagtatactg catttaccat acctagtata aacaatgaga   3060
caccagggat tagatatcag tacaatgtgc ttccacaggg atggaaagga tcaccagcaa   3120
tattccagtg tagcatgaca aaaatcttag agccttttag aaaacaaaat ccagacatag   3180
tcatctatca atacatggat gatttgtatg taggatctga cttagaaata gggcagcata   3240
gaacaaaaat agaggaactg agacaacatc tgttgaggtg gggatttacc acaccagaca   3300
aaaaacatca gaaagaacct ccattccttt ggatgggtta tgaactccat cctgataaat   3360
ggacagtaca gcctatagtg ctgccagaaa aggacagctg gactgtcaat gacatacaga   3420
aattagtggg aaaattgaat tgggcaagtc agatttatgc agggattaaa gtaaggcaat   3480
tatgtaaact tcttagggga accaaagcac taacagaagt agtaccacta acagaagaag   3540
cagagctaga actggcagaa aacagggaga ttctaaaaga accggtacat ggagtgtatt   3600
atgacccatc aaaagactta atagcagaaa tacagaagca ggggcaaggc caatggacat   3660
atcaaattta tcaagagcca tttaaaaatc tgaaaacagg aaaatatgca agaatgaagg   3720
gtgcccacac taatgatgtg aaacaattaa cagaggcagt acaaaaaata gccacagaaa   3780
gcatagtaat atggggaaag actcctaaat ttaaattacc catacaaaag gaaacatggg   3840
aagcatggtg gacagagtat tggcaagcca cctggattcc tgagtgggag tttgtcaata   3900
cccctccctt agtgaagtta tggtaccagt tagagaaaga acccataata ggagcagaaa   3960
ctttctatgt agatggggca gccaataggg aaactaaatt aggaaaagca ggatatgtaa   4020
ctgacagagg aagacaaaaa gttgtccccc taacggacac aacaaatcag aagactgagt   4080
tacaagcaat tcatctagct ttgcaggatt cgggattaga agtaaacata gtgacagact   4140
cacaatatgc attgggaatc attcaagcac aaccagataa gagtgaatca gagttagtca   4200
gtcaaataat agagcagtta ataaaaaagg aaaaagtcta cctggcatgg gtaccagcac   4260
acaaaggaat tggaggaaat gaacaagtag atgggttggt cagtgctgga atcaggaaag   4320
tactattttt agatggaata gataaggccc aagaagaaca tgagaaatat cacagtaatt   4380
ggagagcaat ggctagtgat tttaacctac cacctgtagt agcaaaagaa atagtagcca   4440
gctgtgataa atgtcagcta aaaggggaag ccatgcatgg acaagtagac tgtagcccag   4500
gaatatggca gctagattgt acacatttag aaggaaaagt tatcttggta gcagttcatg   4560
tagccagtgg atatatagaa gcagaagtaa ttccagcaga gacagggcaa gaaacagcat   4620
```

-continued

```
acttcctctt aaaattagca ggaagatggc cagtaaaaac agtacataca gacaatggca   4680
gcaatttcac cagtactaca gttaaggccg cctgttggtg ggcggggatc aagcaggaat   4740
ttggcattcc ctacaatccc caaagtcaag gagtaataga atctatgaat aaagaattaa   4800
agaaaattat aggacaggta agagatcagg ctgaacatct taagacagca gtacaaatgg   4860
cagtattcat ccacaatttt aaaagaaaag gggggattgg ggggtacagt gcaggggaaa   4920
gaatagtaga cataatagca acagacatac aaactaaaga attacaaaaa caaattacaa   4980
aaattcaaaa ttttcgggtt tattacaggg acagcagaga tccagtttgg aaaggaccag   5040
caaagctcct ctggaaaggt gaaggggcag tagtaataca agataatagt gacataaaag   5100
tagtgccaag aagaaaagca aagatcatca gggattatgg aaaacagatg gcaggtgatg   5160
attgtgtggc aagtagacag gatgaggatt aacacatgga aaagattagt aaaacaccat   5220
atgtatattt caaggaaagc taaggactgg ttttatagac atcactatga aagtactaat   5280
ccaaaaataa gttcagaagt acacatccca ctaggggatg ctaaattagt aataacaaca   5340
tattggggtc tgcatacagg agaaagagac tggcatttgg gtcagggagt ctccatagaa   5400
tggaggaaaa agagatatag cacacaagta gaccctgacc tagcagacca actaattcat   5460
ctgcactatt ttgattgttt ttcagaatct gctataagaa ataccatatt aggacgtata   5520
gttagtccta ggtgtgaata tcaagcagga cataacaagg taggatctct acagtacttg   5580
gcactagcag cattaataaa accaaaacag ataaagccac ctttgcctag tgttaggaaa   5640
ctgacagagg acagatggaa caagccccag aagaccaagg gccacagagg gagccataca   5700
atgaatggac actagagctt ttagaggaac ttaagagtga agctgttaga cattttccta   5760
ggatatggct ccataactta ggacaacata tctatgaaac ttacggggat acttgggcag   5820
gagtggaagc cataataaga attctgcaac aactgctgtt tatccatttc agaattgggt   5880
gtcgacatag cagaataggc gttactcgac agaggagagc aagaaatgga gccagtagat   5940
cctagactag agccctggaa gcatccagga agtcagccta aaactgcttg taccaattgc   6000
tattgtaaaa agtgttgctt tcattgccaa gtttgtttca tgacaaaagc cttaggcatc   6060
tcctatggca ggaagaagcg gagacagcga cgaagagctc atcagaacag tcagactcat   6120
caagcttctc tatcaaagca gtaagtagta catgtaatgc aacctataat agtagcaata   6180
gtagcattag tagtagcaat aataatagca atagttgtgt ggtccatagt aatcatagaa   6240
tataggaaaa tattaagaca aagaaaaata gacaggttaa ttgatagact aatagaaaga   6300
gcagaagaca gtggcaatga gagtgaagga gaagtatcag cacttgtgga gatgggggtg   6360
gaaatggggc accatgctcc ttgggatatt gatgatctgt agttgagcgg ccgctgatct   6420
tcagacttgg aggaggagat atgagggaca attggagaag tgaattatat aaatataaag   6480
tagtaaaaat tgaaccatta ggagtagcac ccaccaaggc aaagagaaga gtggtgcaga   6540
gagaaaaaag agcagtggga ataggagctt tgttccttgg gttcttggga gcagcaggaa   6600
gcactatggg cgcagcctca atgacgctga cggtacaggc cagacaatta ttgtctggta   6660
tagtgcagca gcagaacaat ttgctgaggg ctattgaggc gcaacagcat ctgttgcaac   6720
tcacagtctg gggcatcaag cagctccaag caagaatcct agctgtggaa agatacctaa   6780
aggatcaaca gctcctaggg atttggggtt gctctggaaa actcatttgc accactgctg   6840
tgccttggaa tgctagttgg agtaataaat ctctggaaca gatctggaat cacacgacct   6900
ggatggagtg ggacagagaa attaacaatt acacaagctt aatacactcc ttaattgaag   6960
```

```
aatcgcaaaa ccagcaagaa aagaatgaac aagaattatt ggaattagat aaatgggcaa   7020

gtttgtggaa ttggtttaac ataacaaatt ggctgtggta tataaaatta ttcataatga   7080

tagtaggagg cttggtaggt ttaagaatag tttttgctgt actttctata gtgaatagag   7140

ttaggcaggg atattcacca ttatcgtttc agacccacct cccaatcccg aggggacccg   7200

acaggcccga aggaatagaa gaagaaggtg gagagagaga cagagacaga tccattcgat   7260

tagtgaacgg atccttggca cttatctggg acgatctgcg gagcctgtgc ctcttcagct   7320

accaccgctt gagagactta ctcttgattg taacgaggat tgtggaactt ctgggacgca   7380

gggggtggga agccctcaaa tattggtgga atctcctaca atattggagt caggagctaa   7440

agaatagtgc tgttagcttg ctcaatgcca cagccatagc agtagctgag gggacagata   7500

gggttataga agtagtacaa ggagcttgta gagctattcg ccacatacct agaagaataa   7560

gacagggctt ggaaaggatt ttgctataag atgggtggca agtggtcaaa aagtagtgtg   7620

attggatggc ctactgtaag ggaaagaatg agacgagctg agccagcagc agatggggtg   7680

ggagcagtat ctcgagacct agaaaaacat ggagcaatca caagtagcaa tacagcagct   7740

accaatgctg attgtgcctg gctagaagca caagaggagg aggaggtggg ttttccagtc   7800

acacctcagg tacctttaag accaatgact tacaaggcag ctgtagatct tagccacttt   7860

ttaaaagaaa aggggggact ggaagggcta attcactccc aacgaagaca agatatcctt   7920

gatctgtgga tctaccacac acaaggctac ttccctgatt ggcagaacta cacaccaggg   7980

ccagggatca gatatccact gacctttgga tggtgctaca agctagtacc agttgagcaa   8040

gagaaggtag aagaagccaa tgaaggagag aacacccgct tgttacaccc tgtgagcctg   8100

catgggatgg atgacccgga gagagaagta ttagagtgga ggtttgacag ccgcctagca   8160

tttcatcaca tggcccgaga gctgcatccg gagtacttca agaactgctg agcggccgcc   8220

ccggtgacct tcagaccttg gcactggagg tggcccggca gaagcgcggc atcgtggatc   8280

agtgctgcac cagcatctgc tctctctacc aactggagaa ctactgcaac taggcccacc   8340

actaccctgt ccacccctct gcaatgaata aaacctttga aagagcacta caagttgtgt   8400

gtacatgcgt gcatgtgcat atgtggtgcg gggggaacat gagtggggct ggctggagtg   8460

gcgatgataa gctgtcaaac atgagaattc ttgaagacga aagggcctcg tgatacgcct   8520

atttttatag gttaatgtca tgataataat ggtttcttag tctagaatta attccgtgta   8580

ttctatagtg tcacctaaat cgtatgtgta tgatacataa ggttatgtat taattgtagc   8640

cgcgttctaa cgacaatatg tacaagccta attgtgtagc atctggctta ctgaagcaga   8700

ccctatcatc tctctcgtaa actgccgtca gagtcggttt ggttggacga accttctgag   8760

tttctggtaa cgccgttccg caccccggaa atggtcagcg aaccaatcag cagggtcatc   8820

gctagccaga tcctctacgc cggacgcatc gtggccggca tcaccggcgc cacaggtgcg   8880

gttgctggcg cctatatcgc cgacatcacc gatggggaag atcgggctcg ccacttcggg   8940

ctcatgagcg cttgtttcgg cgtgggtatg gtggcaggcc ccgtggccgg gggactgttg   9000

ggcgccatct ccttgcatgc accattcctt gcggcggcgg tgctcaacgg cctcaaccta   9060

ctactgggct gcttcctaat gcaggagtcg cataagggag agcgtcgata tggtgcactc   9120

tcagtacaat ctgctctgat gccgcatagt taagccagcc ccgacacccg ccaacacccg   9180

ctgacgcgcc ctgacgggct tgtctgctcc cggcatccgc ttacagacaa gctgtgaccg   9240

tctccgggag ctgcatgtgt cagaggtttt caccgtcatc accgaaacgc gcgagacgaa   9300

agggcctcgt gatacgccta tttttatagg ttaatgtcat gataataatg gtttcttaga   9360
```

```
cgtcaggtgg cacttttcgg ggaaatgtgc gcggaacccc tatttgttta tttttctaaa   9420
tacattcaaa tatgtatccg ctcatgagac aataaccctg ataaatgctt caataatatt   9480
gaaaaaggaa gagtatgagt attcaacatt tccgtgtcgc ccttattccc ttttttgcgg   9540
cattttgcct tcctgttttt gctcacccag aaacgctggt gaaagtaaaa gatgctgaag   9600
atcagttggg tgcacgagtg ggttacatcg aactggatct caacagcggt aagatccttg   9660
agagttttcg ccccgaagaa cgttttccaa tgatgagcac ttttaaagtt ctgctatgtg   9720
gcgcggtatt atcccgtatt gacgccgggc aagagcaact cggtcgccgc atacactatt   9780
ctcagaatga cttggttgag tactcaccag tcacagaaaa gcatcttacg gatggcatga   9840
cagtaagaga attatgcagt gctgccataa ccatgagtga taacactgcg gccaacttac   9900
ttctgacaac gatcggagga ccgaaggagc taaccgcttt tttgcacaac atgggggatc   9960
atgtaactcg ccttgatcgt tgggaaccgg agctgaatga agccatacca aacgacgagc  10020
gtgacaccac gatgcctgta gcaatggcaa caacgttgcg caaactatta actggcgaac  10080
tacttactct agcttcccgg caacaattaa tagactggat ggaggcggat aaagttgcag  10140
gaccacttct gcgctcggcc cttccggctg gctggtttat tgctgataaa tctggagccg  10200
gtgagcgtgg gtctcgcggt atcattgcag cactggggcc agatggtaag ccctcccgta  10260
tcgtagttat ctacacgacg gggagtcagg caactatgga tgaacgaaat agacagatcg  10320
ctgagatagg tgcctcactg attaagcatt ggtaactgtc agaccaagtt tactcatata  10380
tactttagat tgatttaaaa cttcattttt aatttaaaag gatctaggtg aagatccttt  10440
ttgataatct catgaccaaa atcccttaac gtgagttttc gttccactga gcgtcagacc  10500
ccgtagaaaa gatcaaagga tcttcttgag atcctttttt tctgcgcgta atctgctgct  10560
tgcaaacaaa aaaaccaccg ctaccagcgg tggtttgttt gccggatcaa gagctaccaa  10620
ctctttttcc gaaggtaact ggcttcagca gagcgcagat accaaatact gtccttctag  10680
tgtagccgta gttaggccac cacttcaaga actctgtagc accgcctaca tacctcgctc  10740
tgctaatcct gttaccagtg gctgctgcca gtggcgataa gtcgtgtctt accgggttgg  10800
actcaagacg atagttaccg gataaggcgc agcggtcggg ctgaacgggg ggttcgtgca  10860
cacagcccag cttggagcga acgacctaca ccgaactgag atacctacag cgtgagctat  10920
gagaaagcgc cacgcttccc gaagggagaa aggcggacag gtatccggta agcggcaggg  10980
tcggaacagg agagcgcacg agggagcttc caggggggaaa cgcctggtat ctttatagtc  11040
ctgtcgggtt tcgccacctc tgacttgagc gtcgattttt gtgatgctcg tcaggggggc  11100
ggagcctatg gaaaaacgcc agcaacgcgg cctttttacg gttcctggcc ttttgctggc  11160
cttttgctca catgttcttt cctgcgttat cccctgattc tgtggataac cgtattaccg  11220
cctttgagtg agctgatacc gctcgccgca gccgaacgac cgagcgcagc gagtcagtga  11280
gcgaggaagc ggaagagcgc ccaatacgca aaccgcctct ccccgcgcgt tggccgattc  11340
attaatgcag ctgtggaatg tgtgtcagtt agggtgtgga aagtccccag gctccccagc  11400
aggcagaagt atgcaaagca tgcatctcaa ttagtcagca accaggtgtg gaaagtcccc  11460
aggctcccca gcaggcagaa gtatgcaaag catgcatctc aattagtcag caaccatagt  11520
cccgccccta actccgccca tcccgcccct aactccgccc agttccgccc attctccgcc  11580
ccatggctga ctaatttttt ttatttatgc agaggccgag gccgcctcgg cctctgagct  11640
attccagaag tagtgaggag gcttttttgg aggcctaggc ttttgcaaaa agcttggaca  11700
```

```
caagacaggc ttgcgagata tgtttgagaa taccacttta tcccgcgtca gggagaggca  11760

gtgcgtaaaa agacgcggac tcatgtgaaa tactggtttt tagtgcgcca gatctctata  11820

atctcgcgca acctattttc ccctcgaaca ctttttaagc cgtagataaa caggctggga  11880

cacttcacat gagcgaaaaa tacatcgtca cctgggacat gttgcagatc catgcacgta  11940

aactcgcaag ccgactgatg ccttctgaac aatggaaagg cattattgcc gtaagccgtg  12000

gcggtctggt accgggtgcg ttactggcgc gtgaactggg tattcgtcat gtcgataccg  12060

tttgtatttc cagctacgat cacgacaacc agcgcgagct taaagtgctg aaacgcgcag  12120

aaggcgatgg cgaaggcttc atcgttattg atgacctggt ggataccggt ggtactgcgg  12180

ttgcgattcg tgaaatgtat ccaaaagcgc actttgtcac catcttcgca aaaccggctg  12240

gtcgtccgct ggttgatgac tatgttgttg atatcccgca agatacctgg attgaacagc  12300

cgtgggatat gggcgtcgta ttcgtcccgc caatctccgg tcgctaatct tttcaacgcc  12360

tggcactgcc gggcgttgtt ctttttaact tcaggcgggt tacaatagtt tccagtaagt  12420

attctggagg ctgcatccat gacacaggca aacctgagcg aaaccctgtt caaaccccgc  12480

tttaaacatc ctgaaacctc gacgctagtc cgccgcttta atcacggcgc acaaccgcct  12540

gtgcagtcgg cccttgatgg taaaaccatc cctcactggt atcgcatgat taaccgtctg  12600

atgtggatct ggcgcggcat tgacccacgc gaaatcctcg acgtccaggc acgtattgtg  12660

atgagcgatg ccgaacgtac cgacgatgat ttatacgata cggtgattgg ctaccgtggc  12720

ggcaactgga tttatgagtg ggccccggat ctttgtgaag gaaccttact tctgtggtgt  12780

gacataattg gacaaactac ctacagagat ttaaagctct aaggtaaata taaaattttt  12840

aagtgtataa tgtgttaaac tactgattct aattgtttgt gtattttaga ttccaaccta  12900

tggaactgat gaatgggagc agtggtggaa tgcctttaat gaggaaaacc tgttttgctc  12960

agaagaaatg ccatctagtg atgatgaggc tactgctgac tctcaacatt ctactcctcc  13020

aaaaaagaag agaaaggtag aagaccccaa ggactttcct tcagaattgc taagtttttt  13080

gagtcatgct gtgtttagta atagaactct tgcttgcttt gctatttaca ccacaaagga  13140

aaaagctgca ctgctataca agaaaattat ggaaaaatat tctgtaacct ttataagtag  13200

gcataacagt tataatcata acatactgtt ttttcttact ccacacaggc atagagtgtc  13260

tgctattaat aactatgctc aaaaattgtg tacctttagc tttttaattt gtaaaggggt  13320

taataaggaa tatttgatgt atagtgcctt gactagagat cataatcagc cataccacat  13380

ttgtagaggt tttacttgct ttaaaaaacc tcccacacct cccccctgaac ctgaaacata  13440

aaatgaatgc aattgttgtt gtt                                           13463
```

<210> SEQ ID NO 23
<211> LENGTH: 8922
<212> TYPE: DNA
<213> ORGANISM: Artificial Sequence
<220> FEATURE:
<223> OTHER INFORMATION: Synthetic Construct

<400> SEQUENCE: 23

```
aatgtagtct tatgcaatac tcttgtagtc ttgcaacatg gtaacgatga gttagcaaca     60

tgccttacaa ggagagaaaa agcaccgtgc atgccgattg gtggaagtaa ggtggtacga    120

tcgtgcctta ttaggaaggc aacagacggg tctgacatgg attggacgaa ccactgaatt    180

gccgcattgc agagatattg tatttaagtg cctagctcga tacataaacg ggtctctctg    240

gttagaccag atctgagcct gggagctctc tggctaacta gggaacccac tgcttaagcc    300
```

-continued

```
tcaataaagc ttgccttgag tgcttcaagt agtgtgtgcc cgtctgttgt gtgactctgg    360
taactagaga tccctcagac ccttttagtc agtgtggaaa atctctagca gtggcgcccg    420
aacagggact tgaaagcgaa agggaaacca gaggagctct ctcgacgcag gactcggctt    480
gctgaagcgc gcacggcaag aggcgagggg cggcgactgg tgagtacgcc aaaaattttg    540
actagcggag gctagaagga gagagatggg tgcgagagcg tcagtattaa gcgggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620
agtttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgatt   1800
aacttttaaa agaaaagggg ggattggggg gtacagtgca ggggaaagaa tagtagacat   1860
aatagcaaca gacatacaaa ctaaagaatt acaaaaacaa attacaaaaa ttcaaaattt   1920
tatcgatgtc gacgttaacg ctagtgatat caactttgta tagaaaagtt gaacgagaaa   1980
cgtaaaatga tataaatatc aatatattaa attagatttt gcataaaaaa cagactacat   2040
aatactgtaa aacacaacat atccagtcac tatggcggcc gcattaggca ccccaggctt   2100
tacactttat gcttccggct cgtataatgt gtggattttg agttaggatc cgtcgagatt   2160
ttcaggagct aaggaagcta aaatggagaa aaaaatcact ggatatacca ccgttgatat   2220
atcccaatgg catcgtaaag aacattttga ggcatttcag tcagttgctc aatgtaccta   2280
taaccagacc gttcagctgg atattacggc ctttttaaag accgtaaaga aaaataagca   2340
caagttttat ccggccttta ttcacattct tgcccgcctg atgaatgctc atccggaatt   2400
ccgtatggca atgaaagacg gtgagctggt gatatgggat agtgttcacc cttgttacac   2460
cgttttccat gagcaaactg aaacgttttc atcgctctgg agtgaatacc acgacgattt   2520
ccggcagttt ctacacatat attcgcaaga tgtggcgtgt tacggtgaaa acctggccta   2580
tttccctaaa gggtttattg agaatatgtt tttcgtctca gccaatccct gggtgagttt   2640
```

```
caccagtttt gatttaaacg tggccaatat ggacaacttc ttcgcccccg ttttcaccat   2700
gggcaaatat tatacgcaag gcgacaaggt gctgatgccg ctggcgattc aggttcatca   2760
tgccgtttgt gatggcttcc atgtcggcag aatgcttaat gaattacaac agtactgcga   2820
tgagtggcag ggcggggcgt aaagatctgg atccggctta ctaaaagcca gataacagta   2880
tgcgtatttg cgcgctgatt tttgcggtat aagaatatat actgatatgt atacccgaag   2940
tatgtcaaaa agaggtatgc tatgaagcag cgtattacag tgacagttga cagcgacagc   3000
tatcagttgc tcaaggcata tatgatgtca atatctccgg tctggtaagc acaaccatgc   3060
agaatgaagc ccgtcgtctg cgtgccgaac gctggaaagc ggaaaatcag gaagggatgg   3120
ctgaggtcgc ccggtttatt gaaatgaacg gctcttttgc tgacgagaac aggggctggt   3180
gaaatgcagt ttaaggttta cacctataaa agagagagcc gttatcgtct gtttgtggat   3240
gtacagagtg atattattga cacgcccggg cgacggatgg tgatccccct ggccagtgca   3300
cgtctgctgt cagataaagt ctcccgtgaa ctttacccgg tggtgcatat cggggatgaa   3360
agctggcgca tgatgaccac cgatatggcc agtgtgccgg tctccgttat cggggaagaa   3420
gtggctgatc tcagccaccg cgaaaatgac atcaaaaacg ccattaacct gatgttctgg   3480
ggaatataaa tgtcaggctc ccttatacac agccagtctg caggtcgacc atagtgactg   3540
gatatgttgt gttttacagt attatgtagt ctgtttttta tgcaaaatct aatttaatat   3600
attgatattt atatcatttt acgtttctcg ttcagctttc ttgtacaaag tggttgatat   3660
ccagcacagt ggcggccgct cgagtctaga gggcccgcgg ttcgaaggta agcctatccc   3720
taaccctctc ctcggtctcg attctacgcg taccggttag taatgatcga caatcaacct   3780
ctggattaca aaatttgtga aagattgact ggtattctta actatgttgc tccttttacg   3840
ctatgtggat acgctgcttt aatgcctttg tatcatgcta ttgcttcccg tatggctttc   3900
attttctcct ccttgtataa atcctggttg ctgtctcttt atgaggagtt gtggcccgtt   3960
gtcaggcaac gtggcgtggt gtgcactgtg tttgctgacg caacccccac tggttggggc   4020
attgccacca cctgtcagct cctttccggg actttcgctt tccccctccc tattgccacg   4080
gcggaactca tcgccgcctg ccttgcccgc tgctggacag gggctcggct gttgggcact   4140
gacaattccg tggtgttgtc ggggaagctg acgtcctttc catggctgct cgcctgtgtt   4200
gccacctgga ttctgcgcgg gacgtccttc tgctacgtcc cttcggccct caatccagcg   4260
gaccttcctt cccgcggcct gctgccggct ctgcggcctc ttccgcgtct tcgccttcgc   4320
cctcagacga gtcggatctc cctttgggcc gcctccccgc ctggcgatgg tacctaccgg   4380
gtaggggagg cgcttttccc aaggcagtct ggagcatgcg ctttagcagc cccgctgggc   4440
acttggcgct acacaagtgg cctctggcct cgcacacatt ccacatccac cggtaggcgc   4500
caaccggctc cgttctttgg tggccccttc gcgccacctt ctactcctcc cctagtcagg   4560
aagttccccc ccgccccgca gctcgcgtcg tgcaggacgt gacaaatgga agtagcacgt   4620
ctcactagtc tcgtgcagat ggacagcacc gctgagcaat ggaagcgggt aggcctttgg   4680
ggcagcggcc aatagcagct ttgctccttc gctttctggg ctcagaggct gggaaggggt   4740
gggtccgggg gcgggctcag gggcgggctc aggggcgggg cgggcgcccg aaggtcctcc   4800
ggaggcccgg cattctgcac gcttcaaaag cgcacgtctg ccgcgctgtt ctcctcttcc   4860
tcatctccgg gcctttcgac tctagacacg tgttgacaat taatcatcgg catagtatat   4920
cggcatagta taatacgaca aggtgaggaa ctaaaccatg gccaagcctt tgtctcaaga   4980
agaatccacc ctcattgaaa gagcaacggc tacaatcaac agcatcccca tctctgaaga   5040
```

-continued

```
ctacagcgtc gccagcgcag ctctctctag cgacggccgc atcttcactg gtgtcaatgt   5100
atatcatttt actgggggac cttgtgcaga actcgtggtg ctgggcactg ctgctgctgc   5160
ggcagctggc aacctgactt gtatcgtcgc gatcggaaat gagaacaggg gcatcttgag   5220
cccctgcgga cggtgccgac aggtgcttct cgatctgcat cctgggatca aagccatagt   5280
gaaggacagt gatggacagc cgacggcagt tgggattcgt gaattgctgc cctctggtta   5340
tgtgtgggag ggctaagcac aattcgagct cggtaccttt aagaccaatg acttacaagg   5400
cagctgtaga tcttagccac tttttaaaag aaaagggggg actggaaggg ctaattcact   5460
cccaacgaag acaagatctg ctttttgctt gtactgggtc tctctggtta gaccagatct   5520
gagcctggga gctctctggc taactaggga acccactgct taagcctcaa taaagcttgc   5580
cttgagtgct tcaagtagtg tgtgcccgtc tgttgtgtga ctctggtaac tagagatccc   5640
tcagaccctt ttagtcagtg tggaaaatct ctagcagtag tagttcatgt catcttatta   5700
ttcagtattt ataacttgca aagaaatgaa tatcagagag tgagaggaac ttgtttattg   5760
cagcttataa tggttacaaa taaagcaata gcatcacaaa tttcacaaat aaagcatttt   5820
tttcactgca ttctagttgt ggtttgtcca aactcatcaa tgtatcttat catgtctggc   5880
tctagctatc ccgcccctaa ctccgcccat cccgccccta actccgccca gttccgccca   5940
ttctccgccc catggctgac taattttttt tatttatgca gaggccgagg ccgcctcggc   6000
ctctgagcta ttccagaagt agtgaggagg cttttttgga ggcctaggga cgtacccaat   6060
tcgccctata gtgagtcgta ttacgcgcgc tcactggccg tcgttttaca acgtcgtgac   6120
tgggaaaacc ctggcgttac ccaacttaat cgccttgcag cacatccccc tttcgccagc   6180
tggcgtaata gcgaagaggc ccgcaccgat cgcccttccc aacagttgcg cagcctgaat   6240
ggcgaatggg acgcgccctg tagcggcgca ttaagcgcgg cgggtgtggt ggttacgcgc   6300
agcgtgaccg ctacacttgc cagcgcccta gcgcccgctc ctttcgcttt cttcccttcc   6360
tttctcgcca cgttcgccgg ctttccccgt caagctctaa atcgggggct ccctttaggg   6420
ttccgattta gtgctttacg gcacctcgac cccaaaaaac ttgattaggg tgatggttca   6480
cgtagtgggc catcgccctg atagacggtt tttcgccctt tgacgttgga gtccacgttc   6540
tttaatagtg gactcttgtt ccaaactgga acaacactca accctatctc ggtctattct   6600
tttgatttat aagggatttt gccgatttcg gcctattggt taaaaaatga gctgatttaa   6660
caaaaattta acgcgaattt taacaaaata ttaacgctta caatttaggt ggcacttttc   6720
ggggaaatgt gcgcggaacc cctatttgtt tatttttcta aatacattca aatatgtatc   6780
cgctcatgag acaataaccc tgataaatgc ttcaataata ttgaaaaagg aagagtatga   6840
gtattcaaca tttccgtgtc gcccttattc ccttttttgc ggcattttgc cttcctgttt   6900
ttgctcaccc agaaacgctg gtgaaagtaa aagatgctga agatcagttg ggtgcacgag   6960
tgggttacat cgaactggat ctcaacagcg gtaagatcct tgagagtttt cgccccgaag   7020
aacgttttcc aatgatgagc acttttaaag ttctgctatg tggcgcggta ttatcccgta   7080
ttgacgccgg gcaagagcaa ctcggtcgcc gcatacacta ttctcagaat gacttggttg   7140
agtactcacc agtcacagaa aagcatctta cggatggcat gacagtaaga gaattatgca   7200
gtgctgccat aaccatgagt gataacactg cggccaactt acttctgaca acgatcggag   7260
gaccgaagga gctaaccgct tttttgcaca acatggggga tcatgtaact cgccttgatc   7320
gttgggaacc ggagctgaat gaagccatac caaacgacga gcgtgacacc acgatgcctg   7380
```

```
tagcaatggc aacaacgttg cgcaaactat taactggcga actacttact ctagcttccc   7440

ggcaacaatt aatagactgg atggaggcgg ataaagttgc aggaccactt ctgcgctcgg   7500

cccttccggc tggctggttt attgctgata aatctggagc cggtgagcgt gggtctcgcg   7560

gtatcattgc agcactgggg ccagatggta agccctcccg tatcgtagtt atctacacga   7620

cggggagtca ggcaactatg gatgaacgaa atagacagat cgctgagata ggtgcctcac   7680

tgattaagca ttggtaactg tcagaccaag tttactcata tatactttag attgatttaa   7740

aacttcattt ttaatttaaa aggatctagg tgaagatcct ttttgataat ctcatgacca   7800

aaatccctta acgtgagttt tcgttccact gagcgtcaga ccccgtagaa aagatcaaag   7860

gatcttcttg agatcctttt tttctgcgcg taatctgctg cttgcaaaca aaaaaaccac   7920

cgctaccagc ggtggtttgt ttgccggatc aagagctacc aactcttttt ccgaaggtaa   7980

ctggcttcag cagagcgcag ataccaaata ctgttcttct agtgtagccg tagttaggcc   8040

accacttcaa gaactctgta gcaccgccta catacctcgc tctgctaatc ctgttaccag   8100

tggctgctgc cagtggcgat aagtcgtgtc ttaccgggtt ggactcaaga cgatagttac   8160

cggataaggc gcagcggtcg ggctgaacgg ggggttcgtg cacacagccc agcttggagc   8220

gaacgaccta caccgaactg agatacctac agcgtgagct atgagaaagc gccacgcttc   8280

ccgaagggag aaaggcggac aggtatccgg taagcggcag ggtcggaaca ggagagcgca   8340

cgagggagct tccaggggga aacgcctggt atctttatag tcctgtcggg tttcgccacc   8400

tctgacttga gcgtcgattt ttgtgatgct cgtcaggggg gcggagccta tggaaaaacg   8460

ccagcaacgc ggccttttta cggttcctgg ccttttgctg gccttttgct cacatgttct   8520

ttcctgcgtt atcccctgat tctgtggata accgtattac cgcctttgag tgagctgata   8580

ccgctcgccg cagccgaacg accgagcgca gcgagtcagt gagcgaggaa gcggaagagc   8640

gcccaatacg caaaccgcct ctccccgcgc gttggccgat tcattaatgc agctggcacg   8700

acaggtttcc cgactggaaa gcgggcagtg agcgcaacgc aattaatgtg agttagctca   8760

ctcattaggc accccaggct ttacacttta tgcttccggc tcgtatgttg tgtggaattg   8820

tgagcggata acaatttcac acaggaaaca gctatgacca tgattacgcc aagcgcgcaa   8880

ttaaccctca ctaaagggaa caaaagctgg agctgcaagc tt                      8922
```

<210> SEQ ID NO 24
<211> LENGTH: 8120
<212> TYPE: DNA
<213> ORGANISM: Artificial Sequence
<220> FEATURE:
<223> OTHER INFORMATION: Synthetic Construct

<400> SEQUENCE: 24

```
ttgtacaaag tggttgatat ccagcacagt ggcggccgct cgagtctaga gggcccgcgg     60

ttcgaaggta agcctatccc taaccctctc ctcggtctcg attctacgcg taccggttag    120

taatgatcga caatcaacct ctggattaca aaatttgtga aagattgact ggtattctta    180

actatgttgc tccttttacg ctatgtggat acgctgcttt aatgcctttg tatcatgcta    240

ttgcttcccg tatggctttc attttctcct ccttgtataa atcctggttg ctgtctcttt    300

atgaggagtt gtggcccgtt gtcaggcaac gtggcgtggt gtgcactgtg tttgctgacg    360

caacccccac tggttggggc attgccacca cctgtcagct cctttccggg actttcgctt    420

tccccctccc tattgccacg gcggaactca tcgccgcctg ccttgcccgc tgctggacag    480

gggctcggct gttgggcact gacaattccg tggtgttgtc ggggaagctg acgtcctttc    540
```

```
catggctgct cgcctgtgtt gccacctgga ttctgcgcgg gacgtccttc tgctacgtcc    600
cttcggccct caatccagcg gaccttcctt cccgcggcct gctgccggct ctgcggcctc    660
ttccgcgtct tcgccttcgc cctcagacga gtcggatctc cctttgggcc gcctccccgc    720
ctggcgatgg tacctaccgg gtaggggagg cgcttttccc aaggcagtct ggagcatgcg    780
ctttagcagc cccgctgggc acttggcgct acacaagtgg cctctggcct cgcacacatt    840
ccacatccac cggtaggcgc caaccggctc cgttctttgg tggccccttc gcgccacctt    900
ctactcctcc cctagtcagg aagttccccc ccgccccgca gctcgcgtcg tgcaggacgt    960
gacaaatgga agtagcacgt ctcactagtc tcgtgcagat ggacagcacc gctgagcaat   1020
ggaagcgggt aggcctttgg ggcagcggcc aatagcagct ttgctccttc gctttctggg   1080
ctcagaggct gggaaggggt gggtccgggg gcgggctcag gggcgggctc aggggcgggg   1140
cgggcgcccg aaggtcctcc ggaggcccgg cattctgcac gcttcaaaag cgcacgtctg   1200
ccgcgctgtt ctcctcttcc tcatctccgg gcctttcgac tctagacacg tgttgacaat   1260
taatcatcgg catagtatat cggcatagta taatacgaca aggtgaggaa ctaaaccatg   1320
gccaagcctt tgtctcaaga agaatccacc ctcattgaaa gagcaacggc tacaatcaac   1380
agcatcccca tctctgaaga ctacagcgtc gccagcgcag ctctctctag cgacggccgc   1440
atcttcactg gtgtcaatgt atatcatttt actgggggac cttgtgcaga actcgtggtg   1500
ctgggcactg ctgctgctgc ggcagctggc aacctgactt gtatcgtcgc gatcggaaat   1560
gagaacaggg gcatcttgag cccctgcgga cggtgccgac aggtgcttct cgatctgcat   1620
cctgggatca aagccatagt gaaggacagt gatggacagc cgacggcagt tgggattcgt   1680
gaattgctgc cctctggtta tgtgtgggag ggctaagcac aattcgagct cggtaccttt   1740
aagaccaatg acttacaagg cagctgtaga tcttagccac tttttaaaag aaaagggggg   1800
actggaaggg ctaattcact cccaacgaag acaagatctg ctttttgctt gtactgggtc   1860
tctctggtta gaccagatct gagcctggga gctctctggc taactaggga acccactgct   1920
taagcctcaa taaagcttgc cttgagtgct tcaagtagtg tgtgcccgtc tgttgtgtga   1980
ctctggtaac tagagatccc tcagaccctt ttagtcagtg tggaaaatct ctagcagtag   2040
tagttcatgt catcttatta ttcagtattt ataacttgca aagaaatgaa tatcagagag   2100
tgagaggaac ttgtttattg cagcttataa tggttacaaa taaagcaata gcatcacaaa   2160
tttcacaaat aaagcatttt tttcactgca ttctagttgt ggtttgtcca aactcatcaa   2220
tgtatcttat catgtctggc tctagctatc ccgcccctaa ctccgcccat cccgccccta   2280
actccgccca gttccgccca ttctccgccc catggctgac taattttttt tatttatgca   2340
gaggccgagg ccgcctcggc ctctgagcta ttccagaagt agtgaggagg cttttttgga   2400
ggcctaggga cgtacccaat tcgccctata gtgagtcgta ttacgcgcgc tcactggccg   2460
tcgttttaca acgtcgtgac tgggaaaacc ctggcgttac ccaacttaat cgccttgcag   2520
cacatccccc tttcgccagc tggcgtaata gcgaagaggc ccgcaccgat cgcccttccc   2580
aacagttgcg cagcctgaat ggcgaatggg acgcgccctg tagcggcgca ttaagcgcgg   2640
cgggtgtggt ggttacgcgc agcgtgaccg ctacacttgc cagcgcccta gcgcccgctc   2700
ctttcgcttt cttcccttcc tttctcgcca cgttcgccgg ctttccccgt caagctctaa   2760
atcgggggct ccctttaggg ttccgattta gtgctttacg gcacctcgac cccaaaaaac   2820
ttgattaggg tgatggttca cgtagtgggc catcgccctg atagacggtt tttcgccctt   2880
```

-continued

```
tgacgttgga gtccacgttc tttaatagtg gactcttgtt ccaaactgga acaacactca   2940
accctatctc ggtctattct tttgatttat aagggatttt gccgatttcg gcctattggt   3000
taaaaaatga gctgatttaa caaaaattta acgcgaattt taacaaaata ttaacgctta   3060
caatttaggt ggcacttttc ggggaaatgt gcgcggaacc cctatttgtt tatttttcta   3120
aatacattca aatatgtatc cgctcatgag acaataaccc tgataaatgc ttcaataata   3180
ttgaaaaagg aagagtatga gtattcaaca tttccgtgtc gcccttattc ccttttttgc   3240
ggcattttgc cttcctgttt ttgctcaccc agaaacgctg gtgaaagtaa aagatgctga   3300
agatcagttg ggtgcacgag tgggttacat cgaactggat ctcaacagcg gtaagatcct   3360
tgagagtttt cgccccgaag aacgttttcc aatgatgagc acttttaaag ttctgctatg   3420
tggcgcggta ttatcccgta ttgacgccgg gcaagagcaa ctcggtcgcc gcatacacta   3480
ttctcagaat gacttggttg agtactcacc agtcacagaa aagcatctta cggatggcat   3540
gacagtaaga gaattatgca gtgctgccat aaccatgagt gataacactg cggccaactt   3600
acttctgaca acgatcggag gaccgaagga gctaaccgct tttttgcaca acatggggga   3660
tcatgtaact cgccttgatc gttgggaacc ggagctgaat gaagccatac caaacgacga   3720
gcgtgacacc acgatgcctg tagcaatggc aacaacgttg cgcaaactat taactggcga   3780
actacttact ctagcttccc ggcaacaatt aatagactgg atggaggcgg ataaagttgc   3840
aggaccactt ctgcgctcgg cccttccggc tggctggttt attgctgata aatctggagc   3900
cggtgagcgt gggtctcgcg gtatcattgc agcactgggg ccagatggta agccctcccg   3960
tatcgtagtt atctacacga cggggagtca ggcaactatg gatgaacgaa atagacagat   4020
cgctgagata ggtgcctcac tgattaagca ttggtaactg tcagaccaag tttactcata   4080
tatactttag attgatttaa aacttcattt ttaatttaaa aggatctagg tgaagatcct   4140
ttttgataat ctcatgacca aaatccctta acgtgagttt tcgttccact gagcgtcaga   4200
ccccgtagaa aagatcaaag gatcttcttg agatcctttt tttctgcgcg taatctgctg   4260
cttgcaaaca aaaaaaccac cgctaccagc ggtggtttgt ttgccggatc aagagctacc   4320
aactcttttt ccgaaggtaa ctggcttcag cagagcgcag ataccaaata ctgttcttct   4380
agtgtagccg tagttaggcc accacttcaa gaactctgta gcaccgccta catacctcgc   4440
tctgctaatc ctgttaccag tggctgctgc cagtggcgat aagtcgtgtc ttaccgggtt   4500
ggactcaaga cgatagttac cggataaggc gcagcggtcg ggctgaacgg ggggttcgtg   4560
cacacagccc agcttggagc gaacgaccta caccgaactg agatacctac agcgtgagct   4620
atgagaaagc gccacgcttc ccgaagggag aaaggcggac aggtatccgg taagcggcag   4680
ggtcggaaca ggagagcgca cgagggagct tccaggggga aacgcctggt atctttatag   4740
tcctgtcggg tttcgccacc tctgacttga gcgtcgattt ttgtgatgct cgtcaggggg   4800
gcggagccta tggaaaaacg ccagcaacgc ggccttttta cggttcctgg ccttttgctg   4860
gccttttgct cacatgttct ttcctgcgtt atcccctgat tctgtggata accgtattac   4920
cgcctttgag tgagctgata ccgctcgccg cagccgaacg accgagcgca gcgagtcagt   4980
gagcgaggaa gcggaagagc gcccaatacg caaaccgcct ctccccgcgc gttggccgat   5040
tcattaatgc agctggcacg acaggtttcc cgactggaaa gcgggcagtg agcgcaacgc   5100
aattaatgtg agttagctca ctcattaggc accccaggct ttacacttta tgcttccggc   5160
tcgtatgttg tgtggaattg tgagcggata acaatttcac acaggaaaca gctatgacca   5220
tgattacgcc aagcgcgcaa ttaaccctca ctaaagggaa caaaagctgg agctgcaagc   5280
```

-continued

```
ttaatgtagt cttatgcaat actcttgtag tcttgcaaca tggtaacgat gagttagcaa   5340
catgccttac aaggagagaa aaagcaccgt gcatgccgat tggtggaagt aaggtggtac   5400
gatcgtgcct tattaggaag gcaacagacg ggtctgacat ggattggacg aaccactgaa   5460
ttgccgcatt gcagagatat tgtatttaag tgcctagctc gatacataaa cgggtctctc   5520
tggttagacc agatctgagc ctgggagctc tctggctaac tagggaaccc actgcttaag   5580
cctcaataaa gcttgccttg agtgcttcaa gtagtgtgtg cccgtctgtt gtgtgactct   5640
ggtaactaga gatccctcag acccttttag tcagtgtgga aaatctctag cagtggcgcc   5700
cgaacaggga cttgaaagcg aaagggaaac cagaggagct ctctcgacgc aggactcggc   5760
ttgctgaagc gcgcacggca agaggcgagg ggcggcgact ggtgagtacg ccaaaaattt   5820
tgactagcgg aggctagaag gagagagatg ggtgcgagag cgtcagtatt aagcggggga   5880
gaattagatc gcgatgggaa aaaattcggt taaggccagg gggaaagaaa aaatataaat   5940
taaaacatat agtatgggca agcagggagc tagaacgatt cgcagttaat cctggcctgt   6000
tagaaacatc agaaggctgt agacaaatac tgggacagct acaaccatcc cttcagacag   6060
gatcagaaga acttagatca ttatataata cagtagcaac cctctattgt gtgcatcaaa   6120
ggatagagat aaaagacacc aaggaagctt tagacaagat agaggaagag caaaacaaaa   6180
gtaagaccac cgcacagcaa gcggccgctg atcttcagac ctggaggagg agatatgagg   6240
gacaattgga gaagtgaatt atataaatat aaagtagtaa aaattgaacc attaggagta   6300
gcacccacca aggcaaagag aagagtggtg cagagagaaa aaagagcagt gggaatagga   6360
gctttgttcc ttgggttctt gggagcagca ggaagcacta tgggcgcagc gtcaatgacg   6420
ctgacggtac aggccagaca attattgtct ggtatagtgc agcagcagaa caatttgctg   6480
agggctattg aggcgcaaca gcatctgttg caactcacag tctggggcat caagcagctc   6540
caggcaagaa tcctggctgt ggaaagatac ctaaaggatc aacagctcct ggggatttgg   6600
ggttgctctg gaaaactcat ttgcaccact gctgtgcctt ggaatgctag ttggagtaat   6660
aaatctctgg aacagatttg gaatcacacg acctggatgg agtgggacag agaaattaac   6720
aattacacaa gcttaataca ctccttaatt gaagaatcgc aaaaccagca agaaaagaat   6780
gaacaagaat tattggaatt agataaatgg gcaagtttgt ggaattggtt taacataaca   6840
aattggctgt ggtatataaa attattcata atgatagtag gaggcttggt aggtttaaga   6900
atagtttttg ctgtactttc tatagtgaat agagttaggc agggatattc accattatcg   6960
tttcagaccc acctcccaac cccgagggga cccgacaggc ccgaaggaat agaagaagaa   7020
ggtggagaga gagacagaga cagatccatt cgattagtga acggatctcg acggtatcga   7080
ttaactttta aaagaaaagg ggggattggg gggtacagtg caggggaaag aatagtagac   7140
ataatagcaa cagacataca aactaaagaa ttacaaaaac aaattacaaa aattcaaaat   7200
tttatcgatg tcgacgttaa cgctagtgat atcaactttg tatagaaaag ttgaagcttg   7260
ggagttccgc gttacataac ttacggtaaa tggcccgcct ggctgaccgc ccaacgaccc   7320
ccgcccattg acgtcaataa tgacgtatgt tcccatagta acgccaatag ggactttcca   7380
ttgacgtcaa tgggtggagt atttacggta aactgcccac ttggcagtac atcaagtgta   7440
tcatatgcca agtacgcccc ctattgacgt caatgacggt aaatggcccg cctggcatta   7500
tgcccagtac atgaccttat gggactttcc tacttggcag tacatctacg tattagtcat   7560
cgctattacc atggtgatgc ggttttggca gtacatcaat gggcgtggat agcggtttga   7620
```

-continued

| | |
|---|---|
| ctcacgggga tttccaagtc tccaccccat tgacgtcaat gggagtttgt tttggcacca | 7680 |
| aaatcaacgg gactttccaa aatgtcgtaa caactccgcc ccattgacgc aaatgggcgg | 7740 |
| taggcgtgta cggtgggagg tctatataag cagagctcgt ttagtgaacc gtcagatcgc | 7800 |
| ctggagacgc catccacgct gttttgacct ccatagaaga caccgactct agaggatcca | 7860 |
| ctagtccagt gtggtggaat tctgcagata tcacaagttt gtacaaaaaa gcaggcttta | 7920 |
| aagggaggta gtgagtcgac cagtggatcc tggaggcttg ctgaaggctg tatgctgtcc | 7980 |
| tcacaatcca caaactgggt tttggccact gactgaccca gtttggattg tgaggacagg | 8040 |
| acacaaggcc tgttactagc actcacatgg aacaaatggc ccagatctgg ccgcactcga | 8100 |
| gatatctaga cccagctttc | 8120 |

LRP1 AS KEY RECEPTOR FOR THE TRANSFER OF STERIFIED CHOLESTEROL FROM VERY-LOW-DENSITY LIPOPROTEINS (VLDL) TO ISCHAEMIC CARDIAC MUSCLE

The invention is of interest to the pharmaceutical and chemical sectors and refers to new molecules capable of modulating the mass deposition of cholesterol in cardiomyocytes so that said molecules have clinical application, as they have therapeutic effects by minimizing cardiac alterations of acute myocardial infarction or angina pectoris induced by dyslipidemia or other conditions that occur alongside ischaemia.

BACKGROUND

During ischaemic processes related to acute myocardial infarction or angina pectoris, a lipid accumulation in the myocardium is produced. This fact has not only been observed in test animals (Straeter-Knowlen I M et al, *Circulation* 1996; Chabowski A et al, *FEBS Lett* 2006) but also in patients (Golfbarb J W et al, *Radiology* 2009). Furthermore, there is also experimental evidence showing that dyslipidemia contributes to the exacerbation of cardiac alterations induced by ischaemia in animal models (Osipov R M et al, *Circulation* 2009; Kim E et al, *J Neurosci* 2008). It has recently been demonstrated that high doses of VLDL alter calcium ($Ca^{2+}$) regulation in cardiomyocytes and that these alterations induced by VLDL are exacerbated in situations of hypoxia, with SERCA-2 sarcoplasmic reticulum protein playing a crucial role (Castellano J et al, *J Mol Cell Cardiol* 2011).

Ischaemia as a basis of heart failure results in the condition known as ischaemic cardiomyopathy. Ischaemic cardiomyopathy is with high frequency a result of coronary disease, whose underlying pathology is atherosclerosis (Gersh B J et al, journal 1997). Atherosclerotic plaque evolution produces a progressive imbalance between oxygen supply and demand in the myocardium. The gravest outcome of the atherosclerotic process, infarction, is in 80% of cases due to atherosclerotic plaque rupture, the formation of the thrombus, and the total or partial occlusion of the vessel (Burke A P et al, *Med Clin North America* 2007). Dyslipidemia is a key risk factor in ischaemic cardiomyopathy generation, mainly because of its role at the beginning and in the development of atherosclerosis. In situations of dyslipidemia there is an increase in the influx of lipoproteins towards the arterial intimae, where they are modified by means of oxidation and aggregation through interaction with the proteoglycanes that make up the extracellular matrix (Sartipy P et al, *Circ Res* 2000; Hakala J K et al, *ATVB* 2001). Modified lipoprotein uptake by smooth muscular cells from the vascular wall and macrophages leads to the formation of foam cells in the vascular wall. Low-density lipoprotein receptor-related protein (LRP1) has been identified as a key receptor for uptake of LDL modified by intracellular cholesterol aggregation and accumulation in smooth muscle cells from the vascular wall and macrophages as well as for their transformation into foam cells (Llorente-Cortés V et al, *ATVB* 2000; Llorente-Cortés et al, *ATVB* 2002; Llorente-Cortés et al, *J Lipid Res* 2007, Llorente-Cortés et al, *Cardiovasc Res* 2007). LRP1 is upregulated in advanced atherosclerotic lesions rich in lipids (Luoma J et al, *J Clin Invest* 1994; Llorente-Cortés et al, *Eur J Clin Invest* 2004) and may be considered as a heart disease biomarker as there are clinical trials showing the relationship between LRP1 expression alteration and coronary disease (Handschug K et al, *J Mol Med* 1998; Schulz et al, *Int J Cardiol* 2003). It has also been shown that risk factors relevant for atherosclerosis development such as hypercholesterolemia and hypertension upwards regulate LRP1 expression in the vascular wall (Llorente-Cortés et al, *Circulation* 2002; Sendra J et al, *Cardiovasc Res* 2008). It has later been shown that aggregated LDL uptake by LRP1 regulates the expression and activation of the tissue factor, a main coagulation activator, therefore regulating thrombus formation by means of a RhoA and sphyngomyelin-dependant mechanism (Llorente-Cortés et al, *Circulation* 2004; Camino-López S et al, *Cardiovasc Res* 2007; Camino-López S et al, *J Thromb Haemost* 2009). In addition to all these processes it has been described how LRP1 takes part in the regulation of extracellular matrix composition (Strickland D K et al, *Trends Endocrinol Metab* 2002), may promote receptor internalization (Wu L et al, *J Cell Biochem,* 2005) and regulates the activity of various intracellular signaling proteins (Herz J et al, *J Clin Invest* 2001).

The role of LRP1 in cardiomyocytes and the consequences of alterations in its expression for lipid metabolism are wholly unknown at this time. It is known that lipase lipoprotein present in the surface of cardiomyocytes mediates LDL uptake. Nonetheless, lipase lipoprotein uses a receptor so far unidentified for the selective uptake of cholesterol, and it is not the classic LDL receptor (Yagyu H et al, *J Clin Invest* 2003; Yokoyama M et al, *J Lipid Res* 2007). It has also been demonstrated that LRP1 mediates selective cholesterol uptake in vascular cells (Llorente-Cortés et al, *ATVB* 2006).

Cardiomyocytes accumulate lipids in different pathophysiological conditions, of which processes of acute ischaemia are one (Chabowski A et al, *FEBS Lett* 2006; Goldfarb J W et al, *Radiology* 2009), though the mechanisms by which this occurs are to a large extent unknown. One of the mechanisms participating in triglyceride (TG) accumulation in ischaemic situations is the increase of endogenous TG synthesis due to hypoxia (Boström P et al, *ATVB* 2006). Nonetheless, cardiomyocytes may catch lipids from lipoproteins rich in TG such as VLDL and chylomicrons. It is known that CD36 and lipase lipoprotein participate in the uptake of VLDL fatty acids by cardiomyocytes (Bharadwaj K G et al, *J Biol Chem* 2010). As CD36 is increased in situations of hypoxia (Mwaikambo B R et al, *J Biol Chem* 2009), it is plausible that increased CD36 levels participate in the accumulation of TG observed in the ischaemic heart. Although it is known that the heart may take up cholesterol from VLDL (Bharadawaj K G et al, *J Biol Chem* 2010) and chylomicrons (Fielding C J et al, *J Clin Invest* 1978), the mechanisms involved in the entry of cholesterol into the heart are completely unknown.

Ischaemia is associated with an electromechanical dysfunction and with severe alterations in intracellular calcium dynamics (García-Dorado D et al, *Cardiovasc Res* 2006; Takukder M A et al, *Cardiovasc Res* 2009), key for cardiac functionality. Moreover, it recently has been demonstrated that cardiomyocytes exposed to high doses of VLDL suffer from intracellular lipid accumulation, a decrease in SERCA-2 expression, calcium amplitude and sarcoplasmic reticulum calcium content. These effects were exacerbated by exposing the cultivated myocytes to a hypoxic environment. The results highlight the central role of SERCA-2 in the empowerment by hypoxia of alterations in calcium handling induced by VLDL (Castellano J et al, *JMCC* 2011). It has also recently been described how LRP1 is upregulated by hypoxia in smooth muscular cells from the vascular wall (Castellano J et al, *ATVB* 2011). These data demonstrate the importance of understanding the molecular mechanisms involved in lipid uptake by cardiomyocytes in ischaemic situations and the importance of knowing the role of LRP1 in this process.

Therefore, there is currently a need to develop a method for modulating lipoprotein receptors such as LRP1 to treat and prevent the accumulation of neutral lipids such as cholesteryl ester (CE) in cardiomyocytes during ischaemic events, which would minimize the cardiac alterations of acute myocardial infarction or angina pectoris, induced by dyslipidemia or other conditions that accompany ischaemia.

BRIEF DESCRIPTION OF THE INVENTION

The present invention refers to the identification of a key receptor for the entry of cholesterol into the heart in ischaemic situations, LRP1. It also refers to the design of molecules such as lentiviruses, antibodies or transcription factors capable of modulating the activity of this receptor and therefore preventing cardiac alterations associated with the entry of neutral lipids or cholesterol into cardiomyocytes exposed to acute ischaemia processes such as acute myocardial infarction or angina pectoris or to chronic ischaemia processes.

DETAILED DESCRIPTION OF THE INVENTION

At present, the mechanisms leading to cholesterol accumulation in cardiomyocytes are completely unknown. The present invention demonstrates that in ischaemic situations upwards regulation of the receptor LRP1 in the cardiomyocyte. LRP1 overexpression in ischaemic situations plays a primary role in the transfer of cholesteryl ester from lipoproteins into the cardiomyocyte as well as in the intracellular accumulation of this lipid in the heart. Furthermore, the present invention demonstrates that the modulation of the expression and/or function of LRP1 prevents cholesteryl ester overaccumulation in cardiomyocytes exposed to ischaemia. Therefore, this invention provides new molecules capable of modulating one of the mechanisms leading to the massive deposition of cholesterol in the cardiomyocyte during acute myocardium infarction or other conditions that accompany ischaemia.

In the present invention "acute myocardial infarction" refers to an insufficient blood supply, with tissue damage, in a portion of the heart caused by a blockage in one of the coronary arteries, frequently due to the rupture of a vulnerable atheroma plaque. Ischaemia, hypoxia or deficient oxygen supply resulting from such obstruction produces angina pectoris, which does not produce cardiac tissue death if it is precociously rechanneled, whereas if this anoxia is sustained, myocardial lesioning and eventually necrosis occur, which is to say, infarction.

In the present invention it is demonstrated that in cardiomyocytes exposed to hypoxia, overexpression of the receptor LRP1 occurs in association with an increase in the intracellular levels of one of the neutral lipids, cholesteryl ester. It is also demonstrated that modulation, preferably blockage, of LRP1 overexpression induced by hypoxia makes it possible to slow and/or inhibit (partially or fully) the entry of cholesteryl ester from lipoproteins into the heart.

In the present invention it is demonstrated that in the hearts of patients with ischaemic cardiomyopathy there is a very high expression of receptor LRP1, and that expression of this receptor correlates very significantly with the cholesteryl ester content of the myocardium. This does not occur in patients with idiopathic dilated cardiomyopathy or control subjects. Therefore, this mechanism is specific and is only relevant in ischaemic cardiomyopathy.

In the present invention, low density lipoprotein receptor-related Protein is known as "LRP1", also known as α2-macroglobulin, CD91 or AI316852. Said receptor is codified by gene Mm. 271854 in *Homo sapiens*.

In the present invention the term "ischaemia" or "ischaemic cardiomyopathy (ICM)" refers to a set of alterations in heart functionality present when arteries supplying blood and oxygen to the heart are blocked. There is generally an accumulation of cholesterol and other substances called plaque in the arteries that supply oxygen to myocardial tissue. Over time, the myocardium does not work well and it is more difficult for the heart to fill up and to pump blood. Ischaemia is a common cause of cardiac congestive insufficiency. Patients with this condition may have had a heart attack, angina or unstable angina at some time and it is possible that some patients may not have noticed any previous symptoms. In these patients lipids have been found in the penumbra zone (periphery of the area of infarction), though the mechanisms involved in these accumulations are unknown at this time. What is known is that these lipids are involved in inducing severe alterations in calcium metabolism and cardiac remodeling, keys to cardiac functionality.

In the present invention idiopathic dilated cardiomyopathy refers to cardiac muscle illnesses in which the structure and function of the myocardium are altered in absence of coronary illness, hypertension, valvulopathies, or congenital heart defects which explain said anomalies. Among the various myocardiopathies, dilated myocardiopathy (DMC) is defined by the presence of dilatation and systolic dysfunction affecting the left ventricle or both ventricles.

The present invention also refers to a method for avoiding cholesteryl ester accumulation in cardiomyocytes, characterized in that the pharmaceutical composition comprises at least one LRP1 expression and/or function modulator agent. Preferably said expression and/or function modulator agent is selected from the following group: lentivirus, antibody and transcription factor. Said agent is preferably selected from the group below:

a) agents which modulate the expression of LRP1, on a transcriptional level, such as transcription factors (HIF-1alpha (see example 8), SREBPs or others), specific siRNAs released to cells, or activating or inhibitory molecules of the degradation pathway of LRP1 (see example 9); and/or b) agents which modulate the function of LRP1, such as molecules capable of specifically inhibiting the cholesterol uptake function of LRP1.

In the present invention the term "transcription factors" defined in a) refers to those factors that are able to respectively increase or decrease LRP1 expression.

In the present invention the term "specific siRNAs released to cells" defined in a) refers to those siRNAs for inhibiting LRP1 expression that can be released to the cells by lentiviruses and by other means such as electroporation, which are widely known in the state of the art.

In the present invention the term "activating or inhibitory molecules of the degradation pathway of LRP1" defined in a) refers to those molecules described in the ubiquitin-proteasome system.

In the present invention the term "molecules capable of specifically inhibiting the cholesterol uptake function of LRP1" defined in b) refers to those molecules, preferably proteins, which are able to compete with LRP1 in the binding of lipoprotein ligands, such as specific LRP1—monoclonal or polyclonal- or peptides, more concretely, peptides isolated from aminoacids sequence cluster II from the alpha chain of LRP1 protein (SEQ. ID No: 19). In a more preferable embodiment of the invention, said molecules prevent against the pathophysiological function of LRP1 without altering its essential functions.

In the present invention is described an agent that modulates the expression and/or function of the protein LRP1 is described, which is a protein which competes with LRP1 in binding lipoprotein ligands, more precisely it is a specific antibody from an aminoacid sequence or a peptide comprised in cluster II of the alpha chain of the protein LRP1 (SEQ. ID No: 19), and more precisely a specific polyclonal antibody from an aminoacid sequence or peptide which belongs to the following group (see Examples 10 and 11):

peptide P1 (SEQ ID No: 13),
peptide P2 (SEQ ID No: 14), and
peptide P3 (SEQ ID No: 15).

Those skilled in the art of biotechnology and molecular biology and with the information described within the present invention may obtain a specific monoclonal antibody from an aminoacid sequence or peptide comprised in cluster II of the alpha chain of the protein LRP1 (SEQ ID No: 19) and more precisely a specific monoclonal antibody from an aminoacid sequence or peptide which belongs to the following group: peptide P1 (SEQ ID No 13), peptide P2 (SEQ ID No: 14) and peptide P3 (SEQ ID No: 15). Therefore, another object of the invention is constituted by a monoclonal antibody that modulates the expression and/or function of the protein LRP1 that is specific to a sequence of aminoacids or peptide comprised in cluster II of the alpha chain of the protein LRP1 (SEQ ID No: 19), or more precisely specific to a peptide which belongs to the following group:

peptide P1 (SEQ ID No: 13),
peptide P2 (SEQ ID No: 14), and
peptide P3 (SEQ ID No: 15).

Furthermore, the peptides described in the present invention, which are useful for obtaining an antibody—whether polyclonal or monoclonal—that modulates the function of protein LRP1 which may be obtained from an aminoacid sequence or a peptide comprised in cluster II of the alpha chain of the protein LRP1 (SEQ ID No: 19), and more precisely the peptides P1 (SEQ ID No: 13), P2 (SEQ ID No: 14) and P3 (SEQ ID No: 15), constitute another particular object of the present invention.

The present invention also refers to a pharmaceutical composition characterized in that it comprises at least one LRP1 expression modulator agent and/or one LRP1 function modulator agent defined above to control the expression of lipoprotein receptors such as VLDLR, LDLR or LRP1 during acute myocardial infarction or other clinical conditions which accompany ischaemia, hypoxia or deficient oxygen supply, which pharmaceutical composition is preferably characterized in that it comprises an expression modulator agent and/or an LRP1 function modulator agent defined above for blocking LRP1 expression during ischaemia.

The present invention also refers to the use of a pharmaceutical composition defined above to regulate the accumulation of neutral lipids such as cholesteryl ester, triglycerides or free cholesterol in cardiomyocytes of a patient with an acute myocardial infarction or other clinical condition which accompanies ischaemia, hypoxia or deficient oxygen supply such as cardiac insufficiency, ischaemic cardiomyopathy or idiopathic dilated cardiomyopathy.

The present invention refers to a method for regulating the accumulation of neutral lipids such as cholesteryl ester, triglycerides or free cholesterol accumulation in cardiomyocytes, characterized by administering to a patient a therapeutically effective amount of a pharmaceutical composition to control the expression of lipoprotein receptors such as VLDLR, LDLR or LRP1 during an acute myocardial infarction or other clinical condition which accompanies ischaemia, hypoxia or deficient oxygen supply such as cardiac insufficiency, ischaemic card iomyopathy or idiopathic dilated card iomyopathy.

The present invention also refers to a method for avoiding cholesteryl ester accumulation in cardiomyocytes, characterized by administering to the patient a therapeutically effective amount of a pharmaceutical composition to block LRP1 expression during ischaemia, the patient preferably suffering from ischaemic cardiomyopathy.

A preferred embodiment of the invention refers to the use of said pharmaceutical composition defined above to avoid, slow, partially or totally inhibit cholesteryl ester accumulation in cardiomyocytes of a patient suffering or who has suffered from ischaemic cardiomyopathy.

The present invention also protects a method for the treatment and/or prevention of cardiac alterations associated with the entry of neutral lipids or cholesterol into cardiomyocytes exposed to acute ischaemia processes such as acute myocardial infarction or angina pectoris, or to chronic ischaemia.

Finally, the present invention protects the use of molecules capable of modulating lipoprotein receptors such as VLDLR, LDLR or LRP1 in the manufacturing of a medicine used to prevent and/or treat cardiac alterations associated with mass neutral lipid deposition in cardiomyocytes during acute myocardium infarction or other clinical situations which accompany ischaemia processes.

Throughout the description and the claims, the word "comprises" and its variants is not intended to exclude other technical characteristics, additives, components or steps. For experts in the field, other objects, advantages and characteristics of the invention shall be inferred in part from the description and practice of the invention. The following figures and examples are given by way of a non-limiting illustration of the present invention.

The quiescent cardiomyocytes were exposed to VLDL under conditions of normoxia or hypoxia. A) Analysis by real-time PCR of changes in LRP1, VLDLR and LDLR expression induced by increasing doses of VLDL. Data were processed with a software program based on the relative calculation of mRNA concentration according to the Ct (threshold cycle) value. Data were normalized by the endogenous control ARBP. B) A Western blot is displayed representing LRP1, VLDLR and LDLR protein expression levels in HL-1 exposed to VLDL (1.8 mM, 18 hours) in normoxia or hypoxia. β-tubulin levels are displayed as a protein load control. C) Thin layer chromatography showing the bands of cholesteryl ester (CE), triglycerides (TG) and free cholesterol (FC) and a line graph with quantification of these bands in HL-1 cells exposed to normoxia (dotted lines) or hypoxia (continuous lines). Results were shown as micrograms of CE or TG per milligram of cellular protein and were expressed as the mean±SEM of three experiments carried out in duplicate. *P<0.05 vs. cardiomyocytes without VLDL: #P<0.05 vs. cardiomyocytes in normoxia.

Figure 3:
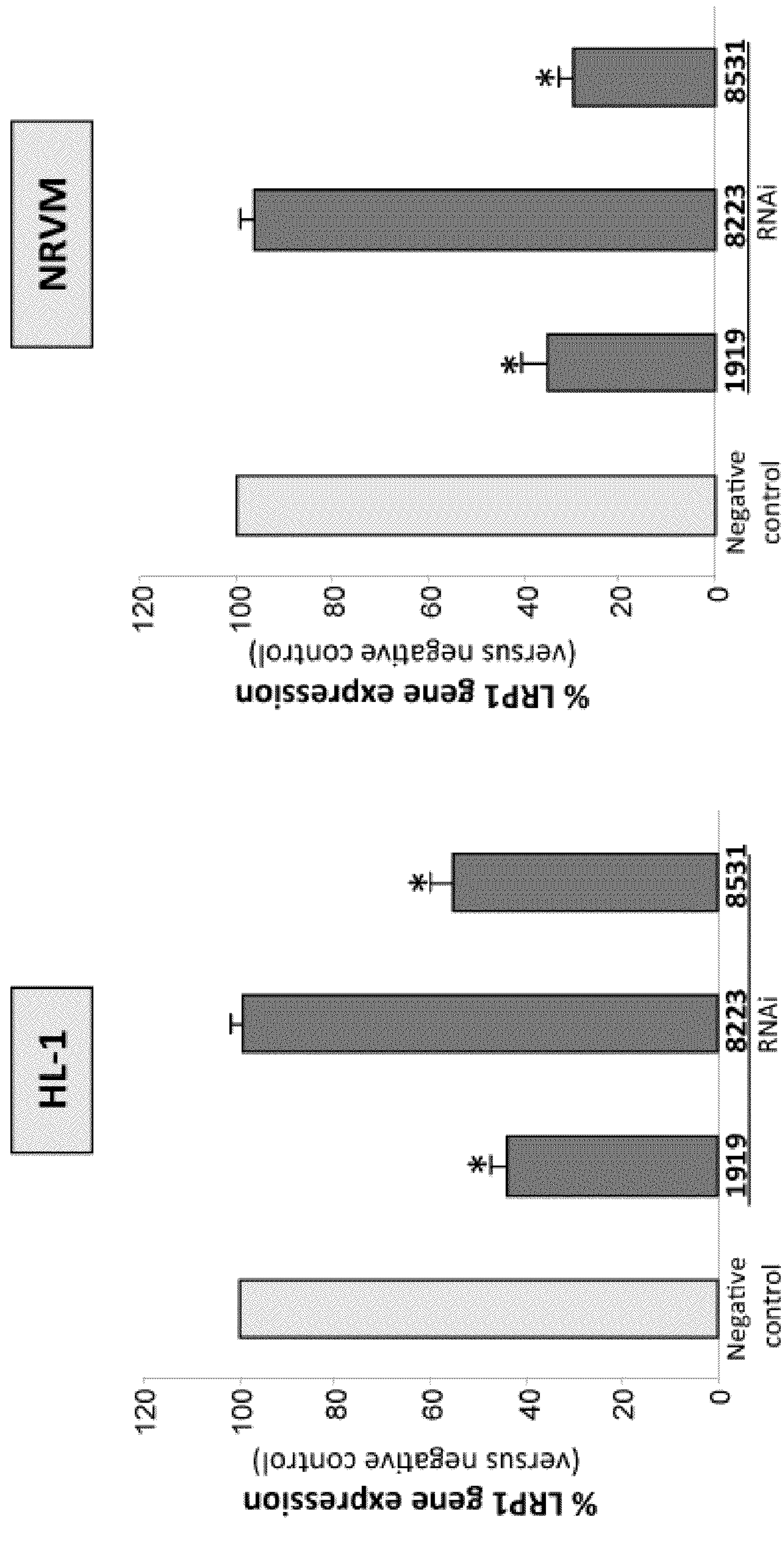

FIG. 3. Design of the miR RNAi sequences and study of their efficiency in blocking LRP1 expression in HL-1 and NRVM. Analysis of LRP1 mRNA expression in HL-1 cells infected with RNAi1919, RNAi8223 or RNAi8531. Data were processed with a software program based on the relative calculation of mRNA concentration according to the Ct (threshold cycle) value. Data were normalized by the endogenous control ARBP. The results were expressed as the percentage of expression with respect to cells infected with the negative control. *P<0.05 vs. cells transfected with the negative control.

Figure 4:
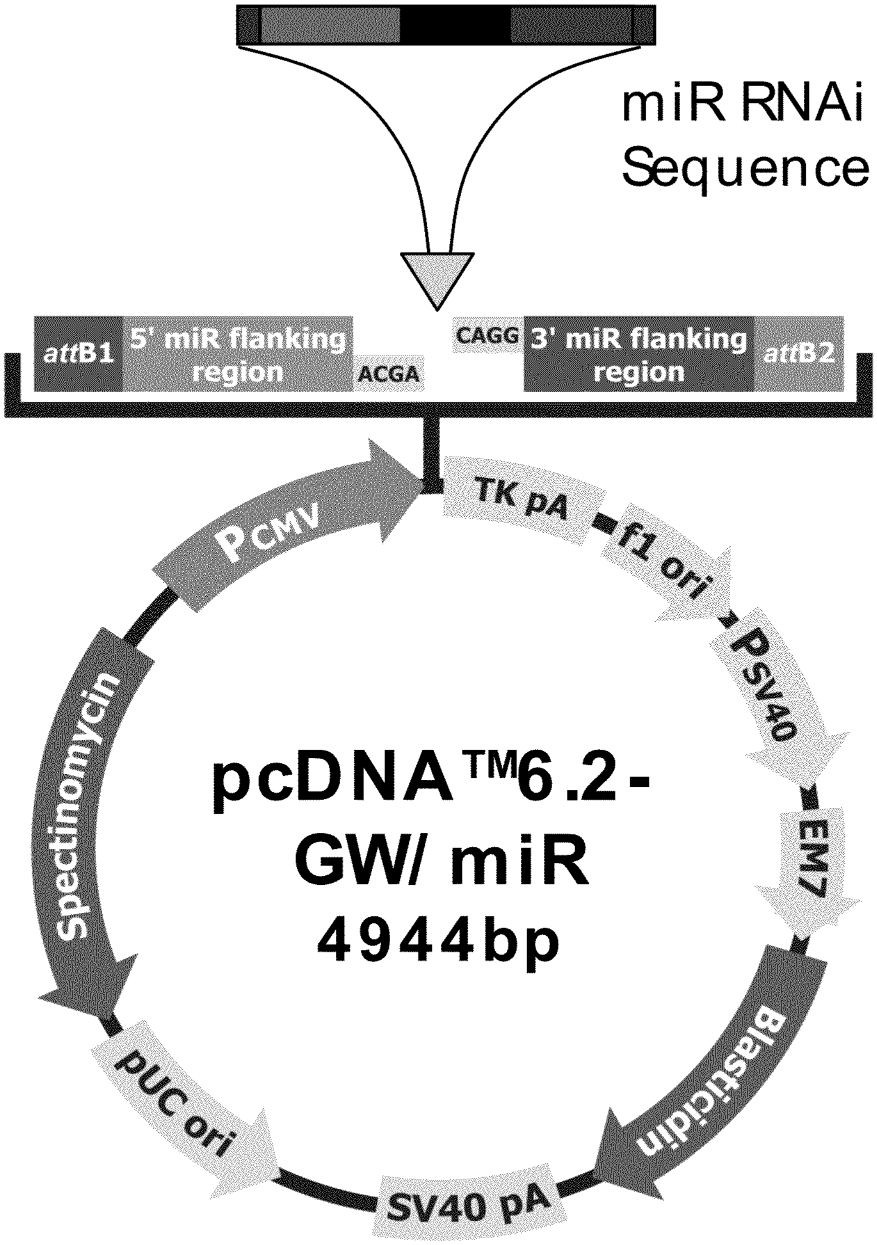
Figure 4:
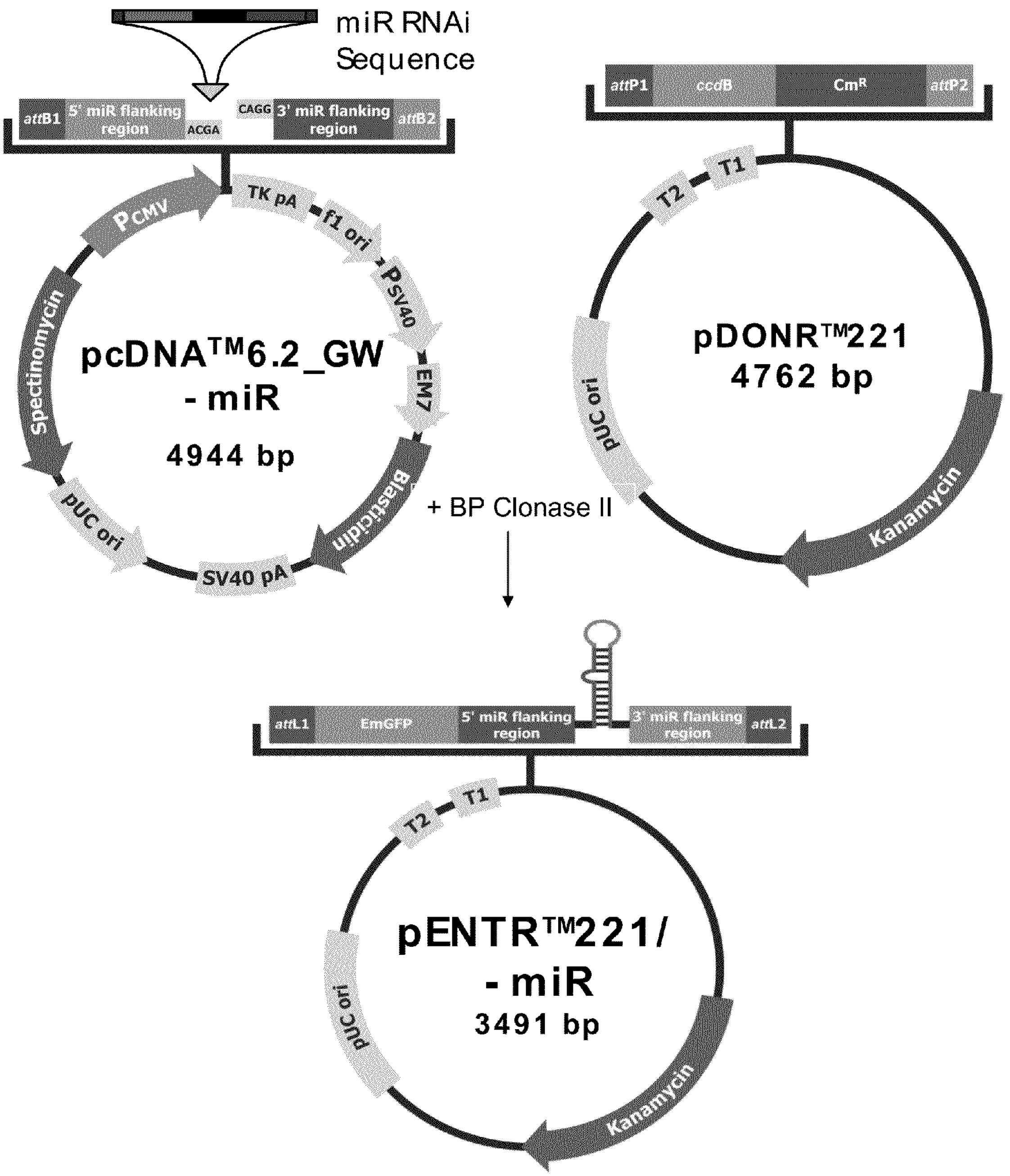

FIG. 4. Use of the BLOCK-IT™ RNAi Designer system to inhibit LRP1 expression (XM_001056970) by means of its incorporation into lentiviruses used to infect HL-1 and NRVM. (A) Generation of the miR RNAi expression vector by annealing the oligos and ligation into the pcDNA™6.2_GW/miR linear vector. (B) Transfer of miR RNAi constructions to pDONR™221 vectors by means of the reaction catalyzed by BP clonase II. (C) Transfer of the miRNA sequence from the clone pENTR™221 along with pENTR5'-CMV plasmid to vector 0.4/R4R2/V5-DEST™ by means of the reaction catalyzed by LR clonase II.

Figure 5A:
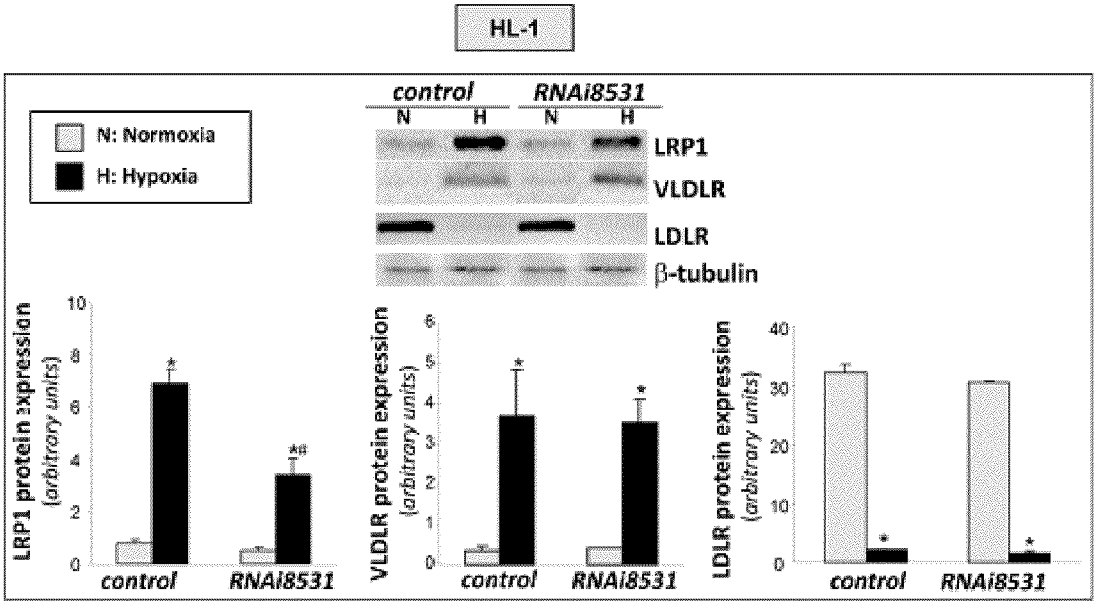
Figure 5B:
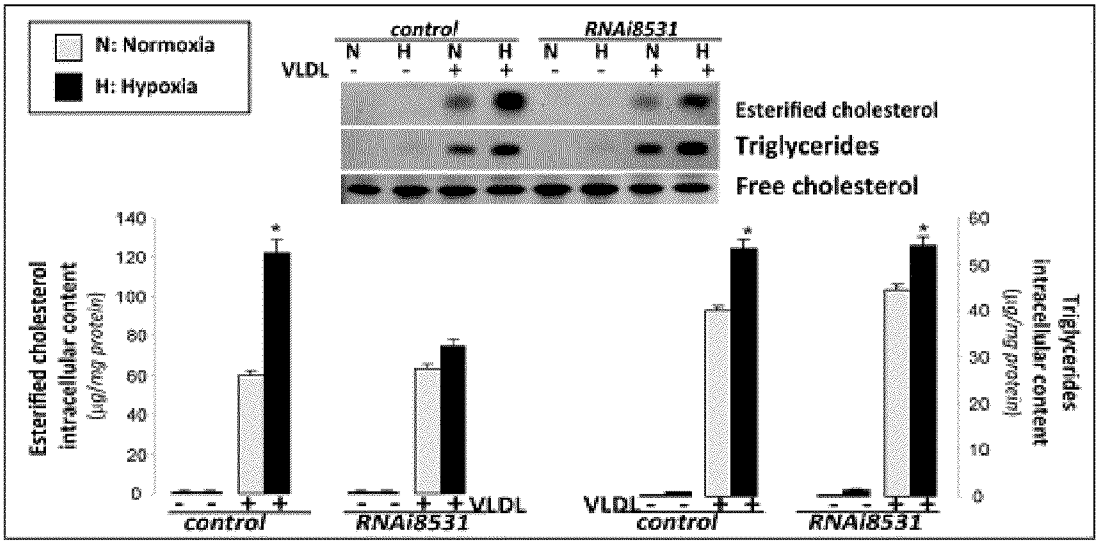

FIG. 5. The effect of RNAi8531 on LRP1 expression and on the accumulation of CE and TG originating from VLDL in HL-1 exposed to normoxia or hypoxia. HL-1 stably transfected with RNAi8531 or with the negative control were cultivated for 48 hours in the presence of blasticidin. The cells were subjected to quiescence for 24 hours and were later exposed to normoxia (N, grey bars) or hypoxia (H, black bars) A) A Western blot representative of LRP1, VLDLR and LDLR expression in HL-1 infected with the negative control or with miR8531 as well as quantification of the corresponding bands is displayed. β-tubulin levels are displayed as a protein load control. B) The quiescent HL-1 cells were exposed to normoxia or hypoxia for 24 hours and during the last 12 hours were incubated with VLDL (1.8 mM). A representative thin layer chromatography is displayed with the cholesteryl ester (CE), triglyceride (TG) and free cholesterol (FC) bands and the histograms with the quantification of the CE and TG bands. The results were expressed as micrograms of lipids per milligram of protein and were displayed as the mean±SEM of three experiments carried out in triplicate. *P<0.05 vs. cells infected with the negative control. C) The quiescent HL-1 cells were exposed to normoxia or hypoxia for 24 hours and during the last 12 hours were incubated with doubly radiolabeled VLDLs (1.8 mM). The cells were collected and cholesterol and triglyceride uptake was evaluated by means of a dpm count of [$^{3}$H] and [$^{14}$C] associated with the cell extracts, respectively. The results were expressed as [$^{3}$H] or [$^{14}$C] dpm per milligram of cellular protein. [$^{3}$H]/[$^{14}$C] cellular ratio was also determined. The results were expressed as the mean±SEM of three experiments carried out in triplicate. *P<0.05 vs. HL-1 in normoxia. #P<0.05 vs. cardiomyocytes infected with the negative control.

Figure 6A:
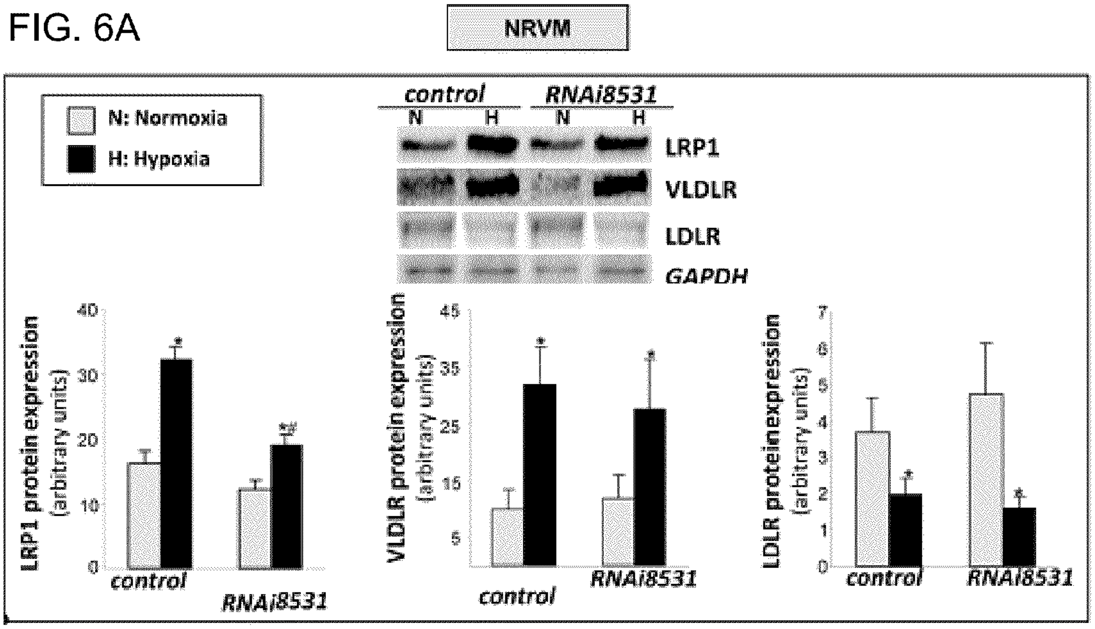
Figure 6B:
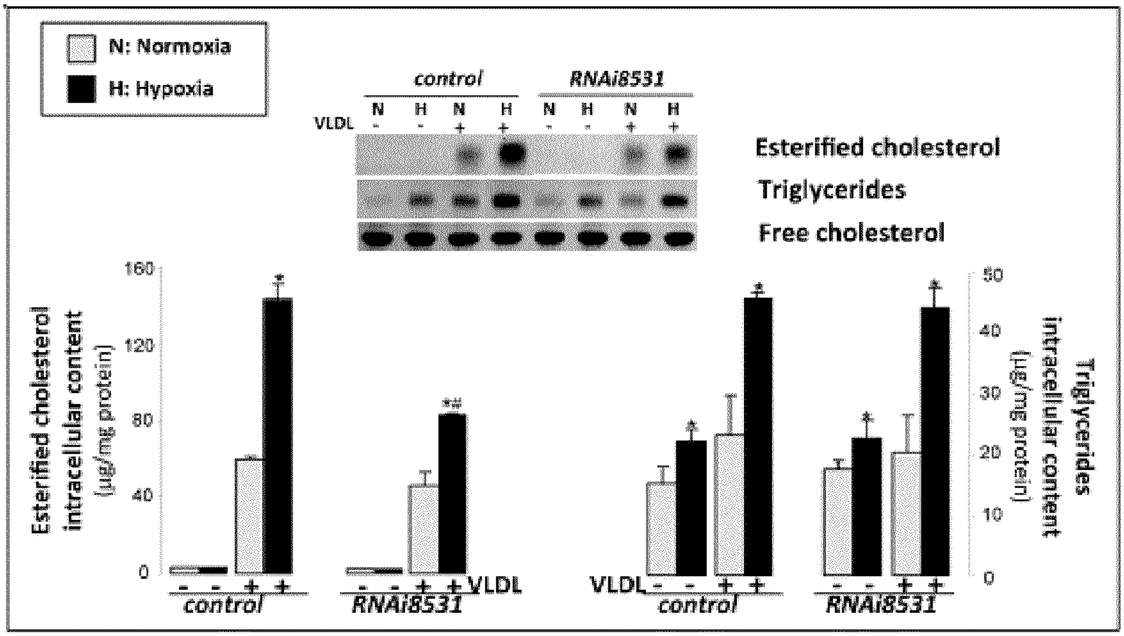

FIG. 6. The effect of RNAi8531 on the expression of LRP1 and on the accumulation of CE and TG originating from VLDL in NRVM exposed to normoxia or hypoxia. NRVM transiently transfected with RNAi8531 or with the negative control were cultivated for 48 hours in the presence of blasticidin. The cells were subjected to quiescence for 24 hours and were later exposed to normoxia (N, grey bars) or hypoxia (H, black bars) A) A Western blot representative of the expression of LRP1, VLDLR and LDLR in NRVM infected with the negative control or with miR8531 as well as the quantification of the corresponding bands. GAPDH levels are displayed as a protein load control. B) The quiescent NRVM cells were exposed to normoxia or hypoxia for 24 hours and during the last 12 hours were incubated with VLDL (1.8 mM). A representative thin-layer chromatography is displayed with the cholesteryl ester (CE), triglyceride (TG) and free cholesterol (FC) bands, and the histograms with the quantification of the CE and TG bands. The results were expressed as micrograms of lipids per milligram of protein and were displayed as the mean±SEM of three experiments carried out in triplicate. *P<0.05 vs. cells infected with the negative control.

FIG. 7. The effect of ischaemia induced by acute infarction on neutral lipid accumulation and lipoprotein receptor expression in the myocardium (porcine model). Samples from a non-ischaemic zone (remote, white bars) and ischaemic (penumbra, black bars) were taken from the hearts of pigs subjected to infarction (n=6) or controls (n=3, sham) and were frozen in liquid nitrogen. One part of each sample was used for lipid extraction and thin layer chromatography, and the other part to obtain protein for the Western blot. A) Western blot analysis displaying the protein expression levels of LRP1 and VLDLR and bar graph showing the quantification of the bands. The levels of protein expression of GAPDH are displayed as a protein load control B) Thin layer chromatography displaying the bands of cholesteryl ester (CE), triglycerides (TG) and free cholesterol (FC), and histograms displaying the quantification of the CE and TG bands. Data were expressed as the mean±SEM. P<0.05 vs. non-ischaemic myocardium or sham animals.

FIG. 8. Analysis of the expression of LRP1 in hearts explanted from patients with idiopathic cardiomyopathy (DCM) or with ischaemic cardiomyopathy (ICM) as compared to control subjects (CNT). A) A Western blot analysis of LRP1 protein expression was performed using the protein obtained from 50 mg of myocardial tissue homogenized in TriPure reagent. GAPH levels were used as a load control. B) Representative image of LRP1 immunohistochemical analysis in myocardial tissue. Magnification×240.

FIG. 9. Analysis of VLDLR expression in hearts explanted from patients with idiopathic cardiomyopathy (DCM) or with ischaemic cardiomyopathy (ICM) as compared to control subjects (CNT). A) A Western blot analysis of VLDLR protein expression was performed using the protein obtained from 50 mg of myocardial tissue homogenized in TriPure reagent. GAPH levels were used as a load control. B) Representative image of VLDLR immunohistochemical analysis in myocardial tissue. Magnification×240.

FIG. 10. Determination of myocardial levels of cholesteryl ester (CE), triglycerides (TG) and free cholesterol (FC) in hearts explanted from patients with idiopathic dilated cardiomyopathy (DCM) or with ischaemic cardiomyopathy (ICM) as compared to control subjects (CNT). Lipid extraction and subsequent thin-layer chromatography were performed using 5 mg of myocardial tissue (A) in order to determine the levels of cholesteryl ester (CE) (B), triglycerides (TG) (C), and free cholesterol (FC) (D) CNT, controls; DCM, idiopathic dilated cardiomyopathy; ICM, ischaemic cardiomyopathy. The results were expressed as micrograms per milligram of tissue and were displayed as mean±SD.

FIG. 11. Correlation between LRP1 expression and cholesteryl ester (CE) content in the myocardium of patients with cardiac insufficiency. Analysis of the correlation between mRNA expression of LRP1 (A) or protein expression of LRP1 (B) and CE content of the myocardium.

FIG. 12. Correlation between VLDLR expression and cholesteryl ester (CE) content in the myocardium of patients with cardiac insufficiency. Analysis of the correlation between the mRNA expression of VLDLR (A) or the protein expression of VLDLR (B) and the CE content of the myocardium.

FIG. 13. Modulation of the expression of the receptor LRP1 by transcription factor HIF-1α in cardiomyocytes. The cardiomyocytes from the line HL-1 were transfected with siRNA-anti-HIF-1α or siRNA-random (0.6 μmol/L) by nucleofection. Control cells were nucleofected in the absence of siRNA. The cells were exposed to normoxia or hypoxia and were collected after 4 hours to analyze the expression of HIF-1α and after 24 hours to analyze the expression of LRP1. A) A representative Western blot image and bar graph displaying HIF-1α and LRP1 quantification. β-tubulin levels are displayed as a load control. The results were expressed as the mean±SEM of two experiments carried out in triplicate. *P<0.05 vs. HL-1 in normoxia. B) Quantification by real-time PCR of LRP1, VLDLR and LDLR gene expression in HL-1 exposed to normoxia and hypoxia for 24 hours. Data were processed with a software program based on the relative calculation of mRNA concentration according to the Ct (threshold cycle) value. Data were normalized by the endogenous control ARBP and were expressed as the mean±SEM of three experiments carried out in duplicate. *P<0.05 vs. HL-1 in normoxia; # vs. control cells.

FIG. 14. The protein E3 ubiquitin ligase CHFR modulates the stability of the protein LRP1 in smooth muscle cells from the human vascular wall (VSMC). The VSMC were transfected with siRNA-random or siRNA-anti-CHFR and were later exposed to low density lipoproteins modified by aggregation (agLDL). A) Bar graphs displaying the quantification by real-time PCR of mRNA expression levels for CHFR. Data were processed with a software program based on the relative calculation of mRNA concentration according to the Ct (Threshold cycle) value. Data were normalized by the endogenous control GAPDH and were expressed as the mean±SEM of three experiments carried out in triplicate. B) A representative Western blot image of the protein expression levels and a bar graph displaying the quantification of LRP1 (C) and CHFR (D) bands normalized by the levels of β-tubulin. *P<0.05 vs. cells not exposed to agLDL. #P<0.05 vs. VSMC treated with siRNA-random.

FIG. 15. Low-density lipoproteins modified by aggregation (agLDL) stabilize the protein LRP1 by means of a decrease in CHFR expression and ubiquitination of the cytoplasmic chain in smooth muscle cells from the human vascular wall (VSMC). A representative Western blot image of the protein expression of CHFR (A) and LRP1 (B) and a bar graph displaying the quantification of the respective bands normalizing the results with β-tubulin. (C) The control VSMC or the VSMC exposed to agLDL (100 μg/mL, 24 hours), were incubated with cycloheximide (100 μM) for the indicated times. β-tubulin levels were displayed as a load control. Line graph showing the percentage of protein expression after adding cycloheximide. The results are displayed as the mean±SEM of two independent experiments carried out in triplicate. (D) The VSMC protein extracts exposed to agLDL were applied over affinity beads with anti-ubiquitin antibodies for the immunoprecipitation of ubiquitinated proteins. A fraction of the cellular extracts was applied over balls bound to unspecific antibodies. Later, the ubiquitinated LRP1 protein was analyzed by Western blot. The "Westerns" were incubated with anti-ubiquitin antibodies demonstrating that ubiquitin expression was not altered by agLDL treatment. *P<0.05 vs. cells not exposed to agLDL.

Figure 16:
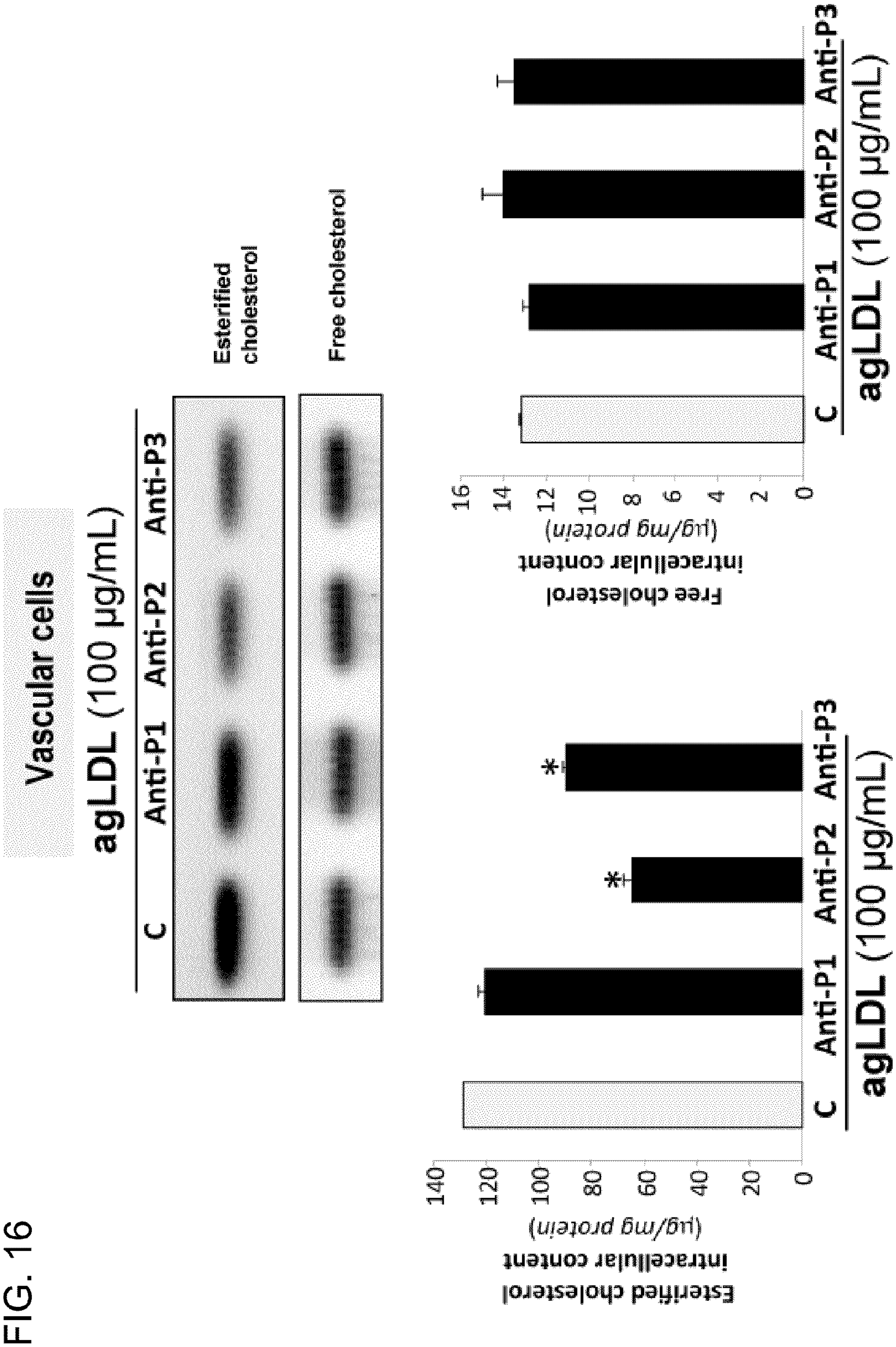

FIG. 16. Effect of the polyclonal antibodies on intracellular accumulation of lipids from LDL modified by aggregation (agLDL) in smooth muscular cells from the human vascular wall (VSMC). The quiescent VSMC cells were exposed to hypoxia for 18 hours. Polyclonal antibodies (anti-P1, anti-P2 and anti-P3) (100 μg/mL) were later added to the culture medium. After 3 hours aggregated LDL (100 μg/mL) were added to the same culture medium and were kept for 4 more hours. The cells were collected in NaOH, and the lipid extraction and thin-layer chromatography were performed. A representative thin-layer chromatography is displayed showing the cholesteryl ester (CE) and free cholesterol (FC) bands and histograms with the quantification of the CE bands. The results were expressed as micrograms of lipid per milligram of protein and were displayed as the mean±SEM of three experiments carried out in triplicate. *P<0.05 vs. control cells.

Figure 17:
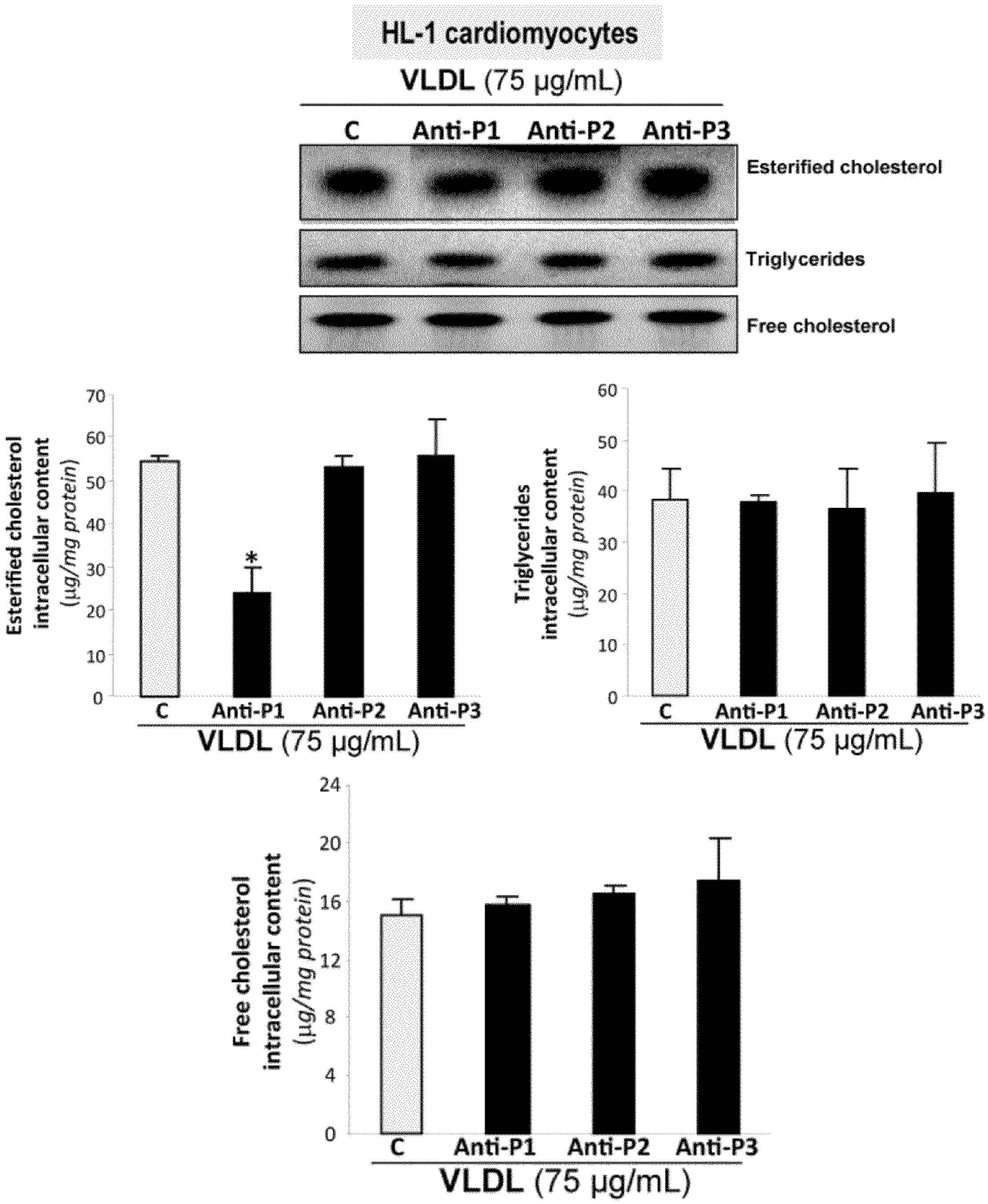

FIG. 17. Effect of the polyclonal antibodies on intracellular accumulation of lipids from VLDL in HL-1 cardiomyocytes exposed to hypoxia. The quiescent HL-1 cells were exposed to hypoxia for 24 hours. Polyclonal antibodies (anti-P1, anti-P2 and anti-P3) (100 μg/mL) were later added to the culture medium, and after 4 hours VLDL (75 μg/mL) were added to the same culture medium and were kept for 4 hours. HL-1 cardiomyocytes were collected in NaOH, after which lipid extraction was performed followed by a thin layer-chromatography. A representative thin layer chromatography with the cholesteryl ester (CE), triglyceride (TG) and free cholesterol (FC) bands and the histograms with the quantification of the CE and TG bands are displayed. The results were expressed as micrograms of lipid per milligram of protein and were displayed as the mean±SEM of three experiments carried out in triplicate. *P<0.05 vs. control cells.

BIBLIOGRAPHY

Bharadwaj K G, Hiyama Y, Hu Y, Huggins L A, Ramakrishnan R, Abumrad N A, Shulman G I, Blaner W S, Goldberg I J. Chylomicron- and VLDL-derived lipids enter the heart through different pathways: in vivo evidence for receptor- and non-receptor-mediated fatty acid uptake. *J Biol Chem* 2010; 285:37976-37986.

Boström P, Magnusson B, Svensson P A, Wiklund O, Borén J, Carlsson L M, Ståhlman M, Olofsson S O, Hultén L M. Hypoxia converts human macrophages into triglyceride-loaded foam cells. *Arterioscler Thromb Vasc Biol* 2006; 26:1871-1876.

Burke A P, Virmani R. Pathophysiology of acute myocardial infarction. *Med Clin North Am* 2007; 91:553-572.

Camino-López S, Llorente-Cortés V, Sendra J, Badimon L. Tissue factor induction by aggregated LDL depends on LDL receptor-related protein expression (LRP1) and Rho A translocation in human vascular smooth muscle cells. *Cardiovasc Res* 2007; 73:208-216.

Camino-López S, Badimon L, González A, Canals D, Pena E, Llorente-Cortés V. Aggregated low density lipoprotein induces tissue factor by inhibiting sphingomyelinase activity in human vascular smooth muscle cells. *J Thromb Haemost* 2009; 7:2137-2146.

Castellano J, Farré J, Fernandes J, Bayes-Genis A, Cinca J, Badimon L, Hove-Madsen L, Llorente-Cortés V. Hypoxia exacerbates Ca2+-handling disturbances induced by very low density lipoproteins (VLDL) in neonatal rat cardiomyocytes. *J Mol Cell Cardiol* 2011; 50:894-902.

Castellano J, Aledo R, Sendra J, Costales P, Juan-Babot O, Badimon L, Llorente-Cortés V. Hypoxia stimulates Low-Density Lipoprotein Receptor-Related Protein-1 Expression Through Hypoxia-Inducible Factor-1α in Human Vascular Smooth Muscle Cells. *Arterioscler Thromb Vasc Biol* 2011; 31:1411-1420.

Chabowski A, Gorski J, Calles-Escandon J, Tandon N N, Bonen A. Hypoxia-induced fatty acid transporter translocation increases fatty acid transport and contributes to lipid accumulation in the heart. *FEBS Letters* 2006; 580:3617-3623.

Fielding C J. Metabolism of cholesterol-rich chylomicroms. Mechanism of binding and uptake of cholesteryl esters by the vascular bed of the perfused rat heart. *J Clin Invest* 1978; 62:141-51.

García-Dorado D, Rodríguez-Sinovas A, Ruiz-Meana M, Inserte J, Agulló L, Cabestrero A. The end-effectors of preconditioning protection against myocardial cell death secondary to ischaemia-reperfusion. *Cardiovasc Res* 2006; 70:274-85.

Goldfarb J W, Roth M, Han J. Myocardial fat deposition after left ventricular myocardial infarction: assessment by using MR water-fat separation imaging. *Radiology* 2009; 253: 65-73.

Hakala J K, Oörni K, Pentikainen M O, Hurt-Camejo E, Kovanen P T. Lipolysis of LDL by human secretory phospholipase A(2) induces particle fusion and enhances the retention of LDL to human aortic proteoglycans. Arterioscler *Thromb Vasc Biol* 2001; 21:1053-1058.

Handschug K, Schulz S, Schnürer C, Köhler S, Wenzel K, Teichmann W, Gläser C. Low-density lipoprotein receptor-related protein in atherosclerosis development: up-regulation of gene expression in patients with coronary obstruction. *J Mol Med* 1998; 76:596-600.

Herz J, Strickland D K. LRP: a multifunctional scavenger and signalling receptor. *J Clin Invest* 2001; 108:779-784.

Kim E, Tolhurst A T, Qin L Y, Chen X Y, Febbraio M, Cho S. CD36/fatty acid translocase, an inflammatory mediator, is involved in hyperlipidemia-induced exacerbation in ischaemic brain injury. *J Neurosci* 2008; 28:4661-4670.

Llorente-Cortés V, Otero-Viñas M, Badimon L. Differential role of heparan sulfate proteoglycans on aggregated LDL uptake in human vascular smooth muscle cells and mouse embryonic fibroblasts. *Arterioscler Thromb Vasc Biol* 2002; 22:1905-1911.

Llorente-Cortés V, Otero-Viñas M, Hurt-Camejo E, Martinez-González J, Badimon L. Human coronary smooth muscle cells internalize versican-modified LDL through LDL receptor-related protein and LDL receptors. *Arterioscler Thromb Vasc Biol* 2002; 22:387-393.

Llorente-Cortés V, Otero-Viñas M, Sanchez S, Rodríguez C, Badimon L. Low-density lipoprotein upregulates low-density lipoprotein receptor-related protein expression in vascular smooth muscle cells: possible involvement of sterol regulatory element binding protein-2-dependent mechanism. *Circulation* 2002; 106:3104-10.

Llorente-Cortés V, Otero-Viñas M, Camino-López S, Llampayas O, Badimon L. Aggregated low-density lipoprotein uptake induces membrane tissue factor procoagulant activity and microparticle release in human vascular smooth muscle cells. *Circulation* 2004; 110:452-459.

Llorente-Cortés V, Otero-Viñas M, Camino-López S, Costales P, Badimon L. Cholesteryl esters of aggregated LDL are internalized by selective uptake in human vascular smooth muscle cells. *Arterioscler Thromb Vasc Biol* 2006; 26:117-123.

Llorente-Cortés V, Royo T, Juan-Babot O, Badimon L. Adipocyte differentiation-related protein is induced by LRP1-mediated aggregated LDL internalization in human vascular smooth muscle cells and macrophages. *J Lipid Res* 2007; 48:2133-2140.

Llorente-Cortés V, Royo T, Otero-Viñas M, Berrozpe M, Badimon L. Sterol regulatory element binding proteins downregulate LDL receptor-related protein (LRP1) expression and LRP1-mediated aggregated LDL uptake by human macrophages. *Cardiovasc Res* 2007; 74:526-536.

Llorente-Cortés V, Otero-Viñas M, Berrozpe M, Badimon L. Intracellular lipid accumulation, low-density lipoprotein receptor-related protein expression, and cell survival in vascular smooth muscle cells derived from normal and atherosclerotic human coronaries. *Eur J Clin Invest* 2004; 34:182-190.

Luoma J, Hiltunen T, Särkioja T, Moestrup S K, Gliemann J, Kodama T, Nikkari T, Ylä-Herttuala S. Expression of alpha 2-macroglobulin receptor/low density lipoprotein receptor-related protein and scavenger receptor in human atherosclerotic lesions. *J Clin Invest* 1994; 93:2014-2021.

Mwaikambo B R, Yang C, Chemtob S, Hardy P. Hypoxia upregulates CD36 expression and function via hypoxia-inducible factor-1- and phosphatidylinositol 3-kinase-dependent mechanisms. *J Biol Chem* 2009; 284:26695-26707.

Osipov R M, Bianchi C, Feng J, Clements R T, Liu Y, Robich M P, Glazer H P, Sodha N R, Sellke F W. Effect of hypercholesterolemia on myocardial necrosis and apoptosis in the setting of ischaemia-reperfusion. *Circulation* 2009; 120(11 Suppl):S22-30.

Reeder G S, Gersh B J. Modern management of acute myocardial infarction. *Curr Probl Cardiol* 1996; 21(9):585-667.

Sartipy P, Johansen B, Gâsvik K, Hurt-Camejo E. Molecular basis for the association of group IIA phospholipase A(2) and decorin in human atherosclerotic lesions. *Circ Res* 2000; 86:707-714.

Schulz S, Birkenmeier G, Schagdarsurengin U, Wenzel K, Müller-Werdan U, Rehfeld D, Süss T, Kabisch A, Werdan K, Gläser C. Role of LDL receptor-related protein (LRP) in coronary atherosclerosis. *Int J Cardiol* 2003; 92:137-144.

Sendra J, Llorente-Cortés V, Costales P, Huesca-Gómez C, Badimon L. Angiotensin II upregulates LDL receptor-related protein (LRP1) expression in the vascular wall: a new pro-atherogenic mechanism of hypertension. *Cardiovasc Res* 2008; 78:581-589.

Straeter-Knowlen I M, Evanochko W T, den Hollander J A, Wolkowicz P E, Balschi J A, Caulfield J B, Ku D D, Pohost G M, Wolkowicz P E, Balschi J A, Caulfield J B, et al. 1H NMR spectroscopic imaging of myocardial triglycerides in excised dog hearts subjected to 24 hours of coronary occlusion. *Circulation* 1996; 93:1464-1470.

Strickland D K, Kounnas M Z. Mechanisms of Cellular Uptake of Thrombin-Antithrombin II Complexes Role of the Low-Density Lipoprotein Receptor-Related Protein as a Serpin-Enzyme Complex Receptor. *Trends Cardiovasc Med* 1997; 7:9-16.

Talukder M A, Zweier J L, Periasamy M. Targeting calcium transport in ischaemic heart disease. *Cardiovasc Res* 2009; 84:345-352.

Yagyu H, Chen G, Yokoyama M, Hirata K, Augustus A, Kako Y, Seo T, Hu Y, Lutz E P, Merkel M, Bensadoun A, Homma S, Goldberg I J. Lipoprotein lipase (LpL) on the surface of cardiomyocytes increases lipid uptake and produces a cardiomyopathy. *J Clin Invest* 2003; 111:419-426.

Yokoyama M, Seo T, Park T, Yagyu H, Hu Y, Son N H, Augustus A S, Vikramadithyan R K, Ramakrishnan R, Pulawa L K, Eckel R H, Goldberg I J. Effects of lipoprotein lipase and statins on cholesterol uptake into heart and skeletal muscle. *J Lipid Res* 2007; 48:646-655.

Wu L, Gonias S L. The low-density lipoprotein receptor-related protein-1 associates transiently with lipid rafts. *J Cell Biochem* 2005; 96:1021-33.

EXAMPLES

The following specific examples provided in this patent are intended to illustrate the nature of the present invention. These examples are included for illustrative purposes only and are not to be interpreted as limitations to the invention claimed herein. Therefore, the examples described below illustrate the invention without limiting the field of application thereof.

Example 1

Figure 1A:
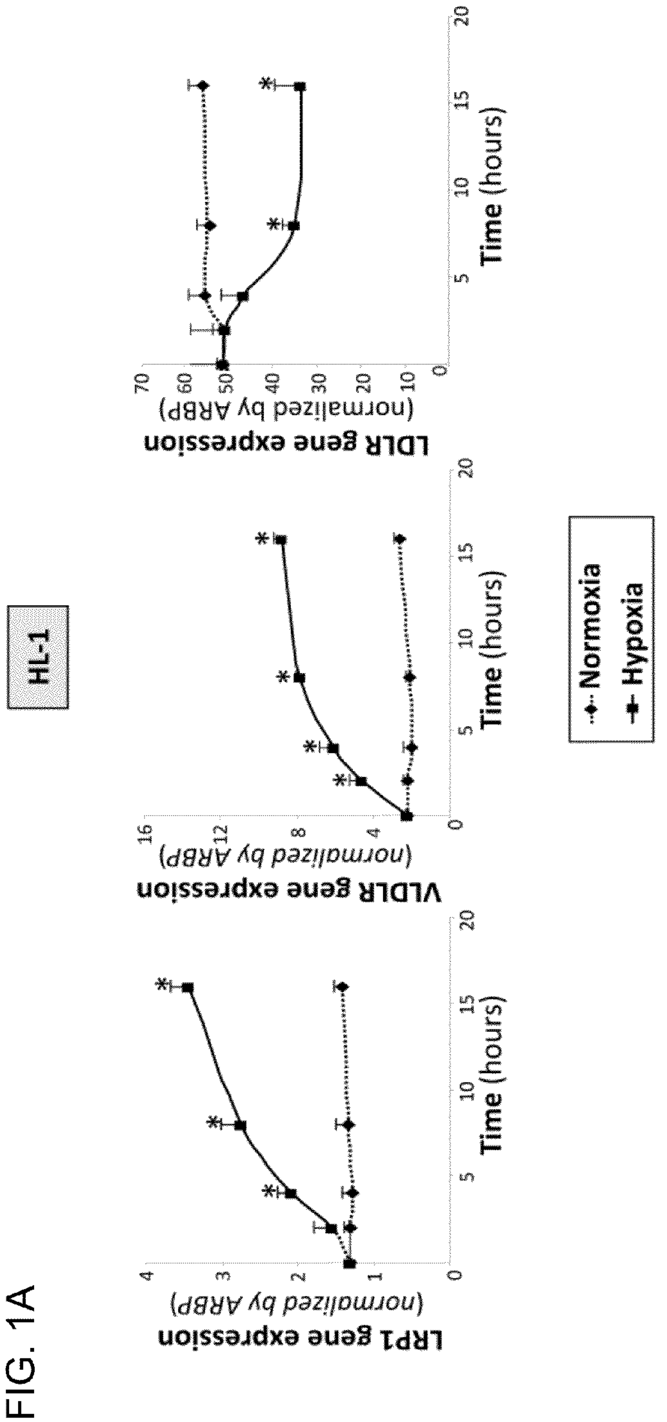
FIG. 1. The effect of hypoxia on LRP1, VLDLR and LDLR expression in cardiomyocytes. A) The quiescent HL-1 cardiomyocytes were exposed to normoxia or hypoxia during increasing times and gene expression of LRP1, VLDLR and LDLR was analyzed by means of real-time PCR. Data were processed with a software program based on the relative calculation of mRNA concentration according to the Ct (threshold cycle) value. Data were normalized by the endogenous control ARBP and were expressed as the mean±SEM of three experiments carried out in duplicate. *$P<0.05$ vs. cardiomyocytes in normoxia. B) Western blot analysis showing LRP1, VLDLR and LDLR bands in both HL-1 and NRVM exposed to normoxia or hypoxia for 18-24 hours. β-tubulin and GAPDH levels were displayed as a protein load control for HL-1 and NRVM cells, respectively.

Effect of Hypoxia on the Expression of Lipoprotein Receptors by the Cardiomyocyte Adult HI-1 cardiomyocytes or neonatal rat cardiomyocytes (NRVM) were exposed to normoxia or hypoxia conditions. The expression of LRP1, VLDL receptor (VLDLR) and classic LDL receptor (LDLR) was analyzed at mRNA level by means of real-time PCR and at protein level by means of a Western blot analysis. (FIG. 1)

Figure 1B:
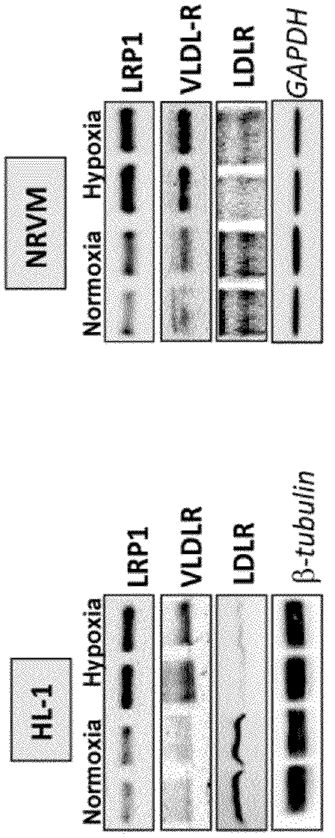

It was observed that in cardiomyocytes subjected to normoxia, the expression levels of LRP1 and VLDLR were very low, whereas levels of LDLR were very high, especially in adult HL-1 cardiomyocytes. This expression pattern was completely altered by exposing the cardiomyocytes to hypoxia. As observed in FIG. 1A, hypoxia induced in a time-dependant way the expression of LRP1 (from 1.6-fold after 4 hours to 2.7-fold after 16 hours) and also the expression of VLDLR (from 2.8-fold after 4 hours to 4-fold after 16 hours), while classic LDL receptor expression decreased (from 10% after 4 hours to 34% after 16 hours). After 24 hours the expression of receptors LRP1 and VLDLR was significantly increased, while the expression of LDLR was decreased by hypoxia both in HL-1 and NRVM (Table 1). As was also observed through PCR, the result of the Western blot demonstrated that hypoxia increased LRP1 and VLDLR expression while decreasing the expression of the classic LDL receptor in both types of cells studied (FIG. 1B).

TABLE 1

Effect of hypoxia on the gene expression of lipoprotein receptors in cardiomyocytes

| | HL-1 | | NRVM | |
|---|---|---|---|---|
| | Normoxia | Hypoxia | Normoxia | Hypoxia |
| LRP1 | 0.8 ± 0.2 | 3.5 ± 0.2* | 1.2 ± 0.2 | 3.1 ± 0.9* |
| VLDLR | 3.2 ± 0.5 | 15 ± 2* | 0.6 ± 0.07 | 1.8 ± 0.34* |
| LDLR | 225 ± 31 | 91 ± 4* | 0.8 ± 0.2 | 0.4 ± 0.1* |

HL-1 and NRVM cardiomyocytes were exposed to normoxia or hypoxia for 24 hours. LRP1, mRNA expression of VLDLR and LDLR was determined by real-time PCR. Data were processed by means of a program based on the Ct value and were normalized by the expression of the endogenous ARBP control. Data were expressed as the mean ± SEM of three experiments carried out in duplicate.
*P < 0.05 vs. cells exposed to conditions of normoxia.

Example 2

Figure 2A:
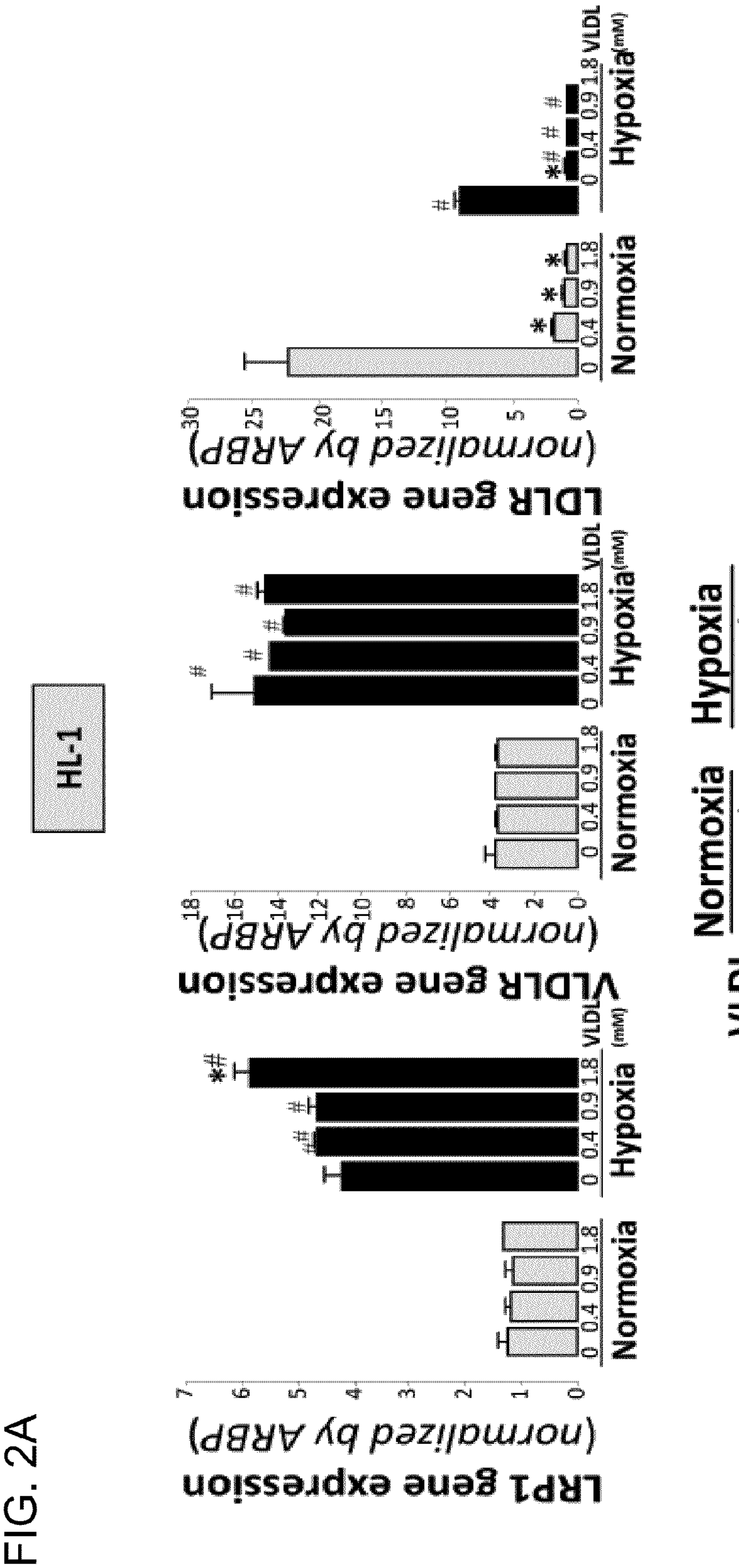
FIG. 2. The effect of VLDL on LRP1, VLDLR and LDLR expression and on neutral lipid (free cholesterol, cholesteryl ester and triglycerides) accumulation in HL-1 exposed to normoxia or hypoxia.
Figure 2B:
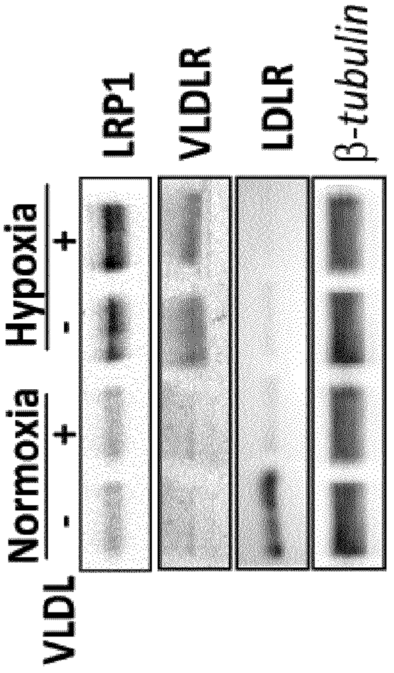
Figure 2C:
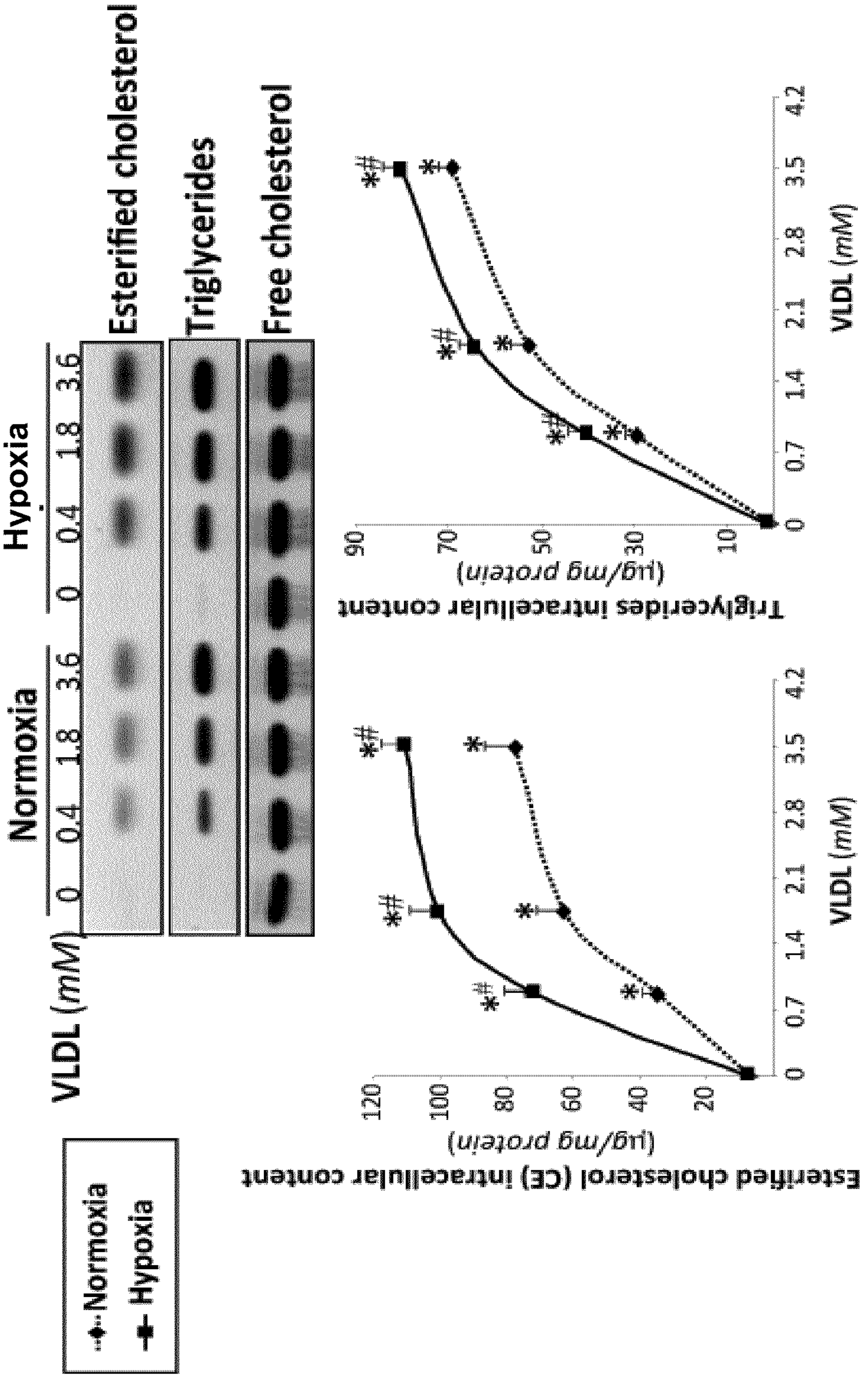

Effect of VLDL on the Expression of Lipoprotein Receptors (LRP1, VLDLR and LDLR) and on the Accumulation of Neutral Lipids (CE, TG and FC) 1N HL-1 Exposed to Normoxia or Hypoxia Cells exposed to VLDL in normoxia or hypoxia were collected and the study of the expression of lipoprotein receptors and the determination of intracellular lipids was performed. The results in FIG. 2A demonstrated that VLDL in every dose tested inhibited the expression or mRNA of LDLR in normoxic or hypoxic cells, and that the highest dose of VLDL increased the expression of LRP1 in hypoxic HL-1. Expression of VLDLR was not significantly altered by the presence of VLDL. The Western blot analysis (FIG. 2B) confirmed at protein level the results obtained at mRNA level. The thin-layer chromatography assays (FIG. 2C) demonstrated that VLDL induced intracellular lipid accumulation in a VLDL-dose dependant way from 6.7±2.2 to 77.6±8.8 μg CE/mg of cellular protein and from 2.5±0.2 to 69.17±3.0 μg TG/mg of cellular protein. Hypoxia also significantly increased said accumulation at every VLDL dose tested (i.e. at 3.6 mM up to 110.52±1.6 μg CE/mg of cellular protein or up to 80.54±3.85 μg TG/mg of cellular protein)

In order to analyze the viability of the cultures, we analyzed the cellular levels of a survival marker (Bcl2) and an apoptosis marker (BAX). Neither VLDL nor hypoxia altered BAX levels. Nonetheless, there was a reduction of Bcl2 levels from 5.39±0.35 to 4.48±0.18 by VLDL (1.8 mM, 18 hours) up to 3.32±0.13 by hypoxia (18 hours) and up to 2.85±0.01 by VLDL (1.8 mM) and hypoxia (18 hours) together. These results demonstrate that our experimental conditions do not induce apoptosis but reduce the survival capacity of the HL-1 cells in culture.

TABLE 2

Effect of VLDL and hypoxia on HL-1 apoptosis

| VLDL | Bcl2 | | BAX | | Bcl2/BAX | |
|---|---|---|---|---|---|---|
| (mM) | Normoxia | Hypoxia | Normoxia | Hypoxia | Normoxia | Hypoxia |
| 0 | 5.4 ± 0.4 | 3.3 ± 0.1# | 10.4 ± 0.1 | 11.3 ± 0.6# | 0.5 | 0.3 |
| 1.8 | 5.0 ± 0.20 | 3.3 ± 0.2# | 9.4 ± 0.5 | 10.9 ± 0.4# | 0.5 | 0.3 |
| 3.6 | 4.5 ± 0.2* | 2.9 ± 0.1*# | 11.1 ± 0.6 | 12.2 ± 0.4*# | 0.4 | 0.2 |

HL-1 cardiomyocytes were exposed to increasing doses of VLDL under conditions of normoxia or hypoxia for 16 hours. The gene expression of Bcl2, BAx and CPP32 was determined by means of real-time PCR. Data were processed by a program based on Ct value and were normalized by the endogenous control ARBP. Data were displayed as the mean ± SEM of four experiments carried out in duplicate.
*P < 0.05 vs. cells incubated in the absence of VLDL;
#P < 0.05 vs. cells exposed to conditions of normoxia.

Example 3

Design of a Lentivirus to Inhibit Expression of the Receptor LRP1

A) Different miR RNAi sequences were designed using the Invitrogen BLOCK-IT™ RNAi Designer to inhibit expression of LRP1 (XM_001056970) by incorporating it into lentiviruses used to infect HL-1 and NRVM: the sequences SEQ ID No: 1, and SEQ ID No: 2 were designed to inhibit the expression of LRP1 (miR RNAi-XM_001056970_1919 or RNAi1919 (SEQ ID No: 16)); the sequences SEQ ID No 3: and SEQ ID No: 4 were designed to inhibit the expression of LRP1 (miR RNAi-XM_001056970_8223 or RNAi8223 (SEQ ID No: 17)); and the sequences SEQ ID No: 5 and SEQ ID No: 6 were designed to inhibit the expression of LRP1 (miR RNAi-XM_001056970_8531 or RNAi8531 (SEQ ID No: 18)).

The plasmid pcDNA™ 6.2-GW/miR was used as a negative control in all the transfection experiments: SEQ ID No: 7 and SEQ ID No: 8 sequences were designed for universal negative control (pcDNA™ 6.2-GW/miR-neg).

B) Analysis of expression of mRNA of LRP1 in HL-1 cells infected with RNAi1919 (SEQ ID No: 16), RNAi8223 (SEQ ID No: 17) or RNAi8531 (SEQ ID No: 18) (FIG. 3) Data were processed by a software program based on the calculation of relative mRNA according to the Ct (threshold cycle) value. Data were normalized by the endogenous control ARBP. Data were expressed as the percentage of expression with respect to the cells infected with the negative control. *$P<0.05$ vs. transfected cells with negative control. Artificially synthesized SEQ ID No: 9 was also used as vector pLenti6.4™-CMV-MSGW.

Figure 4C:
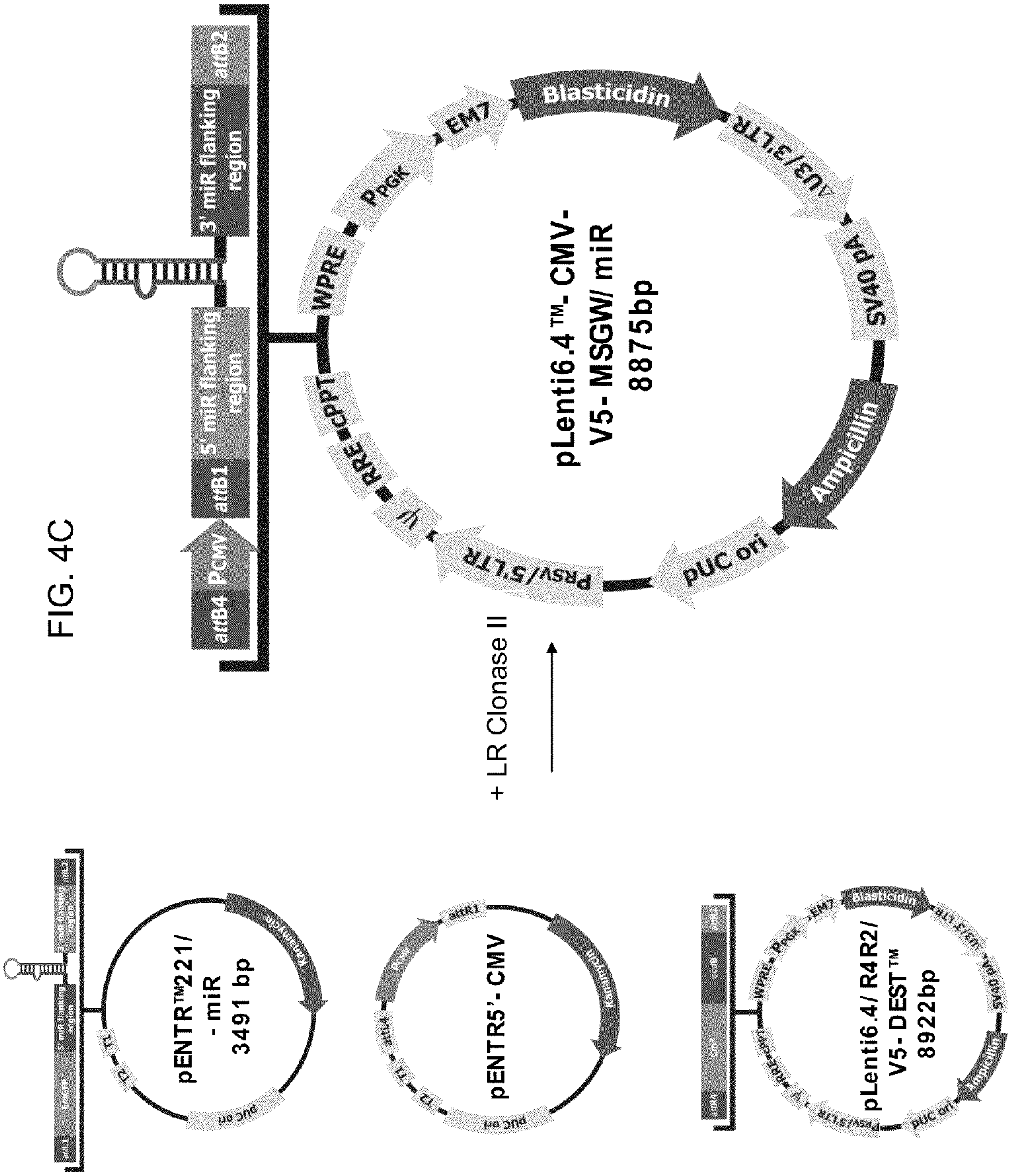

BLOCK-IT™ RNAi Designer is a web tool which makes it possible to design and order specific siRNA or miRNA oligonucleotides against concrete target sequences. After entering the target sequence into the program and setting a series of restrictive parameters, the program generates several RNAi designs which are ordered according to their probable efficiency in inhibiting the expression of the target gene. In this case, the program has generated three sequences capable of inhibiting the LRP1 gene [RNAi1919 (SEQ ID No: 16), RNAi8223 (SEQ ID No: 17) or RNAi8531 (SEQ ID No:18)] as well as the negative control (pcDNA™GW/miR_neg). The pcDNA™-GW/miR_neg plasmid contains an insert forming a "hairpin" structure which is processed in the form of a mature miRNA unable to bond to any known gene in vertebrates. Therefore, this plasmid may be used as a negative control for the knockdown experiments performed with the expression vectors pcDNA™6.2-GW/miR. In order to generate the expression vector miR RNAi the oligos were annealed and ligated to the linear vector pcDNA™6.2-GW/miR (SEQ ID No 10) (FIG. 4A). Next, competent *E. Coli* cells were transformed with the ligated DNA and the cells were selected in LB medium supplemented with 50 μg/mL of spectinomycin. The miR RNAi constructions were later transferred to the pDONR™221 (SEQ ID No: 11) by means of a reaction catalyzed by BP clonase II (FIG. 4B). The miRNA sequence was then transferred from the pENTR™221 (SEQ ID No: 12) clone along with the pENTR5'-CMV (Invitrogen) plasmid to the vector pLenti6.4/R4R2/V5-DEST™ (SEQ ID No: 23) by means of a reaction catalyzed by LR clonase II (FIG. 4C). Competent *E. Coli* cells were transformed with the recombinant expression vector and the cells were selected in LB supplemented with ampicillin.

In the present invention, the term "recombinant expression vector" refers to a small plasmid containing a multiple cloning site flanked by one or two promoter sequences, such as pLenti6.4™-CMV-V5-MSGW/miR (Life Technologies (Invitrogen)). These promoters are required in order to transcribe the DNA fragments inserted in the multiple cloning site. In this case, the inserted DNA sequence refers to the RNAi sequences previously described.

The colonies were picked and cultured overnight in LB medium with ampicillin. Digestion with Hind was performed to verify that recombination had taken place correctly. The lentivirus (pLenti6.4™-CMV-MSGW/miR-XM-001056970-1919 (SEQ ID No: 21); pLenti6.4™-CMV-MSGW/miR-XM-001056970-8223 (SEQ ID No: 24); pLenti6.4™-CMV-MSGW/miR-XM-001056970-8531 (SEQ ID No: 20); pLenti6.4™-CMV-MSGW/miR-neg (Life Technologies (Invitrogen)) were used to transfect the cardiomyocytes. The ability of these sequences to inhibit the mRNA expression of LRP1 was determined by real-time PCR. It was observed that pLenti6.4™-CMV-MSGW/miR-XM-001056970-1919 (SEQ ID No: 21) and pLenti6.4™-CMV-MSGW/miR-XM-001056970-8531 (SEQ ID No: 20) were able to inhibit the mRNA expression of LRP1 in hypoxic cardiomyocytes in about 50% (FIG. 3). pLenti6.4™-CMV-MSGW/miR-XM-001056970-8531 (SEQ ID No: 20) was chosen to stably transfect HL-1 and transiently infect NRVM. Another example of how to inhibit LRP1 expression in the cardiomyocyte could be the use of floxed recombinant alleles and recombination by Cre-resulting in the deletion of a part of the LRP1 promoter including the transcription starting site.

Other examples of how to inhibit the expression of LRP1 could be by modulating the nuclear levels of transcription factors with the ability to modulate the expression of LRP1. Specifically, our group has published that the transcription activity LRP1 is negatively modulated by SREBP transcription factors (Llorente-Cortés V et al, *Circulation* 2002; Llorente-Cortés V et al, *J Mol Biol* 2006; Costales P et al, *Atherosclerosis* 2010), and positively by HIF-1α (Castellano J et al, *Arterioscler Thromb Vasc Biol* 2011) in smooth muscle cells from the vascular wall. Therefore, it is highly probable that SREBP overexpression and HIF-1α inhibition may be strategies worth taking into account in order to inhibit the upwards regulation of LRP1 by hypoxia in cardiomyocytes. Apart from these strategies focused on preventing the upwards regulation of LRP1 induced by hypoxia, it might be more appealing, from a pharmacological point of view, to inhibit the ability of LRP1 to transfer cholesterol from atherogenic lipoproteins to cardiomyocytes in dyslipidemic situations, as this has a lower degree of impact on the physiological functioning of LRP1. To do this, it is certainly essential to develop molecules capable of impeding or hindering the ability of LRP1 to transfer cholesterol to the cardiomyocyte when an ischemic situation occurs, moreover if the patient is dyslipidemic. To this end, we have stably transfected COS cells capable of secreting mini receptors of LRP1, molecules that could be effective in competing with cellular LRP1 competing for the binding of lipoproteins.

Example 4

Figure 5C:
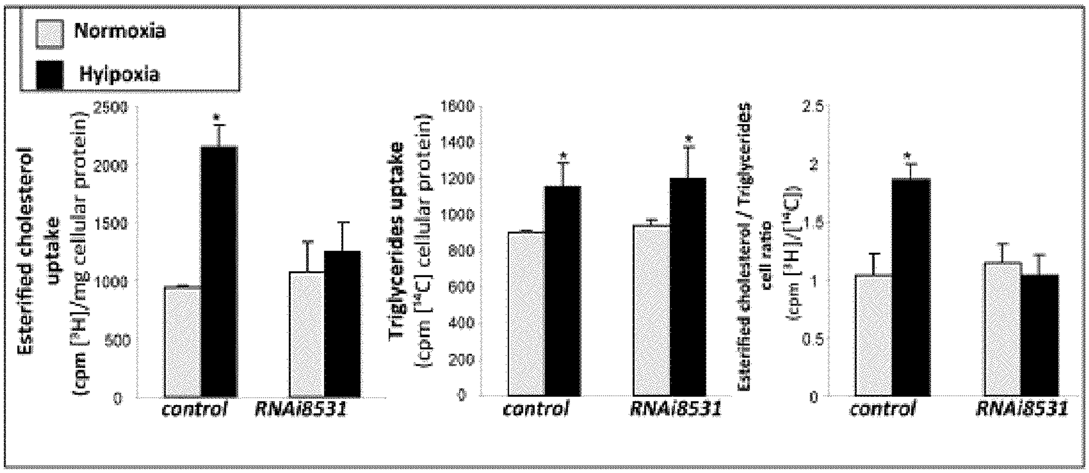

Effect of LRP1 Cellular Deficiency on the Transference of Cholesteryl Ester and Triglycerides from VLDL to Cardiomyocytes Exposed to Normoxia or Hypoxia RNAi8531 (SEQ ID No: 18) reduced the protein expression of LRP1 by 50.7±1.14% in HL-1 (FIG. 5A) and by 40.6±1.8% (FIG. 6A) in NRVM with respect to the same cells transfected with the negative control. Nonetheless, RNAi8531 (SEQ ID No: 18) had no effect over the low protein expression of LRP1 in normoxia. No differences were found in the protein expression of VLDLR or LDLR among the cells transfected with negative control or RNAi8531 (SEQ ID No: 18) independently of whether they were exposed to normoxia or hypoxia. Therefore, with this method, we obtained cardiomyocytes specifically deficient in LRP1 receptor expression. We then studied the effect of VLDL on the intracellular accumulation of CE and TG in LRP1-deficient cardiomyocytes exposed to normoxia and hypoxia with respect to the control variety. Our results demonstrated that overaccumulation of CE induced by hypoxia in HL-1 (FIG. 5B) and NRVM (FIG. 6B) was completely prevented in LRP1-deficient cells. Nonetheless, intracellular overaccumulation of TG induced by hypoxia was similar in LRP1-deficient cells and control cells. These results suggest that the LRP1 deficiency specifically affected CE uptake from VLDL, and that therefore the cholesterol and triglyceride uptake pathways may be independent. In order to study CE and TG uptake specifically, the cardiomyocytes were exposed to VLDL in which the cholesterol and triglyceride components were marked with two different radioisotopes. CE from VLDL was marked with [$^{3}$H] and TG with [$^{14}$C]. The specific activity of [$^{3}$H] was of 439±54 dpm/mg of protein and that of [$^{14}$C] was of 87±15 dpm/mg of protein. Our results demonstrated that LRP1 deficiency completely prevented the increase in the uptake of CE (2.3-fold) induced by hypoxia (FIG. 5C). Nonetheless, the increase in TG uptake inducted by hypoxia (1.3-fold) was similar in both control and LRP1-deficient cells (FIG. 5C). The ratio [$^{3}$H]/[$^{14}$C] was 5±0.8 in the double-marked VLDL, whereas in the HL-1 cells this ratio was 1.04±0.19, indicating that [$^{3}$H] uptake by HL-1 cells in normoxia is very low. Hypoxia increased two-fold the uptake of [$^{3}$H] in control cells, but not in LRP1-deficient cells. Therefore, these results demonstrate that LRP1 exerts a crucial role in selective cholesteryl ester uptake by cardiomyocytes exposed to hypoxia, and that blocking this receptor has a clear impact on cholesteryl ester accumulation in cardiomyocytes. Given that VLDL is one of the heart's main sources of cholesterol, LRP1 blockage may be a key to reducing the supply of cholesterol supply to the ischaemic heart without altering the supply of triglycerides.

Example 5

Figure 7A:
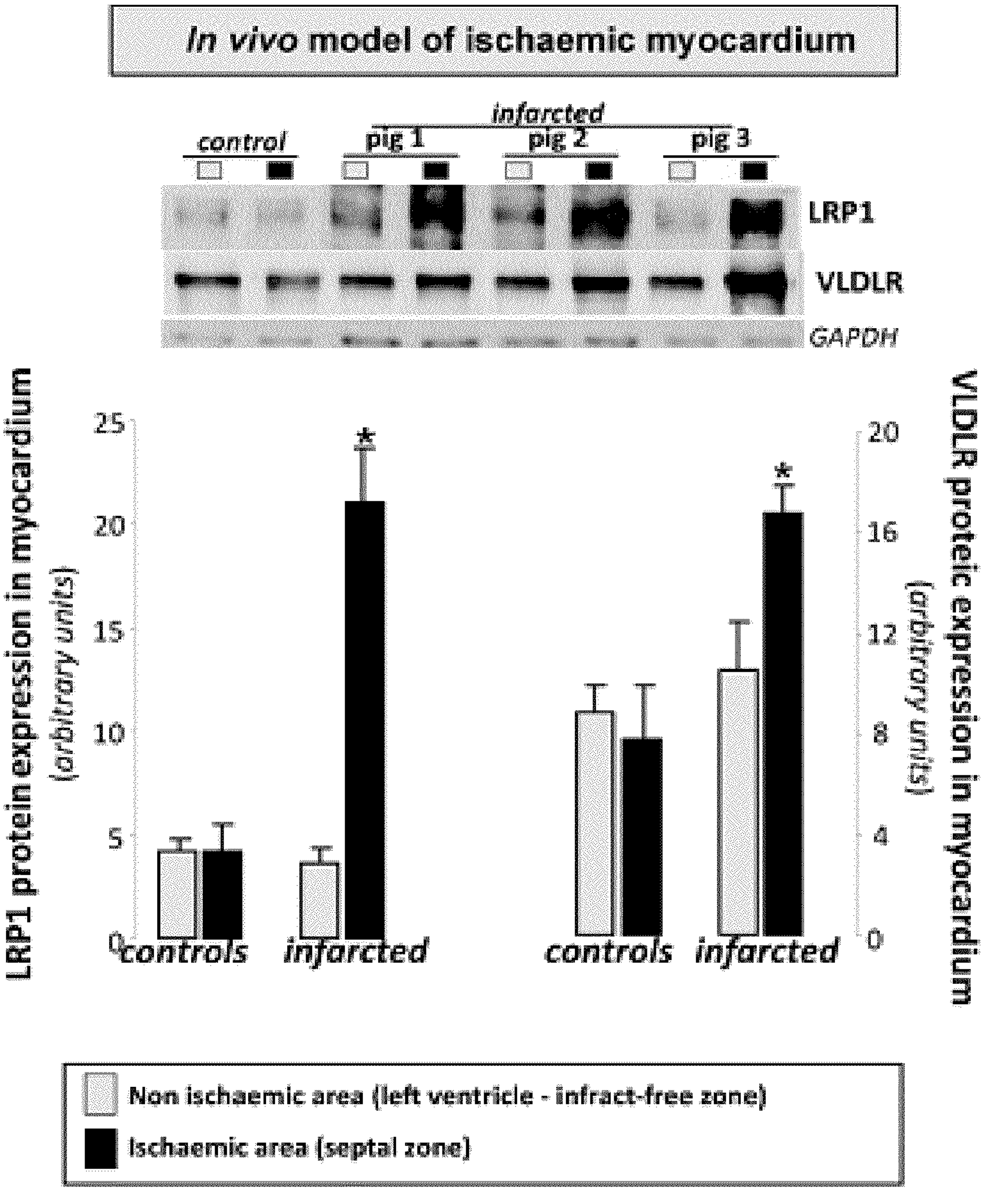

Effect of Ischaemia Inducted by Acute Infarction on Lipid Accumulation in the Heart An experimental model of acute myocardial infarction was used in the previously described porcine model (Vilahur G et al, *J Moll Cell Cardiol* 2011; Vilahur G et al, *J Thromb Haemost* 2009). We evaluated the effect of hypoxia on the accumulation of neutral lipids (CE, TG and FC), and on the expression of lipoprotein receptors (LRP1 and VLDLR) in the non-ischaemic zone (remote myocardium zone) and in the ishacemic zone (penumbra or perinecrotic zone). The lipid pattern was determined by the lipid extraction from the samples and the subsequent thin-layer chromatography. It was demonstrated that cholesteryl ester levels and triglyceride levels increased 2- and 3-fold, respectively, in the ischaemic myocardium vs. the non-ischaemic or control myocardium (FIG. 7A). There was no change in the free cholesterol level between the ischaemic myocardium and the non-ischaemic or control myocardium.

Figure 7B:
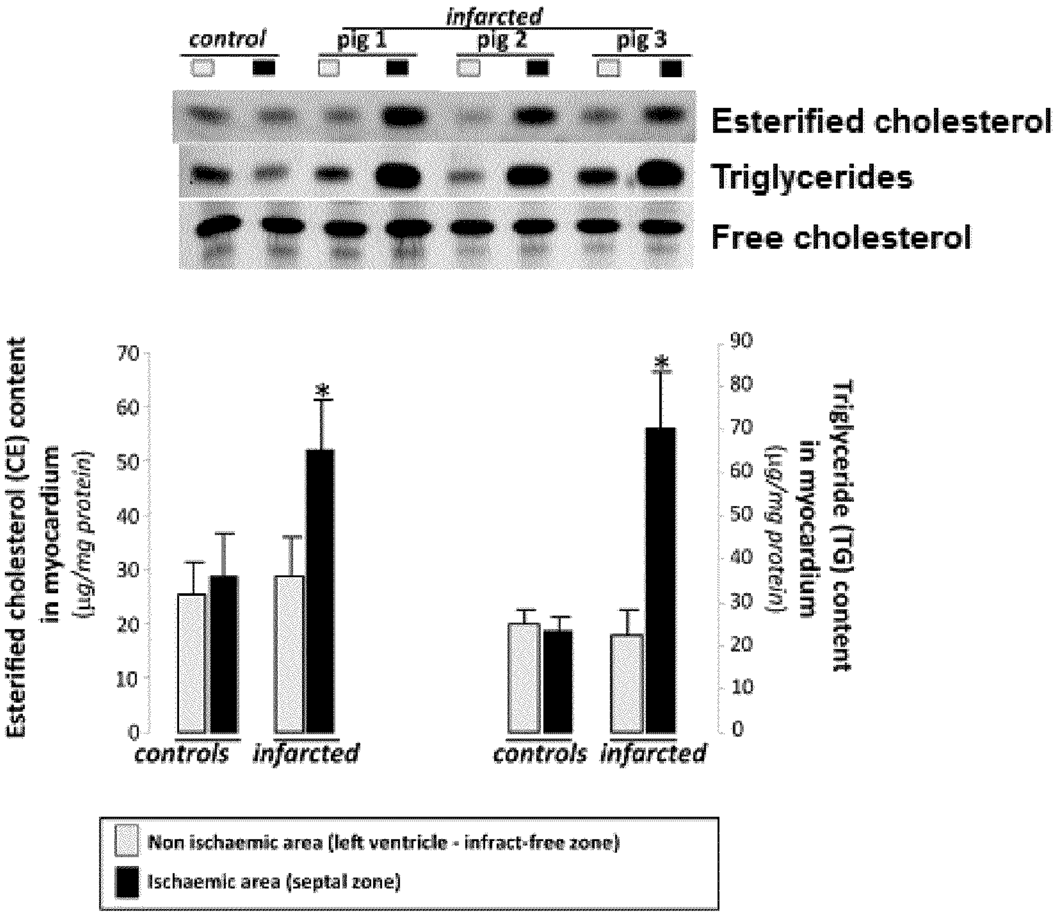

Expression levels of the different lipoprotein receptors were also determined by a Western blot analysis. It was observed that LRP1 protein expression increased 5.7-fold in the ischaemic myocardium vs. the non-ischaemic or control myocardium, P<0.05. An increase in VLDLR protein expression was also observed in the ischaemic zone, although a much more moderate one (2-fold) (FIG. 7B). These results demonstrate that in an acute ischaemic process such as the one induced by acute myocardial infarction, there is a significant increase in LRP1 expression in the penumbra zone of the myocardium, concomitantly with an increase of neutral lipids content.

Example 6

Analysis of Lipoproteic Receptor Expression in Myocardium Samples from Control Subjects, Patients with Idiopathic Dilated Cardiomyopathy or with Ischaemic Cardiomyopathy A total of 55 explanted human hearts were chosen from 26 patients with dilated idiopathic cardiomyopathy (DCM) and from 29 patients with ischaemic cardiomyopathy (ICM) (Table 3). Hearts from 4 healthy people who had died in traffic accidents, and whose hearts could not be used for transplant were used as controls.

TABLE 3

Characteristics of the patients according to the etiology of the cardiac insufficiency

| | dilated (DCM) (n = 26) | ischaemic (ICM) (n = 29) | P |
|---|---|---|---|
| Cardiomyopathy | | | |
| Age (years) | 56 ± 3 | 54 ± 3 | 0.566 |
| Gender (men/women) (%) | 86/14 | 93/1 | |
| NYHA (%) | Class III = 79<br>Class IV = 21 | Class III = 47<br>Class IV = 53 | |
| Cholesterol plasma (mmol/L) | 4.49 ± 0.29 | 3.89 ± 0.28 | 0.833 |
| PWTd (mm) | 73.60 ± 5.43 | 67.60 ± 2.84 | 0.043 |
| EF (%) | 20.20 ± 2.66 | 25.00 ± 2.48 | 0.779 |
| Coronariography | | | |
| 1 vessel (%) | 7 | 27 | |
| 2 vessels (%) | 0 | 7 | |
| 3 vessels (%) | 0 | 53 | |

The results were expressed as the mean±SD for continuous variables and as a percentage of patients in the categorical variables. PWTd: posterior wall thickness of the left ventricle in diastole. EF: ejection fraction. DCM: dilated cardiomyopathy; ICM: ischaemic cardiomyopathy.

The myocardial sample (25 mg) obtained from explanted hearts was ground and homogenized in TriPure isolation reagent. The gene and proteic expression of lipoproteic receptors LRP1, VLDLR and LDLR was determined by means of real-time PCR and Western blot analysis, respectively.

TABLE 4

Lipoprotein receptor gene expression in the myocardium in cardiac insufficiency, by etiology.

| | Control (n = 4) | DCM (n = 26) | ICM (n = 29) |
|---|---|---|---|
| LRP1 | 9.53 ± 3.14 | 7.65 ± 3.45 | 12.33 ± 11.53*# |
| VLDLR | 28.85 ± 9.66 | 22.01 ± 12.04 | 27.30 ± 14.92 |
| LDLR | 11.14 ± 10.90 | 3.19 ± 1.94* | 3.75 ± 4.57* |

The frozen myocardial tissue (25 mg) was ground and homogenized in the TriPure isolation reagent. LRP1, VLDLR and LDLR gene expression was determined by real-time PCR. Data were processed by means of a software program based on the Ct value and were normalized by the expression of the endogenous 18srRNA control. Controls; DCM: dilated cardiomyopathy; ICM: ischaemic cardiomyopathy. Data were expressed as the mean±SD. *P<0.05 vs. controls. #P<0.05 vs. DCM.

Figure 8B:
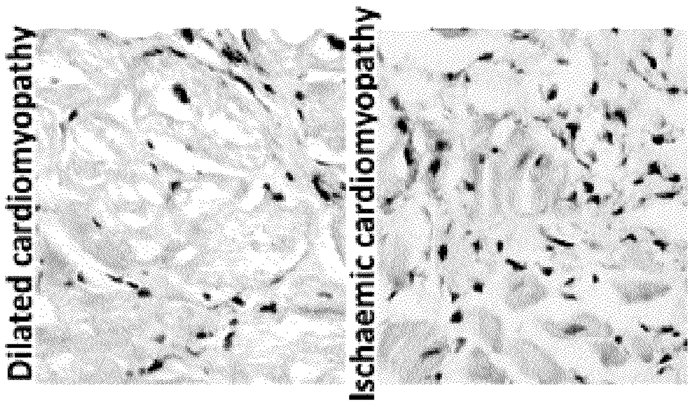
Figure 8A:
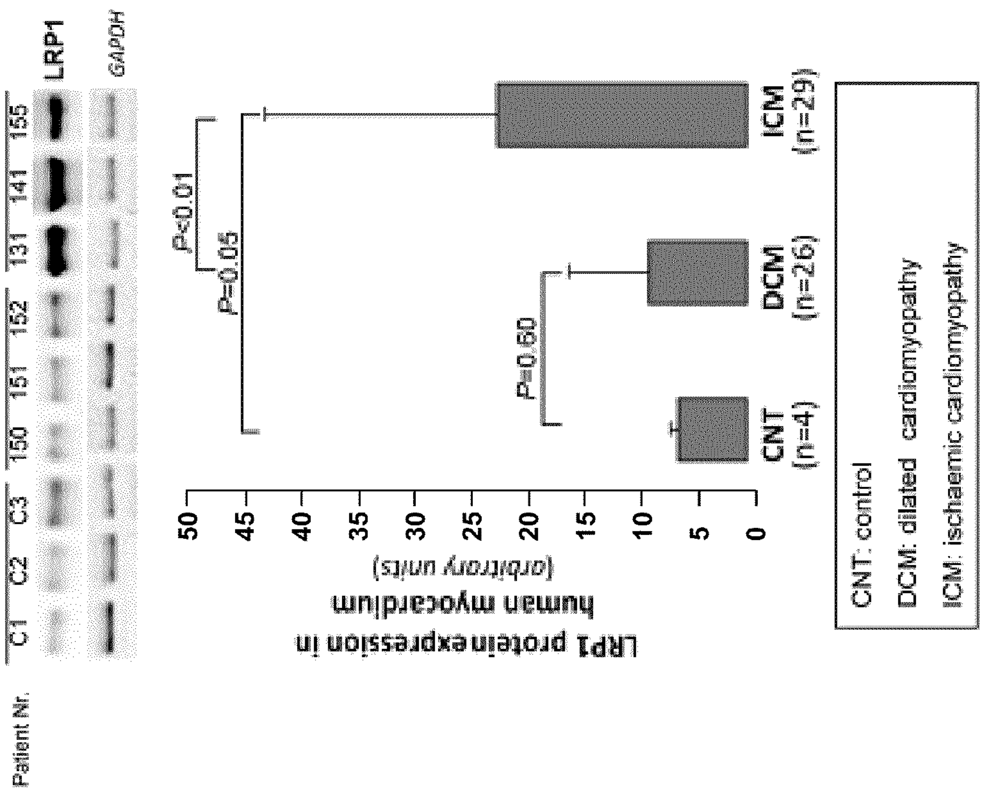
Figure 9B:
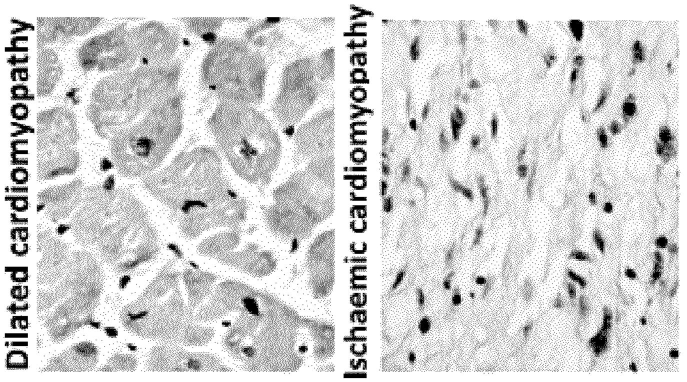
Figure 9A:
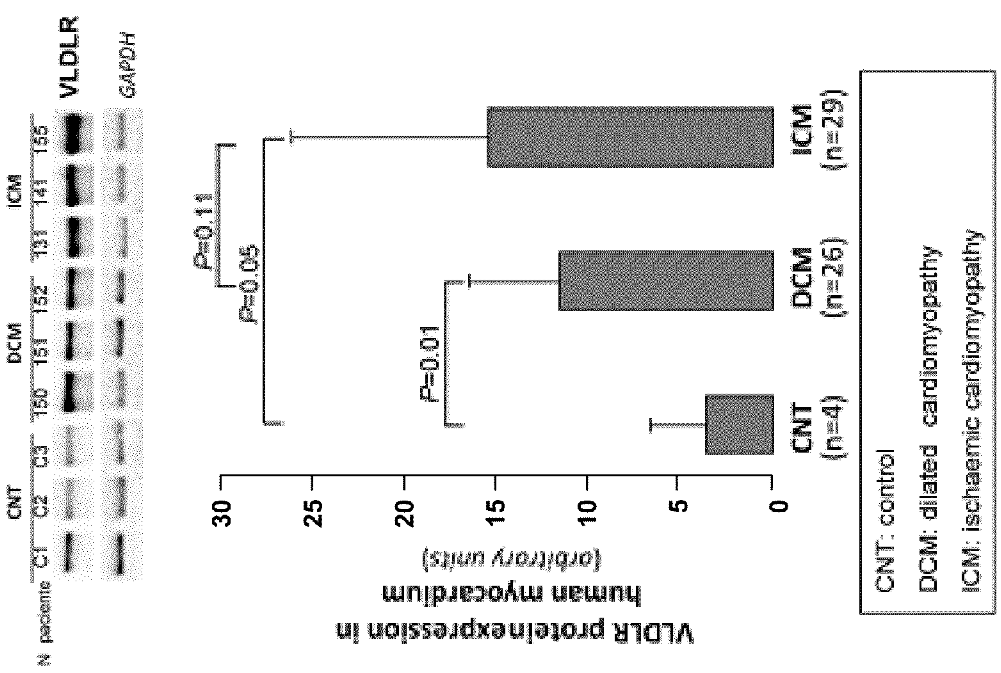

Compared to expression in DCM and control hearts, hearts from ICM patients showed increased levels of LRP1 both at mRNA level (12.33±11.53 vs. 7.65±3.45 or 9.53±3.14, P<0.05) (Table 4) and protein level (22.27±20.66 vs. 8.64±7.22 or 6.11±0.74, P<0.05) (FIG. 8A). These results were also corroborated by immunohistochemistry (FIG. 8B). On the contrary, VLDLR expression at protein level was increased by cardiomyopathy, independently of its etiology (ICM: 15.48±10.61 and DCM: 11.64±4.90 vs. CNT: 3.68±2.98, P=0.05 and P=0.01, respectively) (FIG. 9A). Immunohistochemical results confirmed the absence of differences in VLDLR expression between myocardium of DCM and ICM patients (FIG. 9B). LDL receptor decreased in cardiomyopathic situations independently of its etiology (ICM: 3.75±4.57 and DCM: 3.19±1.94 vs. 11.14±10.90, P=0.016 y P=0.012, respectively) (Table 4).

Example 7

Analysis of Neutral Lipid Levels in Myocardium Samples from Control Subjects, Patients with Idiopathic Dilated Cardiomyopathy (DCM) or with Ischaemic Cardiomyopathy (ICM)

Figure 10A:
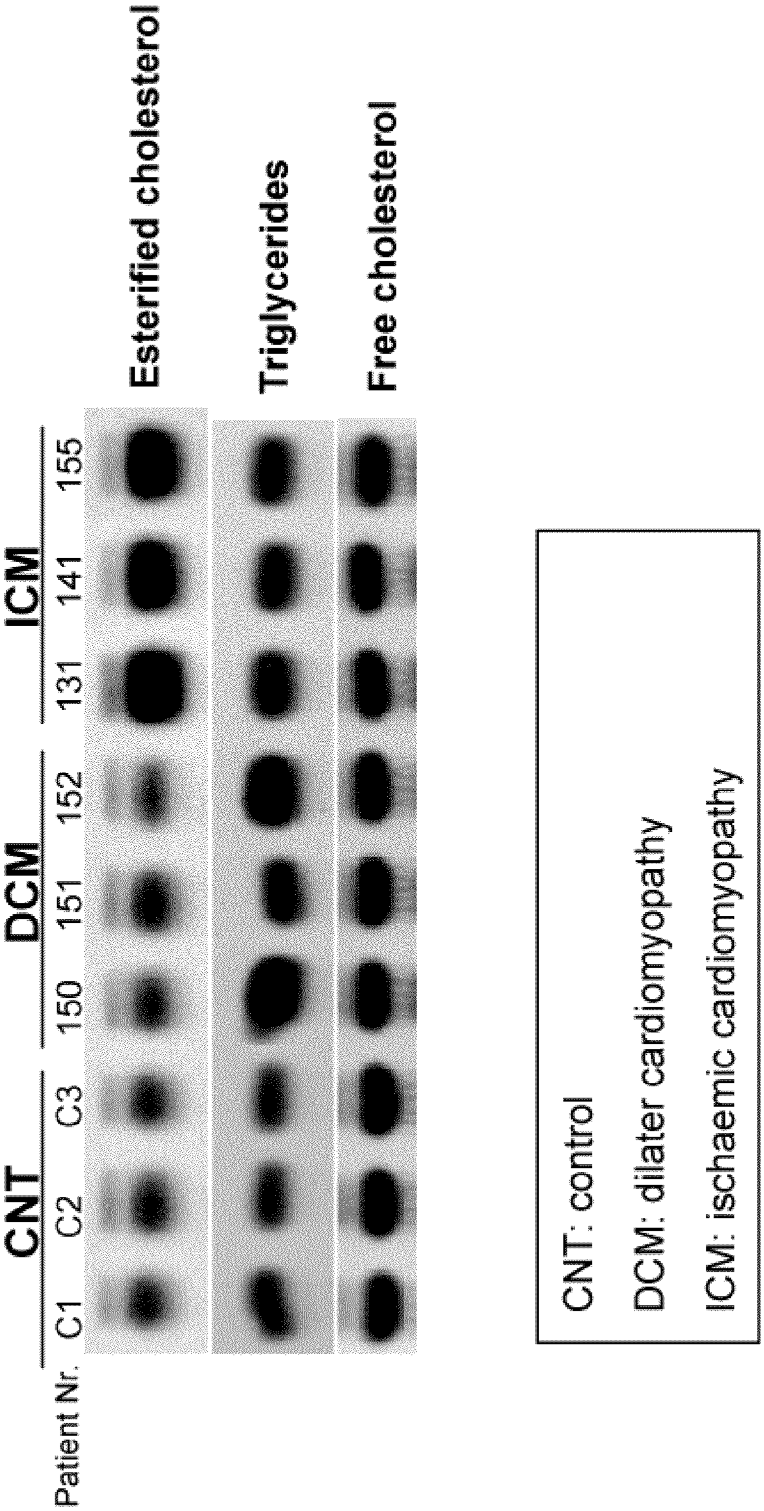
Figure 10B:
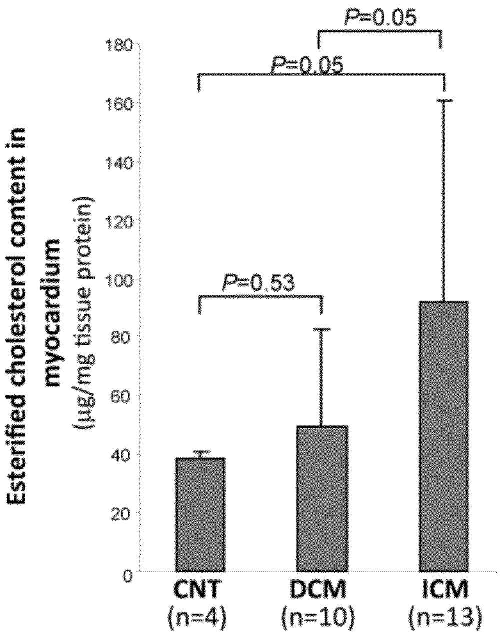
Figure 10C:
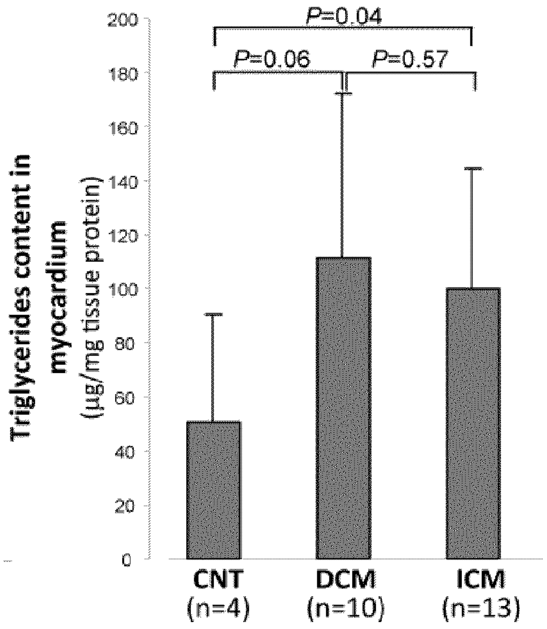
Figure 10D:
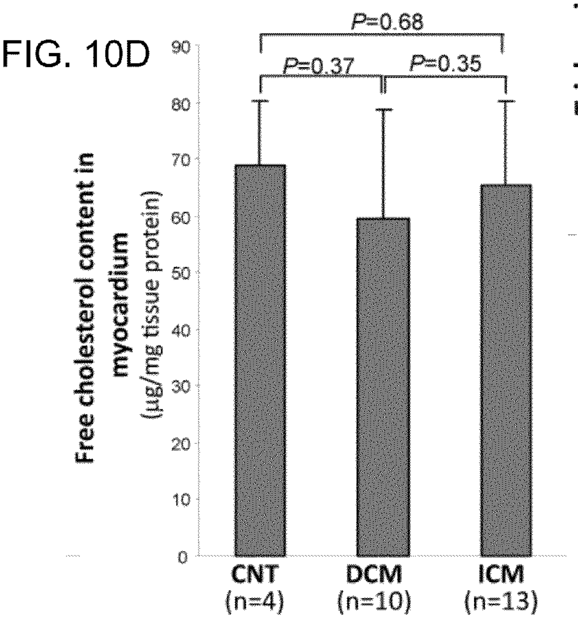
Figure 11B:
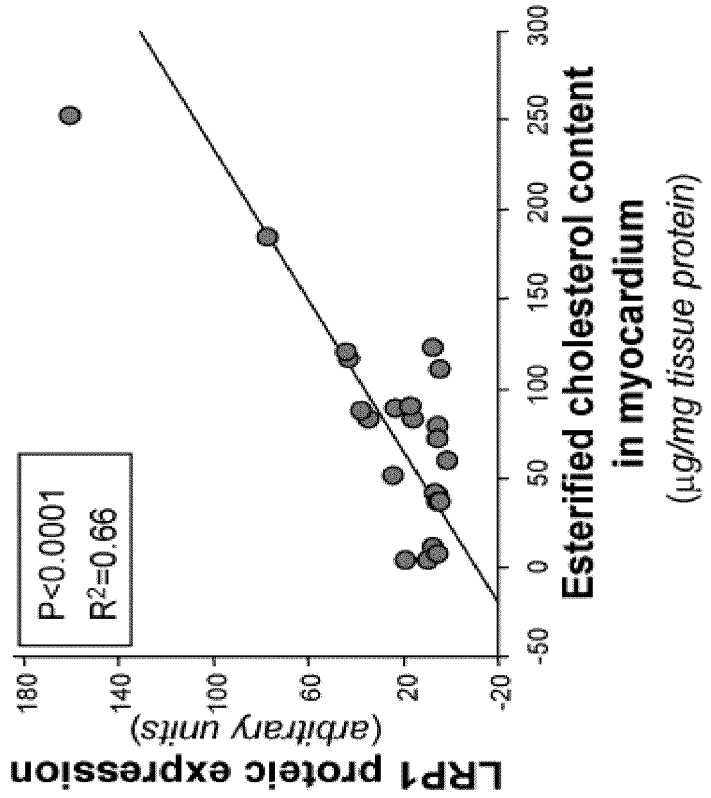
Figure 11A:
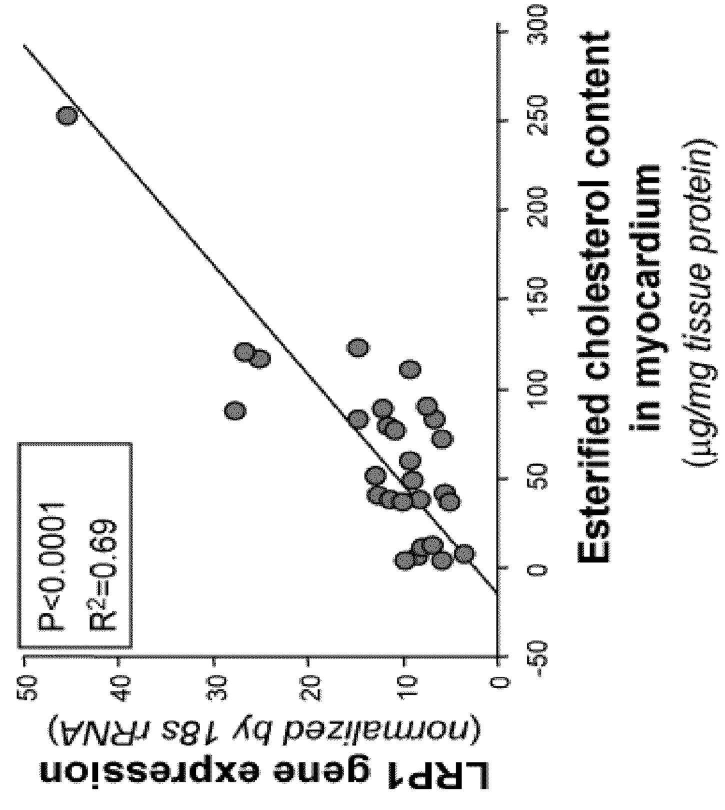
Figure 12B:
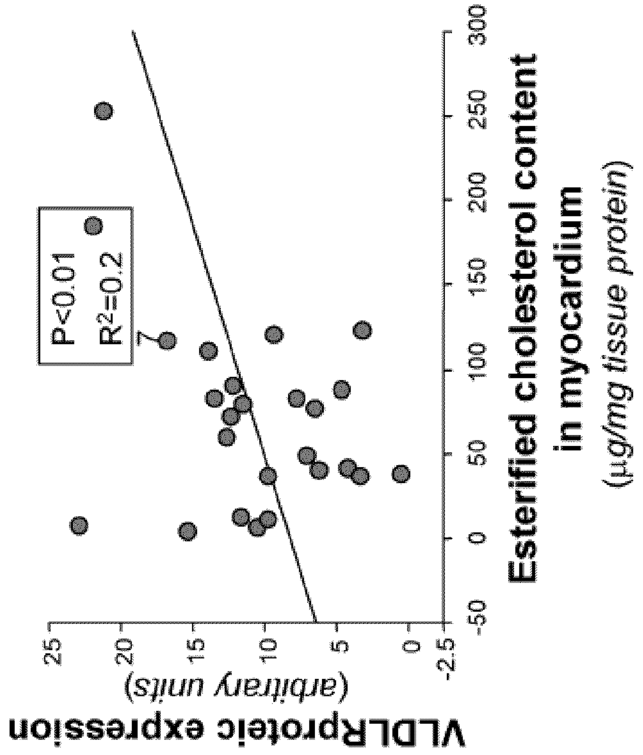
Figure 12A:
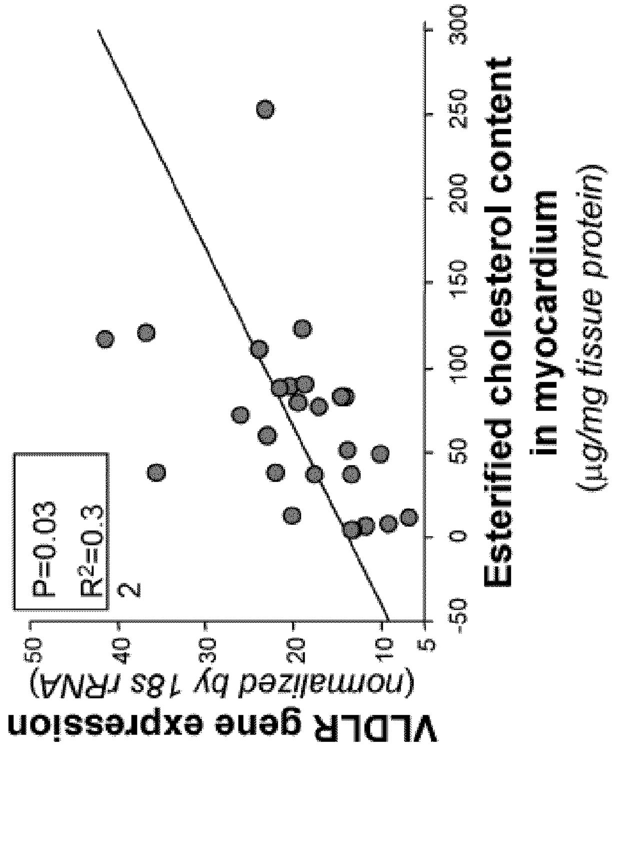

The thin-layer chromatography results (FIG. 10A) demonstrated that the myocardium from patients with ICM had higher levels of CE than those of patients with DCM or controls (92.2±68.3 vs. 49.7±9.9 or 39.0±1.8, P=0.05) (FIG. 10B). Although the TG level was higher in the myocardium from patients with DCM or ICM with respect to the controls (111.3±60.7 and 100.2±44.4 vs. 50.8±39.4, P=0.05 and P=0.04) (FIG. 10C), no significant differences were observed among these two groups of patients. There were no differences in free cholesterol content in hearts from the different groups studied (FIG. 10D). It was found that LRP1 myocardial expression correlated very significantly with CE content both at mRNA level ($R^2$=0.69, P<0.0001) (FIG. 11A) and at protein level ($R^2$=0.66, P<0.0001) (FIG. 11B). In a lower grade than with LRP1, VLDLR myocardial expression also positively correlated with CE content at mRNA level ($R^2$=0.32, P=0.03) (FIG. 12A) and at protein level ($R^2$=0.27, P<0.01) (FIG. 12B). The correlation between LRP1 or VLDLR and cholesteryl ester content in the heart was specifically observed in the ischaemic cardiomyopathy group (Table 5).

TABLE 5

Correlations between lipoprotein receptor expression and cholesteryl ester content in myocardium, by etiology of the cardiac insufficiency.

| | DCM (n = 10) | | ICM (n = 13) | |
|---|---|---|---|---|
| | $R^2$ | P | $R^2$ | P |
| LRP1 mRNA | 0.012 | 0.075 | 0.74 | <0.0001 |
| LRP1 protein | 0.032 | 0.65 | 0.78 | <0.0001 |
| VLDLR mRNA | 0.001 | 0.93 | 0.27 | 0.05 |
| VLDLR protein | 0.031 | 0.63 | 0.33 | 0.05 |

DCM: dilated cardiomyopathy,
ICM: ischaemic cardiomyopathy.

Example 8

Hypoxia does not Increase LRP1 Expression in HIF-1α-Deficient Cardiomyocytes

Figure 13A:
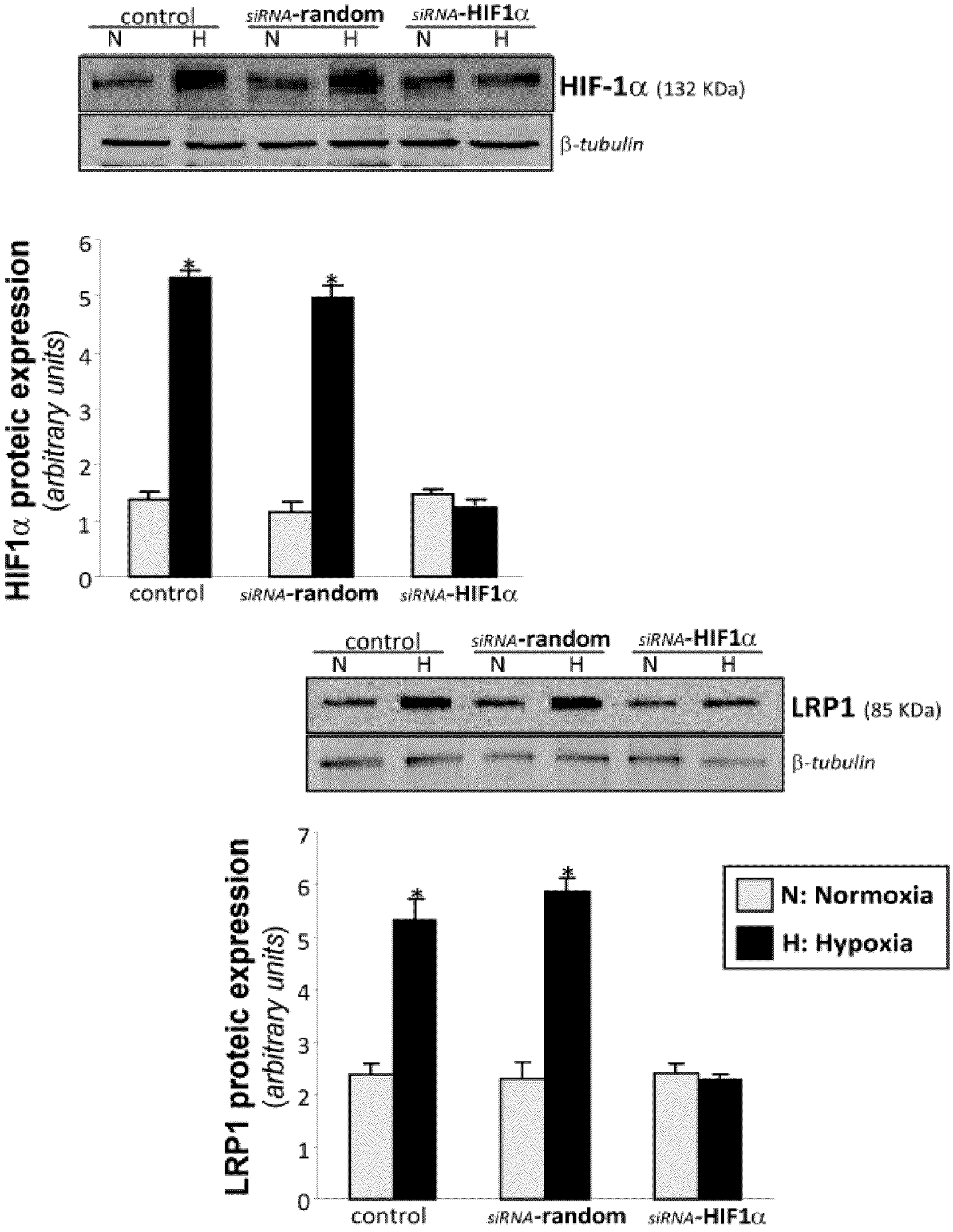
Figure 13B:
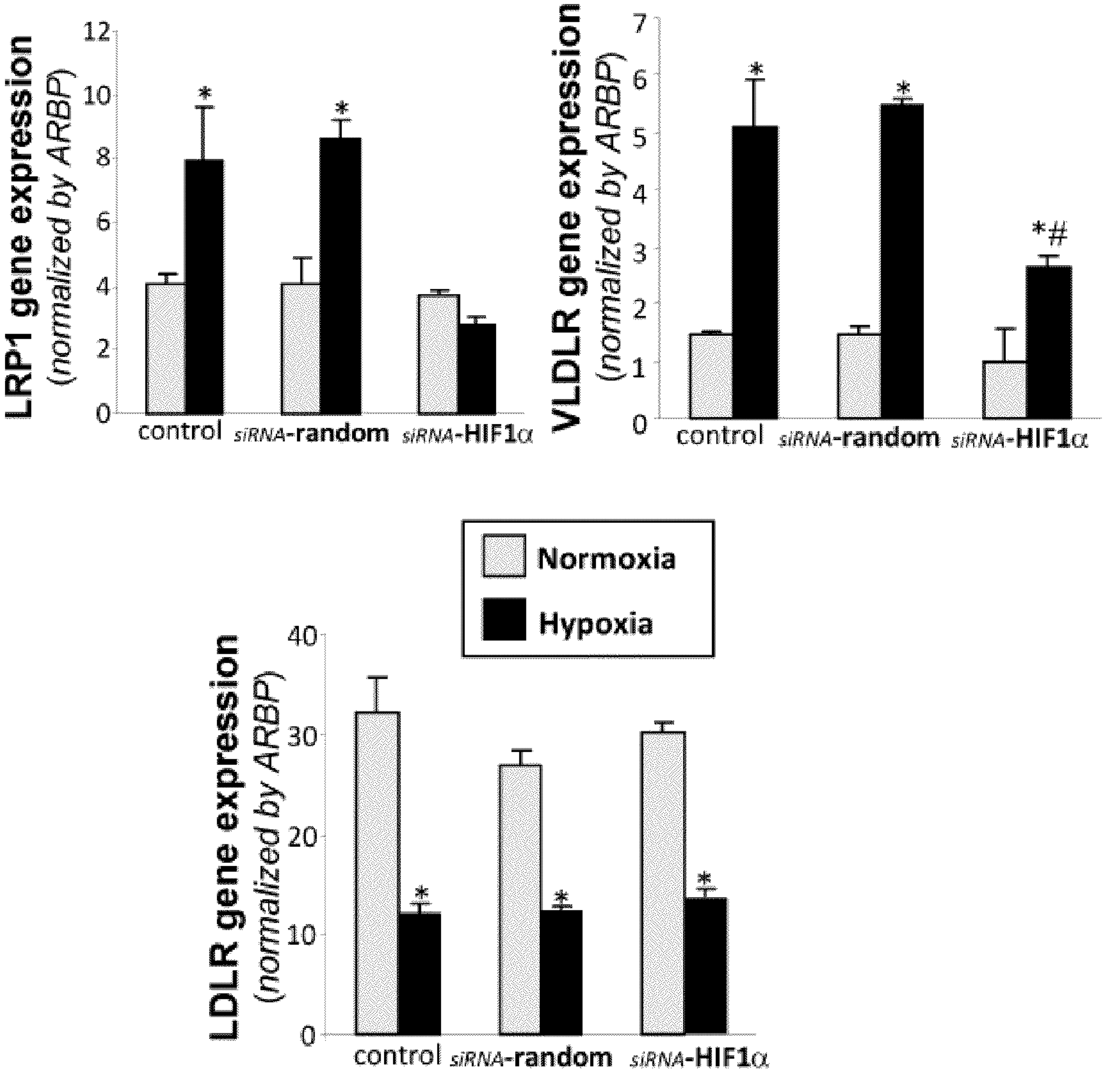

To analyze the role of HIF-1α in the upregulatory effect of hypoxia on LRP1 expression, HIF-1α was inhibited with a specific siRNA (Applied Biosystems, siRNA ID 4390815) by a nucleofection technique. siRNA-anti HIF1α, though not the unspecific siRNA-random, completely prevented the increase in HIF-1α (3.8-fold) induced by hypoxia (FIG. 13A, left panel) in HL-1 cardiomyocytes. Hypoxia does not exert any significant effect on LRP1 expression in HIF-1α-deficient HL-1 cardiomyocytes (FIG. 13A, right panel). In contrast, hypoxia significantly increases LRP1 expression in control and siRNA-random transfected HL-1 cardiomyocytes. As shown in FIG. 13B, real-time PCR experiments show that HIF-1α inhibition efficiently prevents the upregulatory effect of hypoxia on LRP1 and VLDLR expression. However, HIF-1α inhibition does not exert any significant effect on the downregulatory effect of hypoxia on the classical receptor for LDL (LDLR).

Example 9

Figure 14A:
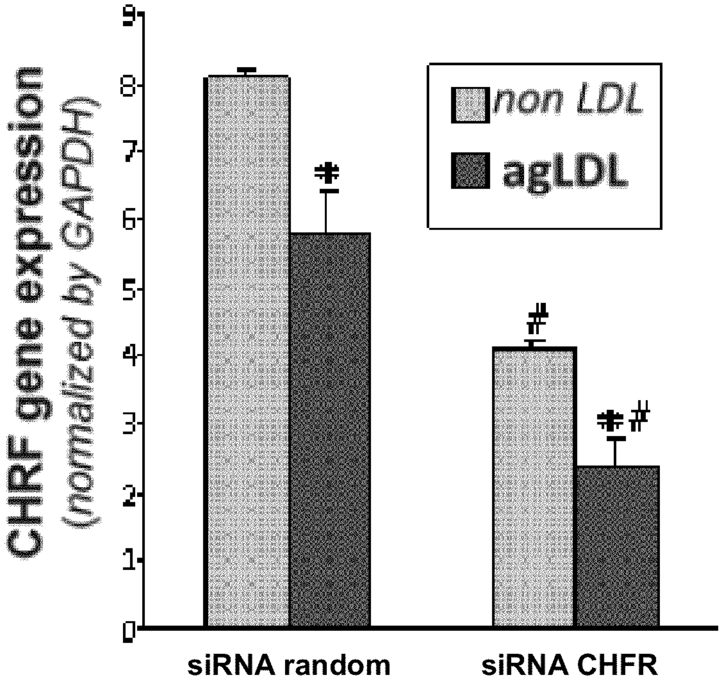
Figure 14B:
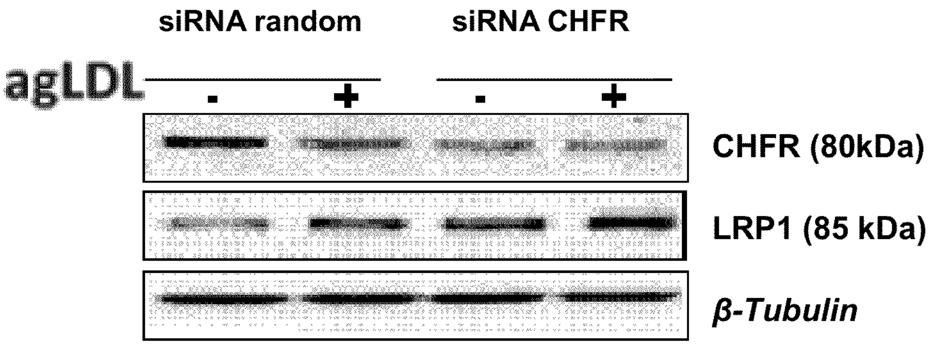
Figure 14D:
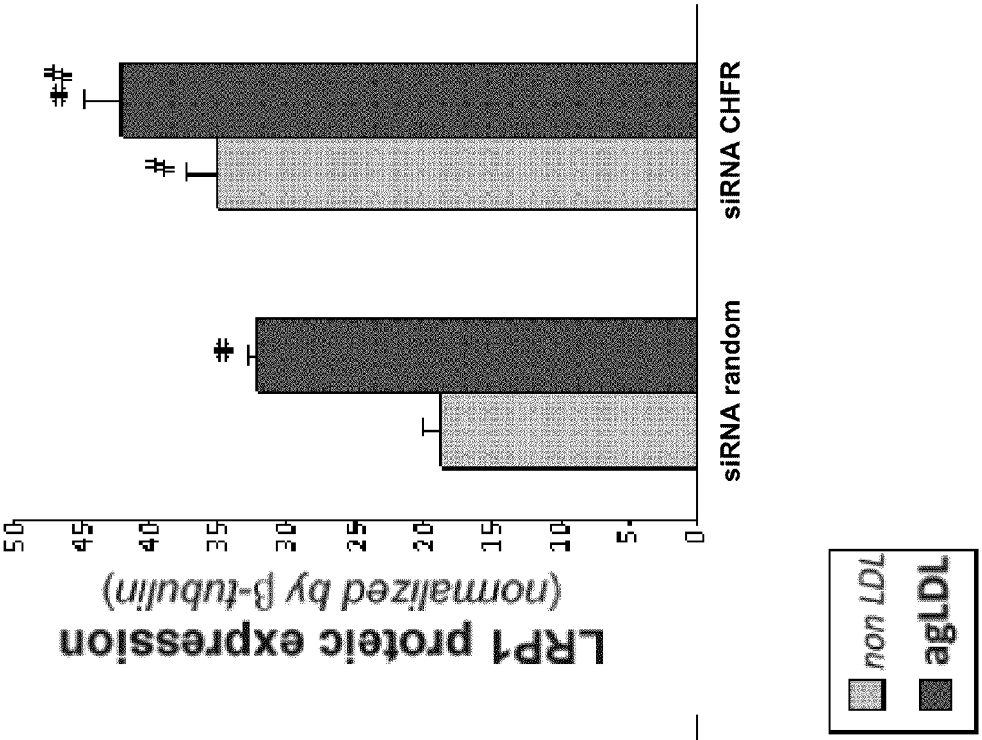
Figure 14C:
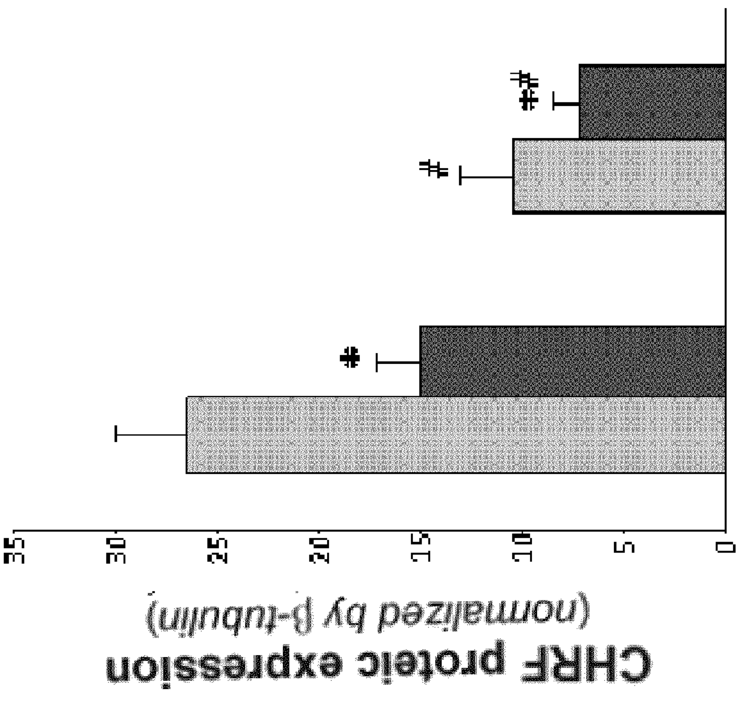
Figure 15A:
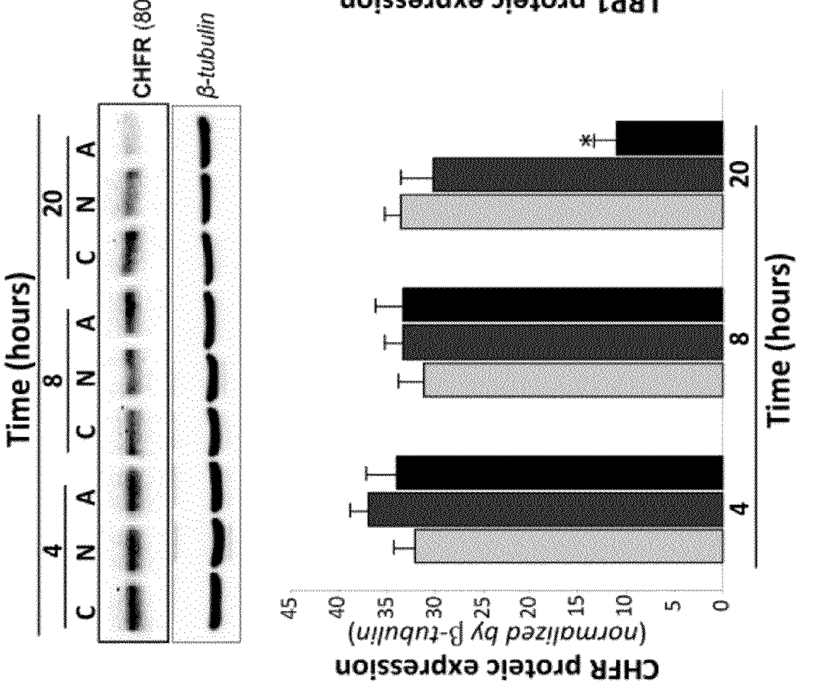
Figure 15B:
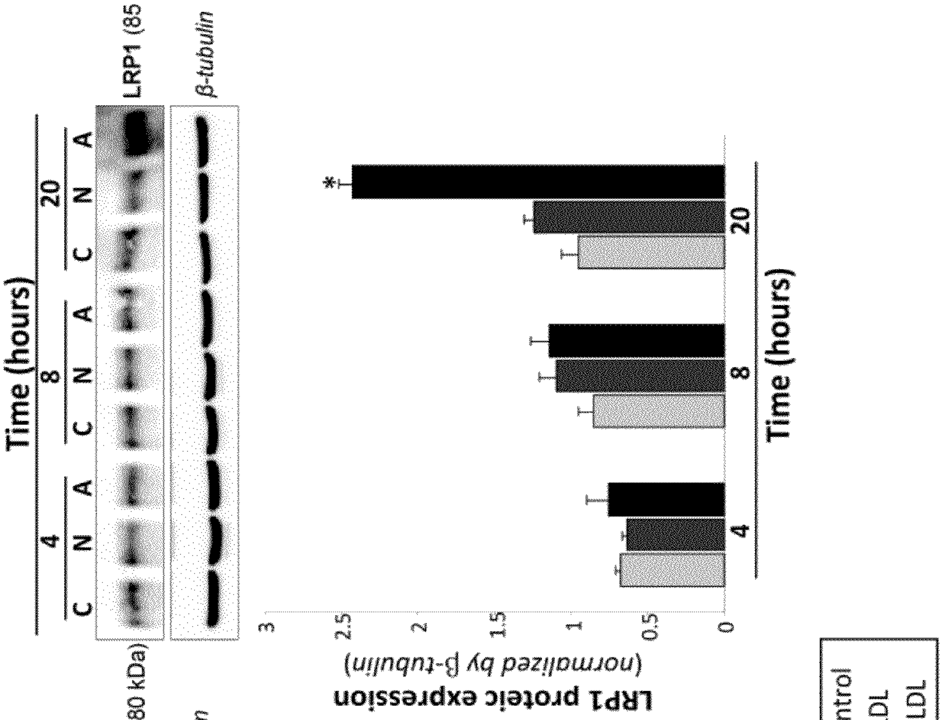
Figure 15D:
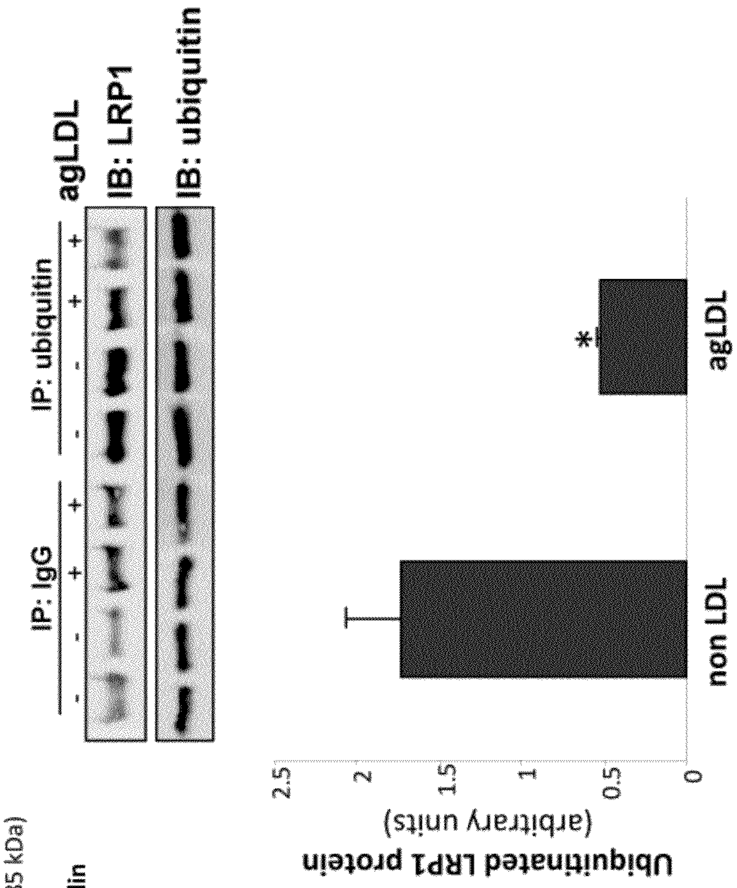
Figure 15C:
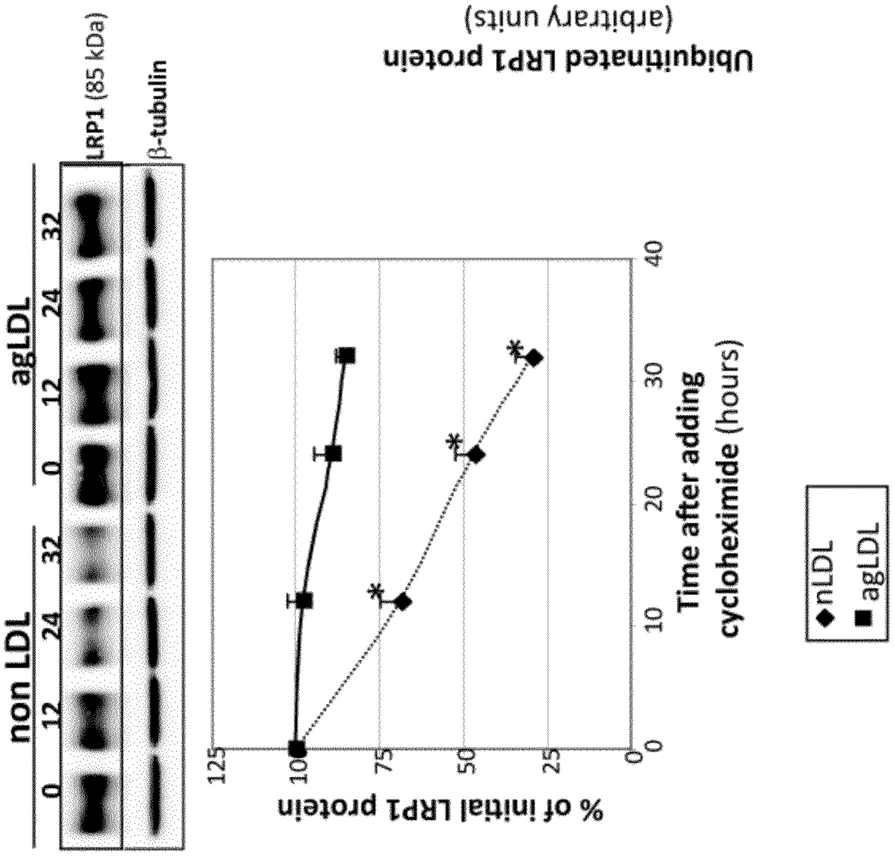

E3 CHFR Ubiquitin Ligase Protein Modulates LRP1 Protein Stability and Mediates the Effect of Aggregated LDL in the Ubiquitination of the LRP1 Beta Chain In order to discover the effect of the protein CHFR on LRP1 protein levels, CHFR mRNA expression was silenced though nucleofection by specific siRNA. As shown in FIG. 14A, both siRNA-CHFR (Applied Biosystems, siRNA ID s 31393) and aggregated LDL (agLDL) (100 μg/mL) decreased CHFR mRNA expression by 70% and 50%, respectively. The simultaneous exposure of cells to siRNA-CHFR and agLDL reduces CHFR mRNA expression up to 30%. In line with these results, Western blot experiments show that CHFR protein levels were reduced by 56% with agLDL, by 39% with siRNA-CHFR and by 27% by both interventions applied together (FIG. 14B & FIG. 14C). Concomitantly with CHFR reduction, LRP1 expression was increased by agLDL (1.72-fold), by siRNA-CHFR (1.9-fold) and by joint interventions (2.26-fold) (FIG. 14B & FIG. 14D). As shown in FIG. 15A, agLDL (100 μg/mL, 20 hours) reduced CHFR protein expression by 33% and increased LRP1 protein expression 2.5-fold. CHFR decrease induced by agLDL leads to a reduction in LRP1 beta chain ubiquitination (FIG. 15B) and to an increase in LRP1 protein half-life (FIG. 15C).

Example 10

Anti-P2 and Anti-P3 Antibodies Reduce the Intracellular Accumulation of Cholesteryl Ester Induced by Aggregated LDL Internalization in Human Vascular Smooth Muscle Cells Exposed to Hypoxic Conditions As shown in FIG. 16, anti-P2 and anti-P3 antibodies were able to efficiently compete with aggregated LDL (agLDL) for LRP1 binding. Therefore, anti-P2 and anti-P3 antibodies efficiently and significantly inhibit intracellular cholesteryl ester accumulation derived from agLDL uptake. Anti-P2 and anti-P3 antibodies decrease intracellular cholesteryl ester accumulation by 50% and 30%, respectively, in hypoxic human vascular smooth muscle cells (VSMC).

Example 11

Anti-P1 Antibodies Reduce the Intracellular Accumulation of Cholesteryl Ester Originating from the Uptake of VLDL in Hypoxic Cardiomyocytes As shown in FIG. 17, anti-P1 antibodies were able to efficiently compete with VLDL and to significantly inhibit intracellular cholesteryl ester accumulation originating from VLDL uptake by 56% in hypoxic HL-1 cardiomyocytes.

Example 12

Milestone I. Obtaining Monoclonal Antibodies and Small-Size Molecules for Application in In Vivo Models of Acute Myocardial Infarction On the basis of polyclonal antibodies obtained following the procedure described in this report, monoclonal antibodies and small size molecules are obtained, which are able to inhibit the uptake of cholesteryl ester from VLDL by cardiomyocytes in in vivo models.

To carry out this task, we have worked in collaboration with the Antibody Production Service of the Universidad Autönoma de Barcelona (director: Antoni Iborra). Antibody purification and endotoxin removal are also carried out, so as to be able administer the antibodies in the in vivo model.

Milestone II. Role of the Inhibition of the Receptor LRP1 in Cardioprotection in In Vivo Models of Acute Myocardial Infarction The effect of the molecules developed in milestone I are studied in:

IIa. Cardiomyocyte Cell Cultures.

IIb. In Vivo Models of Acute Myocardial Infarction: Mouse and Pig.

Milestone II takes place in the Cardiovascular Research Center, CSIC-ICCC, which is equipped with laboratories, equipment and specialized scientific researchers in order to successfully carry out the following experimental procedures: cell cultures, animal facility, genomics platform, proteomics laboratory, confocal microscopy with resonance scanner, immunohistochemistry and immunocytochemistry platforms, and flow cytometry platform.

*Each one of these platforms is run by a postdoctoral researcher. The center has the platforms and methodology required to carry out most of the studies. Most of the technology required is already up and running and has been adapted to suit the objectives set out by this project.

Example 13

Materials and Methods 13.1 Cell Cultures

I. HL-1 Cell Line Cultures

The HL-1 cell line was kindly provided by Dr. W. C. Claycomb (Louisiana State University Medical Centre, New Orleans, La., USA). These cells show similar characteristics to those of cardiomyocytes. These cells were kept in Claycomb medium (JRH Biosciences, Leneka, Kans., USA) supplemented with 10% of foetal calf serum (Invitrogen Corporation, Carlsbad, Calif., USA), norepinephrine (100 μM), penicillin (100 U/mL), streptomycin (100 μg/mL) and amphotericin (0.25 μg/mL) in cell culture dishes covered with fibronectin (12.5 μg/mL) and gelatine (0.02%) at 37° C. and at 5% $CO_2$.

II. Isolation and Cell Culture of Neonatal Rat Ventricular Myocytes (NRVM)

This study was approved by the Animal Research Committee of the Instituto Catalan de Ciencias Cardiovasculares (ICCC020/DMAH4711) and was carried out according to the Guide for the Care and Use of Experimental Animals published by the U.S. National Institute of Health. The NRVM cells were prepared from the ventricles of hearts of rats 3-4 days old. The neonates were killed by decapitation, their hearts were extracted and Atria separated. Homogeneous solutions were prepared using the kit "Neonatal Cardiomyocyte Isolation System" (Worthington Biochemical Corporation), following the manufacturer's instructions. Cardiomyocytes were separated from cardiac fibroblasts by pre-seeding these in plastic wells at 37° C. and 5% $CO_2$ for 90 min. The cardiomyocytes were maintained in wells covered with 1% gelatin in DMEM:M199 (Gibco) supplemented with 5% FBS, 10% horse serum (Invitrogen) and 1% P/S. 1 μg/mL of cytosine b-D-arabinofuranoside (Sigma) was added to the culture medium to inhibit residual proliferation of fibroblasts. The culture medium was changed every other day. After 48 hours of culture, myocytes exhibited regular spontaneous contraction. Cells were used for experiments after 3-6 days in culture.

III. Generation of LRP1-Deficient Cardiomyocytes

Design of miRNA Lentivirus to Inhibit LRP1 Expression

A) Different miR RNAi sequences were designed using the Invitrogen BLOCK-IT™ RNAi Designer system to inhibit LRP1 expression (XM_001056970) by incorporation into lentiviruses used to infect HL-1 and NRVM:

- the sequences SEQ ID No: 1 and SEQ ID No: 2 correspond to the top and bottom oligonucleotides of miR RNAi designed and artificially synthesized to inhibit LRP1 expression (miR RNAi-XM_001056970_1919 or RNAi1919);
- the sequences SEQ ID No: 3 and SEQ ID No: 4 correspond to the top and bottom oligonucleotides of miR RNAi designed and artificially synthesized to inhibit LRP1 expression (miR RNAi-XM_001056970_8223 or RNAi8223);
- the sequences SEQ ID No: 5 and SEQ ID No: 6 correspond to the top and bottom oligonucleotides of miR RNAi designed to inhibit LRP1 expression (miR RNAi-XM_001056970_8531 or RNAi8531);

The plasmid pcDNA™ 6.2-GW/miR was used as a negative control in all transfection experiments: SEQ ID No: 7 and SEQ ID No: 8 correspond to the top and bottom oligonucleotides of the universal negative control (pcDNA™6.2-GW/miR-neg).

B) Analysis of LRP1 mRNA expression in HL-1 cells infected with RNAi1919 (SEQ ID No: 16), RNAi8223 (SEQ ID No: 17) or RNAi8531 (SEQ ID No: 18) (FIG. 3). The data were processed with a software program based on the relative calculation of mRNA concentration according to the Ct value (threshold cycle). The data were normalized by the endogenous control ARBP. The results were expressed as the percentage of expression compared to the cells infected with the negative control. *P<0.05 vs. cells transfected with the negative control.

In our case, the program has generated three sequences with the ability to inhibit the gene LRP1 [RNAi1919 (SEQ ID No: 16), RNAi8223 (SEQ ID No: 17) or RNAi8531 (SEQ ID No: 18)] in addition to the negative control (pcDNA™-GW/ miR_neg). The pcDNA™-GW/miR_neg plasmid contains an insert which forms a hairpin structure that is processed in a mature miRNA that is unable to bind to any known genes in vertebrates. Therefore, this plasmid serves as a negative control for the knockdown experiments carried out with pcDNA™6.2-GW/miR expression vectors. The artificially-synthesized sequences SEQ ID No: 9 and SEQ ID No: 10, which correspond to sequences of DNA of vectors pLenti6.4™-CMV-MSGW and pcDNA™6.2_GW, respectively, were also used.

IV. Production of the Lentivirus Particles

In order to generate the miR RNAi expression vector, oligos were annealed and ligated into the linear vector pcDNA™6.2_GW/miR (SEQ ID No: 10). Subsequently, competent *E. coli* cells were transformed with the ligated DNA and cells were selected in LB medium supplemented with 50 μg/mL of spectinomycin. miR RNAi constructs were then transferred to pDONR™221 (SEQ ID No: 11) vectors through the reaction catalyzed by the BP clonase II (FIG. 4B).

The sequence miRNA of the clone pENTR™221 (SEQ ID No: 12) was then transferred together with the pENTR5'-CMV plasmid (Invitrogen) to the pLenti6.4/R4R2/V5-DEST™ vector (SEQ ID No: 23) using the reaction catalyzed by LR clonase II (FIG. 4C). The artificially synthesized sequences SEQ ID No: 11 and SEQ ID No: 12, which correspond to the DNA sequences of the vectors pDONR™221 (SEQ ID No: 11) and pENT™221 (SEQ ID No: 12), were also used.

Competent *E. coli* cells were transformed with the recombinant expression vector pLenti6.4™-CMV-V5-MSGW/miR (Life Technologies (Invitrogen)) and the cells were selected in ampicillin-supplemented LB medium. Colonies were picked and grown overnight in LB medium with ampicillin. Digestion with Hind was performed to verify a correct recombination. Lentiviruses (preferably pLenti6.4™-CMV-MSGW/miR-XM-001056970-1919 (SEQ ID No: 21); pLenti6.4™-CMV-MSGW/miR-XM-001056970-8223 (SEQ ID No: 24); pLenti6.4™-CMV-MSGW/miR-XM-001056970-8531 (SEQ ID No: 20); pLenti6.4™-CMV-MSGW/miR-neg (Life Technologies (Invitrogen)) were used to transfect HL-1 cardiomyocytes and NRVM.

The day before transfection, 293T human embryonic kidney cells were seeded. The lentiviral transfer vector (pLenti6.4-CMV-MSGW/miR, 6 μg) (SEQ ID No 9), the viral envelope plasmid (pMD-G-VSV-G, (Sigma-Aldrich), 2 μg), and the packaging construct (pCMV-ΔR8.2 (SEQ ID No: 22), 4 μg) were mixed with 150 mM sodium chloride and the mixture was added to a solution called "Polyplus transfection". The mixture was incubated at room temperature for 20 min. This solution was added dropwise to the 293T cells which were incubated for 16 hours at 37° C. and with 5% $CO_2$. The next day, the transfection solution was removed, and medium without FBS was added to the cells. After 48 hours of incubation, the supernatant was collected, and it was centrifuged and filtered through a 0.45 μm low-binding filter. The filtered supernatant was concentrated using Amicon filters according to the manufacturer's instructions. The various stocks that were generated, as well as the negative lentivirus control were titrated using the blasticidin method.

V. Generation of LRP1-Deficient Cardiomyocytes

In the transient transfection experiments, confluent NRVM were incubated for 18 hours in the presence of lentiviruses with 10 MOI. In stable transfection experiments, three days after infection with the virus, the HL-1 cells were treated with blasticidin (10 μg/mL). The medium was replaced with fresh medium containing blasticidin every 3 or 4 days until blasticidin-resistant colonies were identified. The clones with maximum inhibition of LRP1 expression were selected and grown.

13.2 Preparation of Human Smooth Muscle Cells from the Vascular Wall

The VSMC were obtained from human coronary arteries according to the explantation technique established by our group (Llorente-Cortés et al, *ATVB* 2000; Llorente-Cortés et al, *Circulation* 2002). To perform the experiments, VSMCs that had been thawed or subcultured between the 3rd and 7th passage. For treatment under normoxic conditions (21% $O_2$), a Nirco incubator with an atmosphere of 74% $N_2$ and 5% $CO_2$ was used. For hypoxia, a Don Whitley Scientific Ltd. Anoxic Workstation H35de was used with a gas mixture of 1% $O_2$, 94% $N_2$, 5% $CO_2$.

13.3 Isolation and Characterization of VLDL and LDL

The human VLDL ($d_{1.001}$-$d_{1.019}$ g/mL) and LDLs ($d_{1.019}$-$d_{1.063}$ g/mL) were obtained from a pool of sera from normolipidemic volunteers. The VLDL and LDL preparations used for the experiments were always less than 24 hours old and with no detectable levels of malonaldehyde or endotoxin. The modification of LDL by aggregation was performed mechanically (Llorente-Cortés et al, *ATVB* 1998). Native LDLs were brought to a concentration of 1 mg/mL by diluting them in PBS buffer, whereupon the preparation was vigorously stirred using a vortex mixer at room temperature (RT) for 4 minutes. Subsequently, the preparation was centrifuged at 10000×g at RT for 10 minutes to precipitate agLDL, and the supernatant was discarded. The agLDL were resuspended in PBS up to a protein concentration of 1 mg/mL. The agLDL obtained by centrifugation has a structure and functionality similar to that produced by incubation with versican proteoglycans of the extracellular matrix (Llorente-Cortés V et al, 2002 *ATVB*).

13.4 Measurement of the LRP1 Protein's Stability

In order to measure the stability of the protein LRP1, cycloheximide, an inhibitor of translation in eukaryotes, was used. VSMCs were pre-exposed to agLDL (100 μg/mL) for 18 hours before the addition of cycloheximide (100 μM). The cells were then collected at the following times after treatment with cycloheximide (6, 12, 24 and 32 hours), were harvested in lysis buffer, and then LRP1 protein concentration was analyzed using Western blot. The stability of the LRP1 protein was determined as the proportion of initial protein that remained at each time after treatment with cycloheximide.

13.5 Immunoprecipitation of the Ubiquitinated LRP1 Protein

The polyubiquitinated proteins were immunoprecipitated using the Ubiquitinated Protein Enrichment Kit (Calbiochem 662200). One aliquot of the protein extract was applied to poly-ubiquitin-enriched beads, and another aliquot was applied to negative control beads. After immunoprecipitation, the membranes were incubated with anti-LRP1 antibodies (Epitomics, 2703-1, dilution 1:7000) and with anti-ubiquitin antibodies (Calbiochem, 662099, dilution 1:5000).

13.6 Production of Polyclonal Antibodies

I. Synthesis of Peptides:

Three peptides were designated on the basis of sequence cluster II of alpha chain of LRP1 (SEQ ID No: 19). The sequences of these peptides and their locations are:

Peptide 1 (P1): CTNQATRPPGG<u>S</u>HTDE (SEQ ID No: 13). <u>S</u> replaces the C of the original human LRP1 sequence (1051-1066).

Peptide 2 (P2): DSSDEKS<u>S</u>EGVTHVC (SEQ ID No: 14). <u>S</u> replaces the C of the original human LRP1 sequence (1090-1104).

Peptide 3 (P3): GDNDSEDNSDEENC (SEQ ID No: 15). S replaces the C of the original human LRP1 sequence (1127-1140).

These peptides were synthesized in the Separative Techniques and Peptide Synthesis Unit, at the University of Barcelona, through a solid-phase method using a peptide synthesizer. Peptides were then purified by high-performance liquid chromatography (HPLC) using UV detection at 254 nm. The purified peptides were characterized using mass spectrometry. The peptides were then coupled to the carrier KLH for immunization and to the carrier albumin to test the antibodies generated using the ELISA technique.

II. Immunization of Animals:

Production of polyclonal antibodies was performed at the Department of Cell Culture, Antibody Production and Cytometry, at the Universidad Autónoma de Barcelona (UAB). The animal study was approved by the Animal Research Committee of the UAB and by the Catalan government. For each peptide, two groups of three Balb/c mice (8 weeks old) were immunized intraperitoneally with 50 micrograms of the peptides conjugated to KLH. A small amount of blood was drawn to test for the presence of antibodies against the peptides using the ELISA method.

The mouse serum was collected following the immunization guidelines. The specific antibodies for each peptide were purified by immobilizing the peptides in SulfoLink affinity columns according to the manufacturer's instructions, and their levels were analyzed using ELISA.

III. ELISA

The levels of specific antibodies in the serum samples as well as those of the purified anti-peptide antibodies were determined using ELISA. Briefly, peptides conjugated to BSA and BSA alone were immobilized in 96-well plates at a concentration of 1 μg/mL in 0.1 M carbonate buffer and pH 9.6 for 60 minutes. After blocking with 1% BSA in PBS, the plates were incubated with primary antibodies at different dilutions, followed by incubation with peroxidase-linked secondary antibody. The enzymatic reaction was performed in a Sigma-Fast OPD device. After 30 minutes, the optical density was measured at 450 nm on a plate reader.

13.7 Lipid Extraction and Determination of Esterified Cholesterol (CE), Free Cholesterol (FC) and Triglyceride (TG) Content Following incubation with VLDL, the cells were exhaustively washed and collected in NaOH. In the case of myocardial tissue, 5 mg of tissue were weighed, homogenized and triturated in NaOH. The cell or tissue homogenate was used for lipid extraction through the Bligh and Dyer method with minor modifications. Lipid extraction was performed by adding a mixture of methanol/dichloromethane (2:1, vol/vol). After evaporation of the organic solvent, the extract was dissolved in dichloromethane and used for thin-layer chromatography (TLC). TLC was performed on G-24 silica plates. A mixture of standards (cholesterol, cholesterol palmitate, triglycerides, diglycerides and monoglycerides) were applied on each plate. The chromatographic solution was heptane/diethylether/acetic acid (74:21:4, vol/vol/vol). The CE, FC and TG bands were quantified through densitometry against a standard curve of cholesterol palmitate, cholesterol, and triglycerides, respectively, using a densitometer.

13.8 Preparation of Doubly-Labeled VLDL

To prepare doubly-radiolabeled VLDL, a layer of cholesteryl-1,2[$^{3}$H]-(N)(125 μCi) and trioleate glycerol [$^{14}$C] was formed in a round-bottom bottle by evaporating the organic solvent at 37° C. under vacuum. Then, 50 mL of human plasma were added and the bottle was left rotating in a water bath at 37° C. for 30 hours. VLDL were isolated by sequential ultracentrifugation, dialyzed in PD10 columns, and filtered. The specific activity of the VLDLs was 492 cpm/μg of protein for [$^{3}$H] and 102 cpm/μg of protein for [$^{14}$C].

13.9 Determination of VLDL-[$^{3}$H]-CE and VLDL-[$^{14}$C]-TG Uptake by the Cardiomyocytes LRP1-deficient or quiescent HL-1 control cells were incubated with doubly-radiolabeled VLDL (1.8 mM, 18 hours). At the end of the incubation period, the cells were washed and collected in 0.1 M NaOH. The radioactivity counts in 50 μL of cell homogenate were determined in a scintillation counter (Beckman Coulter, LS6500) and the counts (dpm) were normalized by the cellular protein.

13.10 Analysis of the Expression of mRNA and Protein

For the extraction of both mRNA and protein, the cells or tissue were homogenized in the TriPure isolation reagent following the manufacturer's instructions.

I. Expression of Messenger RNA (mRNA)

LRP1 mRNA, VLDLR mRNA, LDLR mRNA and CHFR mRNA expression was analyzed with real-time PCR using the ABIPRISM PCR-7000 Sequence Detection System (Applied Biosystems) with the following assays-on-demand: LRP1 (Rn01503901 or Mm00464601_m1), VLDLR (Rn01498166_m1 or Mm00443281_m1), LDLR (Rn00598440_m1 or Mm01151339_m1) and CHFR (Hs00943495_m1). ARBP (Rn00821065_g1) and GAPDH (4326317E) were used as endogenous controls. The real-time PCR was performed with 1 μL of the product of reverse transcription in 10 μL of the PCR Master Mix with primers at 300 nM and probe at 200 nM. The Ct (threshold cycle) values were used to calculate the expression that was normalized by the Ct of the endogenous control.

II. Protein Expression

The protein was isolated using the TriPure method and resuspended in SDS. The membranes were incubated with monoclonal antibodies against LRP1 (β chain, clone 8B8, RDI61067) or VLDLR (Santa Cruz Biotechnology Inc, D-17, sc-11823), or CHFR (Cell Signaling, 4297, dilution 1:1000 dilution). In order to check protein loading, the membranes were stained with Ponceau and the membranes were incubated with antibodies against β-tubulin (Abcam, ab6046) in the case of HL-1 or with antibodies against GAPDH (Santa Cruz Biotechnology, Inc., sc-20357) in the case of NRVM.

Monoclonal antibodies against LRP1 were used for detection of the cytoplasmic chain of LRP1 (beta chain, cytoplasmic) through the Western blot technique. Therefore, these antibodies were not able to inhibit the binding capacity of alpha chain of LRP1 (extracellular).

13.11 In Vivo Model of Myocardial Ischaemia

Neutral lipid profile and lipoprotein receptor expression were analyzed in the myocardium of a group of male pigs (Crossbred commercial pigs (Landrace-Largewhite) in which acute myocardial infarction was induced by occlusion of the left descending coronary artery (LAD) for 1.5 hours (n=6) and compared with a control group (sham, intervention without occlusion, n=3) as detailed in previously published work (Vilahur G et al, *J Thromb Haemost* 2009; Vilahur G et al, *J Mol Cell Cardiol* 2011). The coronary artery was occluded by angioplasty with a balloon via femoral. The site of occlusion was distal to the first diagonal branch. Ninety minutes of occlusion results in large transmural infarcts associated with a remodeling process. Samples from the periphery of the necrosis zone in the septal zone (ischaemic zone) and the left ventricle in the remote zone with regard to the infarction (non-ischaemic zone) were taken and used for molecular analysis.

13.12 Patients

A total of 55 hearts explanted from 26 patients with idiopathic dilated cardiomyopathy (DCM) and 29 patients with ischaemic cardiomyopathy (ICM) who underwent transplantation at the Hospital de la Santa Creu i Sant Pau in Barcelona or at the Hospital La Fe in Valencia were collected. Patients were classified according to the criteria of the New York Heart Association (NYHA) and received treatment according to the guidelines of the European Society of Cardiology. The biochemical and ultrasound data of these patients are shown in Table 3. Informed consent was obtained from all patients in accordance with our institutional guidelines. Four healthy hearts were obtained from donors who suffered a traffic accident and were used as controls.

13.13 Immunohistochemistry

The myocardial samples were cut into appropriate blocks and immersed in a fixative solution (4% paraformaldehyde), embedded in OCT, cut into slices of 5 μm in thickness and placed on slides of poly-L-Lysine. Anti-LRP1 antibody (Research Diagnostics, PRO61067) was used as a primary antibody. Prior to the incubation, the sections were washed and the endogenous peroxidase activity was inhibited with $H_2O_2$ using horse serum to inhibit non-specific activity. The primary antibody was detected with the avidin-biotin immunoperoxidase technique using a biotinylated secondary antibody (Vector). 3,3'-diaminobenzidine was used as a chromogen, and hematoxylin was used for nuclear staining. The protocol for VLDLR staining (Santa Cruz Biotechnology, sc-18824) was similar, except that permeabilization before applying the primary antibody was greater. The images were captured with a Nikon Eclipse 80i microscope and digitized with a Retiga 1300i Fast camera (240× magnification).

13.14 Cardiomyocyte Cell Cultures for the Production of Monoclonal Antibodies and Small Molecules for Use in In Vivo Models of Acute Myocardial Infarction The HL-1 culture cell line was used as a model of adult cardiomyocytes. This cell line was kindly provided by Dr. W. C. Claycomb (Louisiana State University Medical Center, New Orleans, La., USA) and has phenotypic characteristics similar to those of adult cardiomyocytes (Claycomb W C et al, *PNAS* 1998). The HL-1 cells shall be kept in Claycomb medium (JRH Biosciences, Lenexa, Kans., USA) with foetal bovine serum (10%), norepinephrine (100 U/mL) and antibiotic. Before seeding, the wells shall be previously covered with gelatin and fibronectin, and the HL-1 cells shall be grown in parallel under normoxic and hypoxic conditions in the absence or presence of lipoproteins (Castellano J et al. *JMCC* 2011*). At this time, our group has stable LRP1-deficient cardiomyocyte lines generated by transfection with lentiviruses containing miRNA sequences that inhibit LRP1 expression (pLenti6.4-CMV-MSGW/miR, Invitrogen). We will compare the effect of the soluble minireceptors and of the antibodies generated, in order to prevent the transfer of esterified cholesterol from VLDL to the hypoxic cardiomyocytes.

13.15 Induction of Acute Myocardial Infarction to Study the Role of LRP1 Receptor Inhibition in Cardioprotection in In Vivo Models of Acute Myocardial Infarction I. Mouse—

For the mouse model, apoE3leiden (E3L) transgenic mice are chosen, whose dyslipidemia pattern resembles that of patients with dysbetalipoproteinemia, in which the elevation of both cholesterol and triglycerides is limited to the VLDL. The mice were endotracheally intubated and connected to a fan following intraperitoneal anesthesia with a mixture of ketamine (50 mg/mL) and xylazine (2%). A left thoracotomy was performed between the 4th and 5th intercostal space to access the heart. The left coronary artery was occluded with a 5-0 suture thread, approximately 2 mm from the origin, between the edge of the left atrium and the pulmonary artery groove; the threads were crossed to completely stop the flow without damaging the artery. The occlusion was visually confirmed by the color change of the affected myocardium, and the disoclussion was verified by the disappearance of the epicardial cyanosis area.

II. Pig—

The pig model was ideal as a preclinical model in cardioprotection since the collateral coronary circulation and arterial anatomy of pigs and humans are quite similar. Furthermore, infarct size was fairly predictable. Induction of infarction in the pig model was performed as previously described in our center (Vilahur G et al, *JMCC* 2011). Twelve hours before the experimental induction of acute myocardial infarction (AMI), a loading dose of clopidogrel (150 mg/kg) was administered. The anesthetic was given by intramuscular injection of Zoletil® (7 mg/kg), Dormitorio® (7 mg/kg) and atropine (0.03 mg/Kg). The animals were subjected to endotracheal intubation and anesthesia was maintained by inhalation of isoflurane (1.5-2%). Continuous infusion of amiodarone (300 mg, 75 mg/h) starts at the beginning of the procedure in all pigs as a prophylaxis for malignant ventricular arrhythmias. Angiography images were used to guide the placement of balloon angioplasty (below the first diagonal branch). Balloon angioplasty (2.5-3 mm) was inflated to nominal pressure (complete occlusion of the coronary artery was verified by fluoroscopy). The occlusion was maintained for ninety minutes and the oxygen levels and electrocardiogram were monitored throughout the surgical procedure. The site of occlusion was located immediately distal to the origin of the first diagonal branch.

13.16 Release of Antibodies

Antibodies were intraperitoneally injected during surgery. In a pilot study, an analysis of the antibody dose required to inhibit VLDL-derived intracellular cholesteryl ester accumulation in ischaemic cardiomyocytes was performed.

13.17 Study of Infarct Size

I. Mouse

To determine infarct size, the animals are killed and the heart mounted on a Langendorff apparatus to perfuse the heart with 10% formalin. After fixing, the scarring area of the sections stained with Masson trichrome (Sigma Aldrich) are measured with Bioquant imaging software and shall be expressed as a percentage of the total area of the left ventricle.

II. Pig—

After death, hearts are cut into sections of 5 mm in thickness from the apex to the atrioventricular groove. Alternative sections will be used for staining with triphenyl tetrazolium chloride (TTC) and Molecular Biology procedures. Blood from these animals is also collected from these animals prior to coronary artery occlusion and prior to killing to detect markers of myocardial necrosis such as troponin-I and CK-MB/CK.

13.18 Echocardiographic Parameters

Transthoracic echocardiography is performed before and after surgery using the Philips iE33 imaging system for pigs and Vevo 2100 (VisualSonics Inc.) equipped with a 30 MHz probe for mice.

13.19 Techniques Related to the Handling of Lipids and Lipoproteins

I. Lipoprotein Isolation.

VLDL and LDL are obtained by sequential ultracentrifugation at 4° C. in a dense KBr solution from plasma of normolipidemic donors. The lipoproteins are dialyzed and their purity is analyzed by agarose gel electrophoresis as previously described by the authors (Llorente-Cortés V et al, *ATVB* 2002*; *ATVB* 2006*).

II. Determination of Free Cholesterol, Cholesteryl Ester and Triglyceride Content in Cell and Tissue Samples.

Cell samples are collected in NaOH and tissue samples are crushed and exhaustively weighed before performing the lipid extraction and the thin layer chromatography of the samples as described previously by the authors (Llorente-Cortés V et al, *ATVB* 2002*, *ATVB* 2006*).

III. Preparation of $^{[3H]}$CE-$^{[14C]}$TG-VLDL and Determination of CE and TG Uptake by Cardiomyocytes VLDL is doubly labeled using a method previously described, with minor modifications. The cholesteryl-1,2-$^3$H—(N) (125 μCi) and trioleate glycerol [$^{14}$C] (25 μCi) (Perkin Elmer Life Sciences) are deposited in a flask with a round bottom to evaporate the organic solvent at 37° C. under vacuum. Then 50 mL of human plasma are added to the flask and allowed to rotate in a water bath under vacuum for 20 hours at 37° C. Thereafter, radiolabeled VLDL are isolated by ultracentrifugation, dialyzed, filtered and stored at 4° C. and protected from light until use.

The ability of the generated monoclonal antibodies to inhibit the uptake of labeled VLDL is analyzed in cell cultures. Uptake is determined by measuring the radioactivity of an aliquot from the cell suspension using an LS6500 scintillation counter. The cpm obtained are normalized by the cellular protein.

13.20 Molecular Biology Techniques

I. Obtention of Tissue Samples

Control mouse hearts are removed and treated. One sample from the ventricle is used for Molecular Biological studies and another for immunohistochemistry.

II. Gel Electrophoresis and "Immunoblotting" (for Analysis of Protein Expression)

Protein expression is studied by electrophoresis in SDS-polyacrylamide gels. The protein is transferred to nitrocellulose filters that have been incubated with antibodies specific to the genes under study (Llorente-Cortés V, *Circulation* 2002*).

III. Real-Time PCR (for analysis of gene expression). Total RNA is isolated from the samples collected in TriPure™ reagent according to the manufacturer's instructions. The genes of interest are analyzed through real-time PCR after cDNA synthesis performed from 1 μg of RNA using the high capacity archive kit (Llorente-Cortés et al, *J Mol Biol* 2006*).

IV. Protein Immunoprecipitation Assays

This technique is used to study the formation of complexes in the intracellular signaling process. The cells are lysed in lysis buffer with protease inhibitors. Lysates are cleansed of debris by centrifugation at 10,000×g for 5 min at 4° C. The protein is then incubated with primary antibodies and then with agarose bound to G proteins overnight at 4° C. The immunoprecipitates are collected by centrifugation at 10,000×g for 5 min at 4° C., resuspended, and washed in lysis buffer. Subsequently, the immunoprecipitates are resuspended in Laemmli loading buffer and analyzed through Western blot.

V. Detection of the Phosphorylation of the Cytoplasmic Chain of LRP1

Anti-LRP1 antibody is used as an immunoprecipitation-inducing antibody, and anti-phosphotyrosine antibody is used as an antibody for the detection of the immunoprecipated complex in the transfer membrane (Boucher P et al, *J Biol Chem* 2002).

VI. Zymography

Metalloprotease activity is measured in the cell supernatants through a zymography using gelatin as a substrate. Equivalent amounts of supernatants are loaded onto 10% polyacrylamide gels containing gelatin at 1 mg/mL and are run at 4° C. The staining of the gels is performed with Coomassie R-250 blue and the gels are subsequently washed out with acetic acid (10%) and methanol (40%). The light bands on the blue background indicate the presence of proteolytic activity. These bands are quantified through densitometry (Otero-Viñas M et al, *Atherosclerosis* 2007*).

VII. Measurement of Oxidative Stress

The cell-permeable compound ($H_2$DCF-DA) (non-fluorescent) is used to measure the intracellular levels of ROS. Within the cells, this compound is de-esterified at 2',7'-dichlorofluorescein ($H_2$DCF) which upon oxidation by ROS leads to the fluorescent compound (DCF) which remains inside the cells. The $H_2$DCF-DA dissolves in DMSO and is added to the cells. The cells are incubated with the compound for 40 min at 37° C. Then the cells are collected and the fluorescence intensity is determined through flow cytometry.

LIST OF SEQUENCES

SEQ ID No: 1: top oligonucleotides designed to inhibit LRP1 expression (miR RNAi-XM_001056970_1919 or RNAi1919)

SEQ ID No: 2: bottom oligonucleotide designed to inhibit LRP1 expression (miR RNAi-XM_001056970_1919 or RNAi1919)

SEQ ID No: 3: top oligonucleotides designed to inhibit LRP1 expression (miR RNAi-XM_001056970_8223 or RNAi8223)

SEQ ID No: 4: bottom oligonucleotides designed to inhibit LRP1 expression (miR RNAi-XM_001056970_8223 or RNAi8223)

SEQ ID No: 5: top oligonucleotides designed to inhibit LRP1 expression (miR RNAi-XM_001056970_8531 or RNAi8531)

SEQ ID No: 6: bottom oligonucleotides designed to inhibit LRP1 expression (miR RNAi-XM_001056970_8531 or RNAi8531)

SEQ ID No: 7: top oligonucleotides designed for universal negative control (pcDNA™6.2-GW/miR-neg)

SEQ ID No: 8: bottom oligonucleotides designed for universal negative control (pcDNA™6.2-GW/miR-neg)

SEQ ID No: 9: vector pLenti6.4™-CMV-MSGW SEQ ID No: 10: linear vector pcDNA™6.2_GW/miR SEQ ID No: 11: vector pDONR™221

SEQ ID No: 12: vector pENTR™221

SEQ ID No: 13: peptide P1, amino acid sequence of cluster II of the alpha chain of the protein LRP1. Within this sequence, the zone of cluster II is identified: 1N7D, coded by the sequence located in the base interval: [1051-1066].

SEQ ID No: 14: peptide P2, amino acid sequence of cluster II of the alpha chain of the protein LRP1. Within this sequence, the zone of cluster II is identified: 1N7D Interface, coded by the sequence located in the base interval: [1090-1104].

SEQ ID No: 15: peptide P3, amino acid sequence of cluster II of the alpha chain of the protein LRP1. Within this sequence, the zone of cluster II is identified: 1N7D Interface, coded by the sequence located in the base interval: [1127-1140].

SEQ ID No: 16: RNAi1919, pcDNA6.2-GW/miR-XM__001056970-1919.

SEQ ID No: 17: RNAi8223, pcDNA6.2-GW/miR-XM__001056970-8223.

SEQ ID No: 18: RNAi8531, pcDNA6.2-GW/miR-XM__001056970-8531.

SEQ ID No: 19: Amino acid sequence of cluster II of the alpha chain of the protein LRP1. Within this sequence are identified P1 (coded by the sequence located in the base interval [1051-1066]), P2 (coded by the sequence located in the base interval [1090-1104]) and P3 (coded by the sequence located in the base interval [1127-1140]).

SEQ ID No: 20: pLenti6.4-CMV-MSGW/miR—XM__001056970—8531.

SEQ ID No: 21: pLenti6.4-CMV-MSGW/miR—XM__001056970—1919.

SEQ ID No: 22: packaging construct pCMV delta R8.2

SEQ ID No: 23: pLenti6.4/R4R2/V5-DEST™

SEQ ID No: 24: pLenti6.4™-CMV-MSGW/miR-XM-001056970-8223

The invention claimed is:

1. A peptide, wherein the peptide is selected from the group consisting of:

peptide P1 (SEQ ID NO: 13), peptide P2 (SEQ ID NO: 14), and peptide P3 (SEQ ID NO: 15).

2. A method for obtaining an antibody, comprising immunizing a subject with an antigen comprising the peptide of claim 1 and obtaining the antibody.

* * * * *